US011939362B2

(12) United States Patent
Oueslati

(10) Patent No.: US 11,939,362 B2
(45) Date of Patent: Mar. 26, 2024

(54) LIGHT-INDUCIBLE PROTEIN AGGREGATION SYSTEM FOR MODELING PROTEINOPATHIES AND NEURODEGENERATIVE DISORDERS

(71) Applicant: UNIVERSITÉ LAVAL, Québec (CA)

(72) Inventor: Abid Oueslati, Québec (CA)

(73) Assignee: UNIVERSITÉ LAVAL, Québec (CA)

(*) Notice: Subject to any disclaimer, the term of this patent is extended or adjusted under 35 U.S.C. 154(b) by 647 days.

(21) Appl. No.: 17/252,323

(22) PCT Filed: Jul. 3, 2019

(86) PCT No.: PCT/CA2019/050914
§ 371 (c)(1),
(2) Date: Dec. 15, 2020

(87) PCT Pub. No.: WO2020/006630
PCT Pub. Date: Jan. 9, 2020

(65) Prior Publication Data
US 2021/0261634 A1   Aug. 26, 2021

Related U.S. Application Data

(60) Provisional application No. 62/693,666, filed on Jul. 3, 2018.

(51) Int. Cl.
C07K 14/47 (2006.01)
A61N 5/06 (2006.01)
(Continued)

(52) U.S. Cl.
CPC .......... C07K 14/4711 (2013.01); A61N 5/062 (2013.01); C07K 14/4702 (2013.01);
(Continued)

(58) Field of Classification Search
CPC ............ C07K 14/4702; C07K 14/4703; C07K 14/4711; C07K 2319/60; C07K 2319/70;
(Continued)

(56) References Cited

U.S. PATENT DOCUMENTS

2012/0237966 A1   9/2012   Dolmetsch et al.

FOREIGN PATENT DOCUMENTS

WO   2018165293 A1   9/2018

OTHER PUBLICATIONS

Beneditti, et al., "Light-activated protein interaction with high spatial subcellular confinement," PNAS vol. 115 No. 10, Feb. 20, 2018, all enclosed pages cited.
(Continued)

Primary Examiner — Jeffrey E. Russel
(74) Attorney, Agent, or Firm — Johnson, Marcou, Isaacs & Nix, LLC; F. Brent Nix, Esq.

(57) ABSTRACT

A light-inducible intracellular protein aggregation system is described herein, which provides invaluable tools to study the role of protein aggregates in proteinopathies and to screen for novel therapeutic compounds. The system generally comprises a cell expressing an alpha-synuclein polypeptide or another proteopathic polypeptide that self-aggregates under pathogenic conditions, operably linked to a photoactivatable polypeptide. Illumination of the photoactivatable polypeptide with light having a wavelength sufficient for photoactivation triggers irreversible accumulation of intracellular protein aggregates comprising the alpha-synuclein polypeptide or proteopathic polypeptide. The intracellular protein aggregates can be made to accumulate in real-time during the illumination, thereby enabling spatiotemporal control of protein aggregation. In some embodiments, the intracellular protein aggregates may exhibit pathologically-relevant properties of those found in disease-
(Continued)

associated proteinopathies, such as irreversibility, auto-perpetuation (seeding) activity, and comprising misfolded proteins rich in beta-sheet conformation.

20 Claims, 33 Drawing Sheets

Specification includes a Sequence Listing.

(51) Int. Cl.
    *C07K 19/00*     (2006.01)
    *C12N 15/86*     (2006.01)
    *G01N 33/68*     (2006.01)
    *A61K 38/00*     (2006.01)

(52) U.S. Cl.
    CPC ......... *C12N 15/86* (2013.01); *G01N 33/6845* (2013.01); *G01N 33/6896* (2013.01); *A61K 38/00* (2013.01); *C07K 2319/60* (2013.01); *C07K 2319/70* (2013.01); *C07K 2319/735* (2013.01); *C12N 2750/14143* (2013.01); *G01N 2800/2835* (2013.01); *G01N 2800/7047* (2013.01)

(58) Field of Classification Search
    CPC .. C07K 2319/735; G01N 33/58; G01N 33/68; G01N 33/6803; G01N 33/6845; G01N 33/6872; G01N 33/6893; G01N 33/6896; G01N 2800/2821; G01N 2800/2828; G01N 2800/2835; G01N 2800/7047
    See application file for complete search history.

(56) References Cited

OTHER PUBLICATIONS

Fares, et al., "Induction of de novo a-synuclein fibrillization in a neuronal model for Parkinson's disease," PNAS published online at www.pnas.org/cgi/doi/10.1073/pnas.1512876113 Feb. 2, 2016, all enclosed pages cited.

Fernagut, et al., "A simple method to measure stride length as an index of nigrostriatal dysfunction in mice, " Journal of Neuroscience Methods 113 (2002), Sep. 17, 2001, all enclosed pages cited.

Giasson, et al., "A Hydrophobic Stretch of 12 Amino Acid Residues in the Middle of a-Synuclein Is Essential for Filament Assembly," Journal of Biological Chemistry, vol. 276, No. 4, Nov. 1, 2000, all enclosed pages cited.

Goedert, et al., "100 years of Lewy pathology," Nat. Rev. Neurol. advance online publication Nov. 27, 2012; doi:10.1038/nrneurol. 2012.242, all enclosed pages cited.

International Search Report and Written Opinion of PCT/CA2019/050914 dated Sep. 10, 2019, all enclosed pages cited.

Jeong, et al., "Wireless Optofluidic Systems for Programmable In Vivo Pharmacology and Optogenetics," Cell 162, 1-13, Jul. 30, 2015, all enclosed pages cited.

Khamo, et al., "Applications of Optobiology in Intact Cells and Multicellular Organisms," J Mol Biol (2017) 429, all enclosed pages cited.

Kim, et al., "Optobiology: Optical control of biological processes via protein engineering," Biochem Soc Trans. Oct. 2013 ; 41(5), all enclosed pages cited.

Knowles, et al., "The amyloid state and its association with protein misfolding diseases," Nature.com vol. Jun. 15, 2014, all enclosed pages cited.

Lashuel, et al., "The many faces of a-synuclein: from structure and toxicity to therapeutic target," Nature.com vol. Jan. 14, 2013, all enclosed pages cited.

Masuda, et al., "Small Molecule Inhibitors of α-Synuclein Filament Assembly," Biochemistry 2006, 45, all enclosed pages cited.

Mccann, et al., "α-Synucleinopathy phenotypes, " Parkinson and Related Disorders 20S1 (2014), all enclosed pages cited.

Oueslati, et al., "Polo-like kinase 2 regulates selective autophagic a-synuclein clearance and suppresses its toxicity In vivo," PNAS www.pnas.org/cgi/doi/10.1073/pnas.1309991110, Aug. 27, 2013, all enclosed pages cited.

Oueslati, et al., "Protein Transmission, Seeding and Degradation: Key Steps for α-Synuclein Prion-Like Propagation," Experimental Neurobiology 2014, all enclosed pages cited.

Oueslati, et al., "Photobiomodulation Suppresses Alpha-Synuclein-Induced Toxicity in an AAV-Based Rat Genetic Model of Parkinson's Disease," Plos One, DOI:10.1371/journal.pone.0140880 Oct. 20, 2015, all enclosed pages cited.

Rozas, et al., "An automated rotarod method for quantitative drug-free evaluation of overall motor deficits in rat models of parkinsonism," Brain Research Protocols 2 (1997), all enclosed pages cited.

Schallert, et al., "CNS plasticity and assessment of forelimb sensorimotor outcome in unilateral rat models of stroke, cortical ablation, parkinsonism and spinal cord injury," Neuropharmacology 39 (2000), all enclosed pages cited.

Shults, "Lewy bodies," PNAS www.pnas.org/cgi/doi/10.1073/pnas. 0509567103 Feb. 7, 2006, all enclosed pages cited.

Spillantini, et al., α-Synuclein in Lewy bodies, Nature, vol. 388, Aug. 28, 1997, all enclosed pages cited.

Stefani, et al., "Protein aggregation and aggregate toxicity: new insights into protein folding, misfolding diseases and biological evolution," J Mol Med (2003), 81, all enclosed pages cited.

Taslimi, et al., "An optimized optogenetic clustering tool for probing protein interaction and function," Nat Commun., 5: 1925 doi:10.1038/ncomms5925, all enclosed pages cited. (2015).

Vazey, et al., "New tricks for old dogmas: Optogenetic and designer receptor insights for Parkinson's disease, " Brain Res. May 2, 20130; all enclosed pages cited.

West, et al., "Unbiased Stereological Estimation of the Total Number of Neurons in the Subdivisions of the Rat Hippocampus Using the Optical Fractionator," The Anatomical Record, 231: 482-497 (1991).

Zhang, et al., "Optogenetic control of intracellular signaling pathways," Trends Biotechnol. Feb. 2015 ; 33(2): 92-100. doi:10.1016/j.tibtech.2014.11.007.

Zhu, et al., "The Flavonoid Baicalein Inhibits Fibrillation of α-Synuclein and Disaggregates Existing Fibrils, " The Journal of Biochemical Chemistry, vol. 279, No. 26, Issue of Jun. 25, (2004), all enclosed pages cited.

Fig. 9
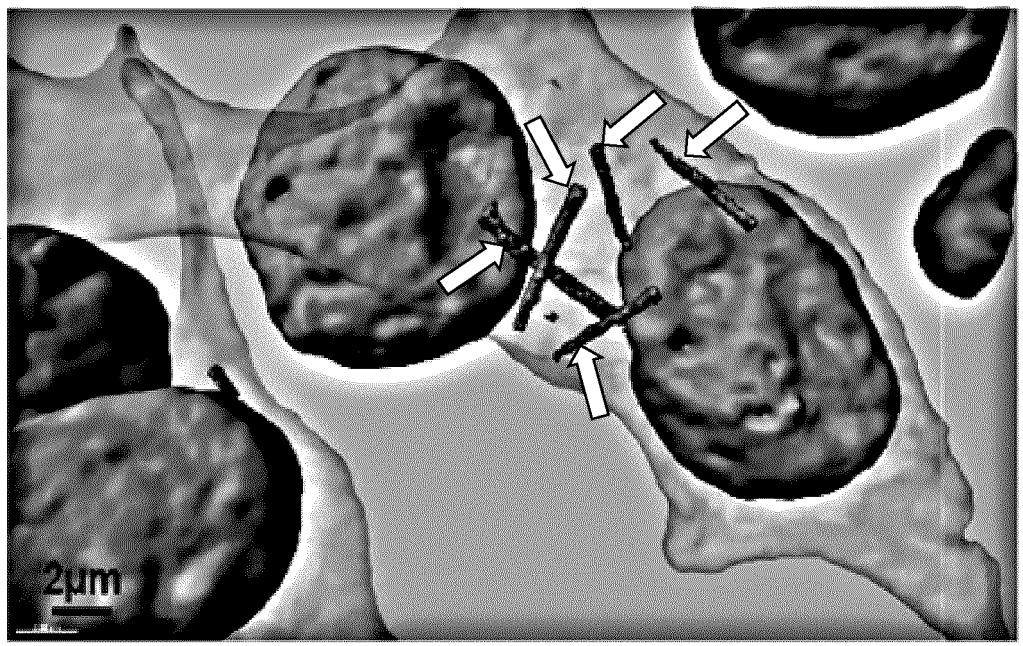
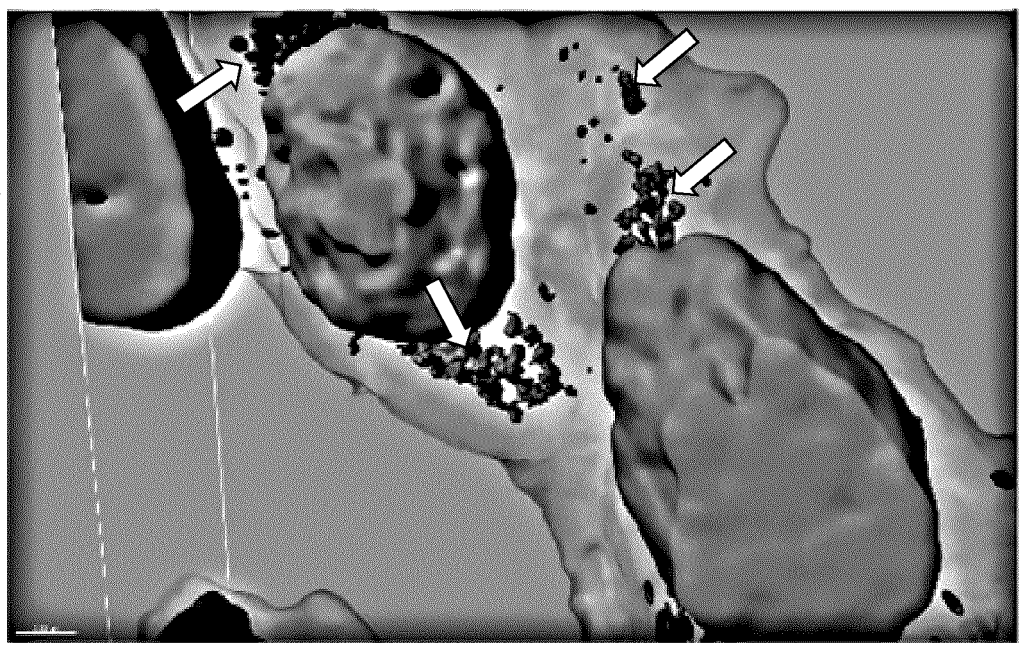

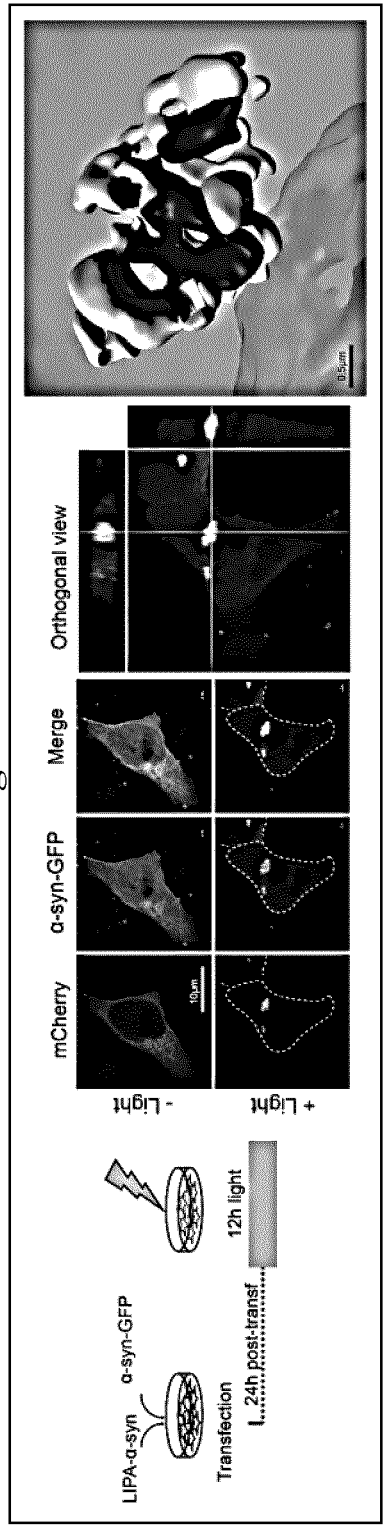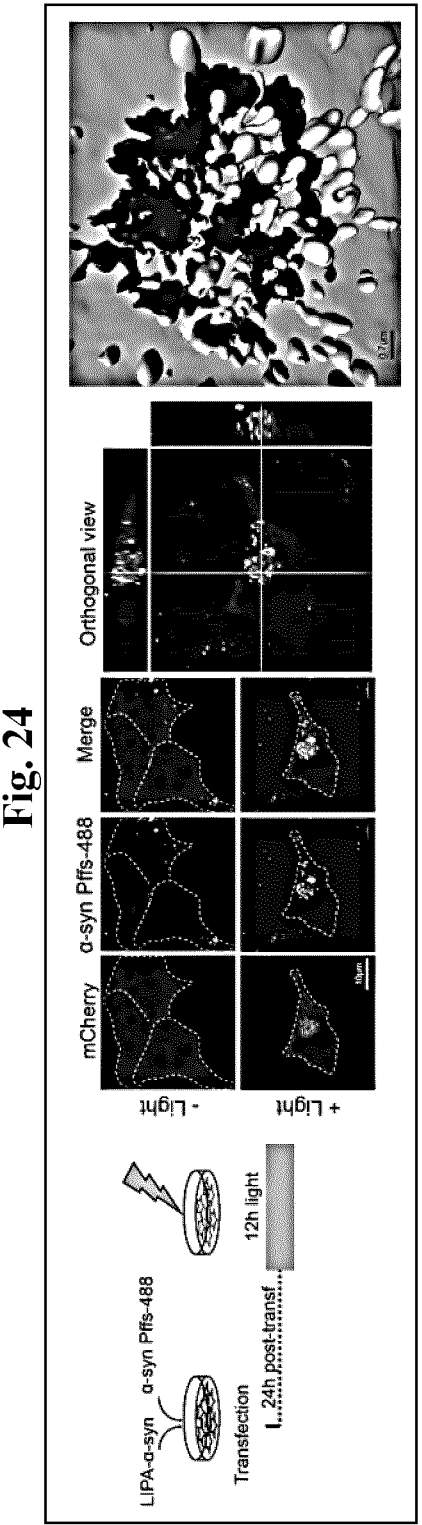

Day 1
Stereotaxic injection
of AAV-LIPA
Implantation of wireless
optogenetic light source Day 15
Stimulation (1 week):
30 min, every other day
40 Hz / 10 ms pulse width Day 21
Sacrifice and tissue
processing mCherry    α-syn (BD)    merge mCherry    α-syn (FL140)    merge Fig. 54E
Fig. 54F
| mCherry LIPA | Alexa 488 Htt | Merge + DAPI |
|---|---|---|
| 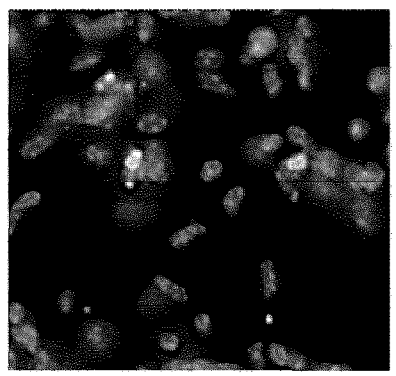 | 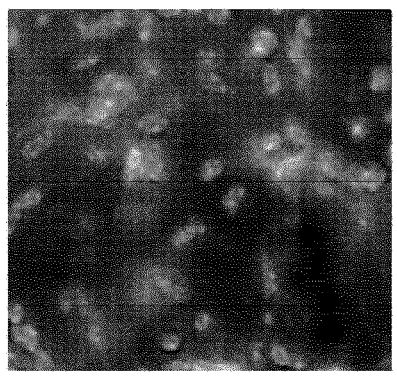 | 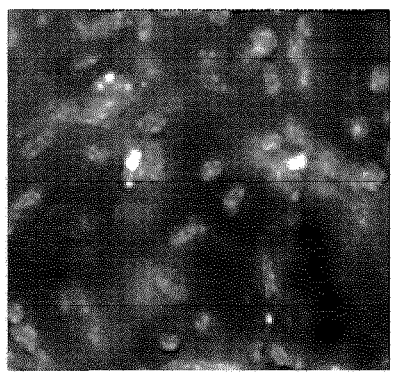 |

SEQUENCE LISTING

<160> NUMBER OF SEQ ID NOS: 6

<210> SEQ ID NO 1
<211> LENGTH: 6925
<212> TYPE: DNA
<213> ORGANISM: Artificial Sequence
<220> FEATURE:
<223> OTHER INFORMATION: pAAV-LIPA-Empty
<220> FEATURE:
<221> NAME/KEY: misc_feature
<222> LOCATION: (1377)..(2870)
<223> OTHER INFORMATION: Arabidopsis thaliana cryptochrome 2 (CRY2)

<400> SEQUENCE: 1

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggttcc | tgcggccgca | cgcgtggagc | tagttattaa | tagtaatcaa | 180 |
| ttacggggtc | attagttcat | agcccatata | tggagttccg | cgttacataa | cttacggtaa | 240 |
| atggcccgcc | tggctgaccg | cccaacgacc | ccgcccatt | gacgtcaata | atgacgtatg | 300 |
| ttcccatagt | aacgtcaata | gggactttcc | attgacgtca | atgggtggag | tatttacggt | 360 |
| aaactgccca | cttggcagta | catcaagtgt | atcatatgcc | aagtacgccc | cctattgacg | 420 |
| tcaatgacgg | taaatggccc | gcctggcatt | atgcccagta | catgacctta | tgggactttc | 480 |
| ctacttggca | gtacatctac | gtattagtca | tcgctattac | catggtgatg | cggttttggc | 540 |
| agtacatcaa | tgggcgtgga | tagcggtttg | actcacgggg | atttccaagt | ctccacccca | 600 |
| ttgacgtcaa | tgggagtttg | ttttggcacca | aaatcaacgg | gactttccaa | aatgtcgtaa | 660 |
| caactccgcc | ccattgacgc | aaatgggcgg | taggcgtgta | cggtgggagg | tctatataag | 720 |
| cagagctcgt | ttagtgaacc | gtcagatcgc | ctggagacgc | catccacgct | gttttgacct | 780 |
| ccatagaaga | caccgggacc | gatccagcct | ccgcggattc | gaatcccggc | cgggaacggt | 840 |
| gcattggaac | gcggattccc | cgtgccaaga | gtgacgtaag | taccgcctat | agagtctata | 900 |
| ggcccacaaa | aaatgctttc | ttcttttaat | atacttttttt | gtttatctta | tttctaatac | 960 |
| tttccctaat | ctctttcttt | cagggcaata | atgatacaat | gtatcatgcc | tctttgcacc | 1020 |
| attctaaaga | ataacagtga | taatttctgg | gttaaggcaa | tagcaatatt | tctgcatata | 1080 |
| aatatttctg | catataaatt | gtaactgatg | taagaggttt | catattgcta | atagcagcta | 1140 |
| caatccagct | accattctgc | ttttatttta | tggttgggat | aaggctggat | tattctgagt | 1200 |
| ccaagctagg | ccctttttgct | aatcatgttc | atacctctta | tcttcctccc | acagctcctg | 1260 |
| ggcaacgtgc | tggtctgtgt | gctggcccat | cactttggca | agaattggg | attcgaacat | 1320 |
| cgattgaatt | ccccgggat | cctctagcgc | taccggactc | agatctcgag | gccaccatga | 1380 |
| agatggacaa | aaagactata | gtttggttta | agagagacct | aaggattgag | ataatcctg | 1440 |
| cattagcagc | agctgctcac | gaaggatctg | ttttttcctgt | cttcatttgg | tgtcctgaag | 1500 |
| aagaaggaca | gttttatcct | ggaagagctt | caagatggtg | gatgaaacaa | tcacttgctc | 1560 |
| acttatctca | atccttgaag | gctcttggat | ctgacctcac | tttaatcaaa | acccacaaca | 1620 |
| cgatttcagc | gatcttggat | tgtatccgcg | ttaccggtgc | tacaaaagtc | gtctttaacc | 1680 |
| acctctatga | tcctgttcg | ttagttcggg | accataccgt | aaaggagaag | ctggtggaac | 1740 |
| gtgggatctc | tgtgcaaagc | tacaatggag | atcattgta | tgaaccgtgg | gagatatact | 1800 |
| gcgaaaaggg | caaacctttt | acgagtttca | attcttactg | gaagaaatgc | ttagatatgt | 1860 |
| cgattgaatc | cgttatgctt | cctcctccttt | ggcggttgat | gccaataact | gcagcggctg | 1920 |

```
aagcgatttg ggcgtgttcg attgaagaac tagggctgga gaatgaggcc gagaaaccga    1980
gcaatgcgtt gttaactaga gcttggtctc caggatggga caatgctgat aagttactaa    2040
atgagttcat cgagaagcag ttgatagatt atgcaaagaa cagcaagaaa gttgttggga    2100
attctacttc actactttct ccgtatctcc atttcgggga aataagcgtc agacacgttt    2160
tccagtgtgc ccggatgaaa caaattatat gggcaagaga taagaacagt gaaggagaag    2220
aaagtgcaga tcttttcttt aggggaatcg gtttaagaga gtattctcgg tatatatgtt    2280
tcaacttccc gtttactcac gagcaatcgt tgttgagtca tcttcggttt ttcccttggg    2340
atgctgatgt tgataagttc aaggcctgga gacaaggcag gaccggttat ccgttggtgg    2400
atgccggaat gagagagctt tgggctaccg gatggatgca taacagaata agagtgattg    2460
tttcaagctt tgctgtgaag tttcttctcc ttccatggaa atggggaatg aagtatttct    2520
gggatacact tttggatgct gatttggaat gtgacatcct tggctggcag tatatctctg    2580
ggagtatccc cgatggccac gagcttgatc gcttggacaa tcccgcgtta caaggcgcca    2640
aatatgaccc agaaggtgag tacataaggc aatggcttcc cgagcttgcg agattgccaa    2700
ctgaatggat ccatcatcca tgggacgctc ctttaaccgt actcaaagct tctggtgtgg    2760
aactcggaac aaactatgcg aaacccattg tagacatcga cacagctcgt gagctactag    2820
ctaaagctat ttcaagaacc cgtggagcac agatcatgat cggagcagca gcccgggatc    2880
caccggtcgc caccatggtg agcaagggcg aggaggataa catggccatc atcaaggagt    2940
tcatgcgctt caaggtgcac atggagggct ccgtgaacgg ccacgagttc gagatcgagg    3000
gcgagggcga gggccgcccc tacgagggca cccagaccgc caagctgaag gtgaccaagg    3060
gtggccccct gcccttcgcc tgggacatcc tgtcccctca gttcatgtac ggctccaagg    3120
cctacgtgaa gcaccccgcc gacatccccg actacttgaa gctgtccttc cccgagggct    3180
tcaagtggga gcgcgtgatg aacttcgagg acggcggcgt ggtgaccgtg acccaggact    3240
cctccctgca ggacggcgag ttcatctaca aggtgaagct gcgcggcacc aacttcccct    3300
ccgacggccc cgtaatgcag aagaagacca tgggctggga ggcctcctcc gagcggatgt    3360
accccgagga cggcgccctg aagggcgaga tcaagcagag gctgaagctg aaggacggcg    3420
gccactacga cgctgaggtc aagaccacct acaaggccaa gaagcccgtg cagctgcccg    3480
gcgcctacaa cgtcaacatc aagttggaca tcacctccca caacgaggac tacaccatcg    3540
tggaacagta cgaacgcgcc gagggccgcc actccaccgg cggcatggac gagctgtaca    3600
agtaaagcgg ccgcgactct agagtcgacc tgcagaagct tgcctcgagc agcgctgctc    3660
gagagatcta cgggtggcat ccctgtgacc cctccccagt gcctctcctg gccctggaag    3720
ttgccactcc agtgcccacc agccttgtcc taataaaatt aagttgcatc attttgtctg    3780
actaggtgtc cttctataat attatggggt ggaggggggt ggtatggagc aaggggcaag    3840
ttgggaagac aacctgtagg gcctgcgggg tctattggga accaagctgg agtgcagtgg    3900
cacaatcttg gctcactgca atctccgcct cctgggttca agcgattctc ctgcctcagc    3960
ctcccgagtt gttgggattc caggcatgca tgaccaggct cagctaattt ttgttttttt    4020
ggtagagacg gggtttcacc atattggcca ggctggtctc caactcctaa tctcaggtga    4080
tctacccacc ttggcctccc aaattgctgg gattacaggc gtgaaccact gctcccttcc    4140
ctgtccttct gattttgtag gtaaccacgt gcggaccgag cggccgcagg aaccccctagt   4200 gatggagttg gccactccct ctctgcgcgc tcgctcgctc actgaggccg ggcgaccaaa    4260
```

```
ggtcgcccga cgcccgggct tgcccgggcc ggcctcagtg agcgagcgag cgcgcagctg   4320
cctgcagggg cgcctgatgc ggtatttttct ccttacgcat ctgtgcggta tttcacaccg   4380
catacgtcaa agcaaccata gtacgcgccc tgtagcggcg cattaagcgc ggcgggtgtg   4440
gtggttacgc gcagcgtgac cgctacactt gccagcgccc tagcgcccgc tcctttcgct   4500 ttcttcccctt cctttctcgc cacgttcgcc ggctttcccc gtcaagctct aaatcggggg   4560
ctccctttag ggttccgatt tagtgcttta cggcacctcg accccaaaaa acttgatttg   4620
ggtgatggtt cacgtagtgg gccatcgccc tgatagacgg ttttttcgccc tttgacgttg   4680 gagtccacgt tctttaatag tggactcttg ttccaaactg gaacaacact caaccctatc   4740
tcgggctatt cttttgattt ataagggatt ttgccgattt cggcctattg gttaaaaaat   4800
gagctgattt aacaaaaatt taacgcgaat tttaacaaaa tattaacgtt tacaatttta   4860
tggtgcactc tcagtacaat ctgctctgat gccgcatagt taagccagcc ccgacacccg   4920
ccaacacccg ctgacgcgcc ctgacgggct tgtctgctcc cggcatccgc ttacagacaa   4980
gctgtgaccg tctccgggag ctgcatgtgt cagaggtttt caccgtcatc accgaaacgc   5040
gcgagacgaa agggcctcgt gatacgccta ttttttatagg ttaatgtcat gataataatg   5100
gtttcttaga cgtcaggtgg cacttttcgg ggaaatgtgc gcggaacccc tatttgttta   5160
tttttctaaa tacattcaaa tatgtatccg ctcatgagac aataaccctg ataaatgctt   5220
caataatatt gaaaaaggaa gagtatgagt attcaacatt tccgtgtcgc ccttattccc   5280
ttttttgcgg cattttgcct tcctgttttt gctcacccag aaacgctggt gaaagtaaaa   5340
gatgctgaag atcagttggg tgcacgagtg ggttacatcg aactggatct caacagcggt   5400
aagatccttg agagttttcg ccccgaagaa cgttttccaa tgatgagcac ttttaaagtt   5460
ctgctatgtg cgcggtatt atcccgtatt gacgccgggc aagagcaact cggtcgccgc   5520
atacactatt ctcagaatga cttggttgag tactcaccag tcacagaaaa gcatcttacg   5580
gatggcatga cagtaagaga attatgcagt gctgccataa ccatgagtga taacactgcg   5640
gccaacttac ttctgacaac gatcggagga ccgaaggagc taaccgcttt tttgcacaac   5700 atggggatc atgtaactcg ccttgatcgt tgggaaccgg agctgaatga agccatacca   5760
aacgacgagc gtgacaccac gatgcctgta gcaatggcaa caacgttgcg caaactatta   5820
actggcgaac tacttactct agcttcccgg caacaattaa tagactggat ggaggcggat   5880
aaagttgcag gaccacttct gcgctcggcc cttccggctg gctggtttat tgctgataaa   5940
tctggagccg gtgagcgtgg gtctcgcggt atcattgcag cactggggcc agatggtaag   6000
ccctcccgta tcgtagttat ctacacgacg gggagtcagg caactatgga tgaacgaaat   6060
agacagatcg ctgagatagg tgcctcactg attaagcatt ggtaactgtc agaccaagtt   6120
tactcatata ctttagat tgatttaaaa cttcattttt aatttaaaag gatctaggtg   6180
aagatccttt ttgataatct catgaccaaa atcccttaac gtgagttttc gttccactga   6240
gcgtcagacc ccgtagaaaa gatcaaagga tcttcttgag atccttttttt tctgcgcgta   6300 atctgctgct tgcaaacaaa aaaaccaccg ctaccagcgg tggtttgttt gccggatcaa   6360
gagctaccaa ctcttttcc gaaggtaact ggcttcagca gagcgcagat accaaatact   6420
gtccttctag tgtagccgta gttaggccac cacttcaaga actctgtagc accgcctaca   6480
tacctcgctc tgctaatcct gttaccagtg gctgctgcca gtggcgataa gtcgtgtctt   6540
accgggttgg actcaagacg atagttaccg gataaggcgc agcggtcggg ctgaacgggg   6600
ggttcgtgca cacagcccag cttggagcga acgacctaca ccgaactgag atacctacag   6660
```

```
cgtgagctat gagaaagcgc cacgcttccc gaagggagaa aggcggacag gtatccggta   6720
agcggcaggg tcggaacagg agagcgcacg agggagcttc caggggggaaa cgcctggtat   6780 ctttatagtc ctgtcgggtt tcgccacctc tgacttgagc gtcgattttt gtgatgctcg   6840 tcagggggc ggagcctatg gaaaaacgcc agcaacgcgg ccttttttacg gttcctggcc    6900 ttttgctggc cttttgctca catgt                                          6925
```

<210> SEQ ID NO 2
<211> LENGTH: 7396
<212> TYPE: DNA
<213> ORGANISM: Artificial Sequence
<220> FEATURE:
<223> OTHER INFORMATION: pAAV-LIPA-alpha-syn
<220> FEATURE:
<221> NAME/KEY: misc_feature
<222> LOCATION: (1848)..(3341)
<223> OTHER INFORMATION: Arabidopsis thaliana cryptochrome 2 (CRY2)

<400> SEQUENCE: 2

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtggagc tagttattaa tagtaatcaa    180
ttacggggtc attagttcat agcccatata tggagttccg cgttacataa cttacggtaa    240
atggcccgcc tggctgaccg cccaacgacc cccgcccatt gacgtcaata atgacgtatg    300
ttcccatagt aacgtcaata gggactttcc attgacgtca atgggtggag tatttacggt    360
aaactgccca cttggcagta catcaagtgt atcatatgcc aagtacgccc cctattgacg    420
tcaatgacgg taaatggccc gcctggcatt atgcccagta catgacctta tgggactttc    480
ctacttggca gtacatctac gtattagtca tcgctattac catggtgatg cggttttggc    540
agtacatcaa tgggcgtgga tagcggtttg actcacgggg atttccaagt ctccacccca    600
ttgacgtcaa tgggagtttg ttttgcacca aaatcaacgg gactttccaa aatgtcgtaa    660
caactccgcc ccattgacgc aaatgggcgg taggcgtgta cggtgggagg tctatataag    720
cagagctcgt ttagtgaacc gtcagatcgc ctggagacgc catccacgct gttttgacct    780
ccatagaaga caccgggacc gatccagcct ccgcggattc gaatcccggc cgggaacggt    840
gcattggaac gcggattccc cgtgccaaga gtgacgtaag taccgcctat agagtctata    900
ggcccacaaa aaatgctttc ttcttttaat atacttttt gtttatctta tttctaatac    960
tttccctaat ctctttcttt cagggcaata atgatacaat gtatcatgcc tctttgcacc   1020
attctaaaga ataacagtga taatttctgg gttaaggcaa tagcaatatt tctgcatata   1080
aatatttctg catataaatt gtaactgatg taagaggttt catattgcta atagcagcta   1140
caatccagct accattctgc ttttatttta tggttgggat aaggctggat tattctgagt   1200
ccaagctagg ccctttttgct aatcatgttc atacctctta tcttcctccc acagctcctg   1260
ggcaacgtgc tggtctgtgt gctggcccat cactttggca agaattggg attcgaacat   1320 cgattgaatt ccccggggat cctctagcgc taccggactc agatctcgag gacagtgtgg   1380
tgtaaaggaa ttcattagcc atggatgtat tcatgaaagg actttcaaag gccaaggagg   1440
gagttgtggc tgctgctgag aaaaccaaac agggtgtggc agaagcagca ggaaagacaa   1500
aagagggtgt tctctatgta ggctccaaaa ccaaggaggg agtggtgcat ggtgtggcaa   1560
cagtggctga gaagaccaaa gagcaagtga caaatgttgg aggagcagtg gtgacgggtg   1620
```

```
tgacagcagt agcccagaag acagtggagg gagcagggag cattgcagca gccactggct    1680
ttgtcaaaaa ggaccagttg ggcaagaatg aagaaggagc cccacaggaa ggaattctgg    1740
aagatatgcc tgtggatcct gacaatgagg cttatgaaat gccttctgag gaagggtatc    1800
aagactacga acctgaagcc ggtaccgcgg gcccggtcga ggccaccatg aagatggaca    1860
aaaagactat agtttggttt agaagagacc taaggattga ggataatcct gcattagcag    1920
cagctgctca cgaaggatct gttttttcctg tcttcatttg gtgtcctgaa gaagaaggac    1980
agttttatcc tggaagagct tcaagatggt ggatgaaaca atcacttgct cacttatctc    2040
aatccttgaa ggctcttgga tctgacctca ctttaatcaa aacccacaac acgatttcag    2100
cgatcttgga ttgtatccgc gttaccggtg ctacaaaagt cgtctttaac cacctctatg    2160
atcctgtttc gttagttcgg gaccataccg taaaggagaa gctggtggaa cgtgggatct    2220
ctgtgcaaag ctacaatgga gatctattgt atgaaccgtg ggagatatac tgcgaaaagg    2280
gcaaaccttt tacgagtttc aattcttact ggaagaaatg cttagatatg tcgattgaat    2340
ccgttatgct tcctcctcct tggcggttga tgccaataac tgcagcggct gaagcgattt    2400
gggcgtgttc gattgaagaa ctagggctgg agaatgaggc cgagaaaccg agcaatgcgt    2460
tgttaactag agcttggtct ccaggatgga gcaatgctga taagttacta aatgagttca    2520
tcgagaagca gttgatagat tatgcaaaga acagcaagaa agttgttggg aattctactt    2580
cactactttc tccgtatctc catttcgggg aaataagcgt cagacacgtt ttccagtgtg    2640
cccggatgaa acaaattata tgggcaagag ataagaacag tgaaggagaa gaaagtgcag    2700
atcttttcct taggggaatc ggtttaagag agtattctcg gtatatatgt ttcaacttcc    2760
cgtttactca cgagcaatcg ttgttgagtc atcttcggtt tttcccttgg gatgctgatg    2820
ttgataagtt caaggcctgg agacaaggca ggaccggtta tccgttggtg gatgccggaa    2880
tgagagagct ttgggctacc ggatggatgc ataacagaat aagagtgatt gtttcaagct    2940
ttgctgtgaa gttcttctc cttccatgga aatggggaat gaagtatttc tgggatacac    3000
ttttggatgc tgatttggaa tgtgacatcc ttggctggca gtatatctct gggagtatcc    3060
ccgatggcca cgagcttgat cgcttggaca atcccgcgtt acaaggcgcc aaatatgacc    3120
cagaaggtga gtacataagg caatggcttc ccgagcttgc gagattgcca actgaatgga    3180
tccatcatcc atgggacgct cctttaaccg tactcaaagc ttctggtgtg aactcggaa    3240
caaactatgc gaaacccatt gtagacatcg acacagctcg tgagctacta gctaaagcta    3300
tttcaagaac ccgtggagca cagatcatga tcggagcagc agcccgggat ccaccggtcg    3360
ccaccatggt gagcaagggc gaggaggata acatggccat catcaaggag ttcatgcgct    3420
tcaaggtgca catggagggc tccgtgaacg gccacgagtt cgagatcgag ggcgagggcg    3480
agggccgccc ctacgagggc acccagaccg ccaagctgaa ggtgaccaag ggtggccccc    3540
tgcccttcgc ctgggacatc ctgtcccctc agttcatgta cggctccaag gcctacgtga    3600
agcaccccgc cgacatcccc gactacttga agctgtcctt ccccgagggc ttcaagtggg    3660
agcgcgtgat gaacttcgag gacggcggcg tggtgaccgt gacccaggac tcctcccctgc    3720
aggacgcgca gttcatctac aaggtgaagc tgcgcggcac caacttcccc tccgacggcc    3780
ccgtaatgca gaagaagacc atgggctggg aggcctcctc cgagcggatg taccccgagg    3840
acggcgccct gaagggcgag atcaagcaga ggctgaagct gaaggacggc ggccactacg    3900
acgctgaggt caagaccacc tacaaggcca agaagcccgt gcagctgccc ggcgcctaca    3960
acgtcaacat caagttggac atcaccctcc caacgagga ctacaccatc gtggaacagt    4020
```

```
acgaacgcgc cgagggccgc cactccaccg gcggcatgga cgagctgtac aagtaaagcg      4080
gccgcgactc tagagtcgac ctgcagaagc ttgcctcgag cagcgctgct cgagagatct      4140
acgggtggca tccctgtgac ccctccccag tgcctctcct ggccctggaa gttgccactc      4200
cagtgcccac cagccttgtc ctaataaaat aagttgcat cattttgtct gactaggtgt       4260
ccttctataa tattatgggg tggagggggg tggtatggag caaggggcaa gttgggaaga      4320
caacctgtag ggcctgcggg gtctattggg aaccaagctg gagtgcagtg gcacaatctt      4380
ggctcactgc aatctccgcc tcctgggttc aagcgattct cctgcctcag cctcccgagt      4440
tgttgggatt ccaggcatgc atgaccaggc tcagctaatt tttgttttt tggtagagac       4500 ggggtttcac catattggcc aggctggtct ccaactccta atctcaggtg atctacccac      4560
cttggcctcc caaattgctg gattacagg cgtgaaccac tgctcccttc cctgtccttc       4620
tgattttgta ggtaaccacg tgcggaccga gcggccgcag aaccccctag tgatggagtt     4680
ggccactccc tctctgcgcg ctcgctcgct cactgaggcc gggcgaccaa aggtcgcccg      4740
acgcccgggc tttgcccggg cggcctcagt gagcgagcga gcgcgcagct gcctgcaggg     4800
gcgcctgatg cggtattttc tccttacgca tctgtgcggt atttcacacc gcatacgtca     4860
aagcaaccat agtacgcgcc ctgtagcggc gcattaagcg cggcgggtgt ggtggttacg     4920
cgcagcgtga ccgctacact tgccagcgcc ctagcgcccg ctcctttcgc tttcttccct     4980
tcctttctcg ccacgttcgc cggctttccc cgtcaagctc taaatcgggg gctcccttta     5040
gggttccgat ttagtgcttt acggcacctc gaccccaaaa aacttgattt gggtgatggt     5100
tcacgtagtg ggccatcgcc ctgatagacg ttttttcgcc ctttgacgtt ggagtccacg     5160
ttctttaata gtggactctt gttccaaact ggaacaacac tcaaccctat ctcgggctat     5220
tcttttgatt tataagggat tttgccgatt tcggcctatt ggttaaaaaa tgagctgatt     5280
taacaaaaat ttaacgcgaa ttttaacaaa atattaacgt ttacaatttt atggtgcact     5340
ctcagtacaa tctgctctga tgccgcatag ttaagccagc cccgacaccc gccaacaccc     5400
gctgacgcgc cctgacgggc ttgtctgctc ccggcatccg cttacagaca agctgtgacc     5460
gtctccggga gctgcatgtg tcagaggttt tcaccgtcat caccgaaacg cgcgagacga     5520
aagggcctcg tgatacgcct atttttatag gttaatgtca tgataataat ggtttcttag     5580
acgtcaggtg gcacttttcg gggaaatgtg cgcggaaccc ctatttgttt attttcctaa     5640
atacattcaa atatgtatcc gctcatgaga caataaccct gataaatgct tcaataatat     5700
tgaaaaagga agagtatgag tattcaacat ttccgtgtcg cccttattcc cttttttgcg     5760 gcatttgcc ttcctgtttt tgctcaccca gaaacgctgg tgaaagtaaa agatgctgaa      5820
gatcagttgg gtgcacgagt gggttacatc gaactggatc tcaacagcgg taagatcctt     5880
gagagttttc gccccgaaga acgttttcca atgatgagca cttttaaagt tctgctatgt     5940
ggcgcggtat tatcccgtat tgacgccggg caagagcaac tcggtcgccg catacactat     6000
tctcagaatg acttggttga gtactcacca gtcacagaaa agcatcttac ggatggcatg     6060
acagtaagag aattatgcag tgctgccata accatgagtg ataacactgc ggccaactta     6120
cttctgacaa cgatcggagg accgaaggag ctaaccgctt ttttgcacaa catgggggat     6180
catgtaactc gccttgatcg ttgggaaccg gagctgaatg aagccatacc aaacgacgag     6240
cgtgacacca cgatgcctgt agcaatggca acaacgttgc gcaaactatt aactggcgaa     6300
ctacttactc tagcttcccg gcaacaatta atagactgga tggaggcgga taaagttgca     6360
```

```
ggaccacttc tgcgctcggc ccttccggct ggctggttta ttgctgataa atctggagcc      6420
ggtgagcgtg ggtctcgcgg tatcattgca gcactgggc cagatggtaa gccctcccgt       6480
atcgtagtta tctacacgac ggggagtcag gcaactatgg atgaacgaaa tagacagatc      6540
gctgagatag gtgcctcact gattaagcat tggtaactgt cagaccaagt ttactcatat      6600
atactttaga ttgatttaaa acttcatttt taatttaaaa ggatctaggt gaagatcctt      6660
tttgataatc tcatgaccaa aatcccttaa cgtgagtttt cgttccactg agcgtcagac      6720
cccgtagaaa agatcaaagg atcttcttga gatccttttt ttctgcgcgt aatctgctgc      6780
ttgcaaacaa aaaaaccacc gctaccagcg gtggtttgtt tgccggatca agagctacca      6840 actcttttc cgaaggtaac tggcttcagc agagcgcaga taccaaatac tgtccttcta       6900
gtgtagccgt agttaggcca ccacttcaag aactctgtag caccgcctac atacctcgct      6960
ctgctaatcc tgttaccagt ggctgctgcc agtggcgata agtcgtgtct taccgggttg      7020
gactcaagac gatagttacc ggataaggcg cagcggtcgg gctgaacggg gggttcgtgc      7080
acacagccca gcttggagcg aacgacctac accgaactga gatacctaca gcgtgagcta      7140
tgagaaagcg ccacgcttcc cgaagggaga aaggcggaca ggtatccggt aagcggcagg      7200
gtcggaacag gagagcgcac gagggagctt ccagggggaa acgcctggta tctttatagt      7260
cctgtcgggt ttcgccacct ctgacttgag cgtcgatttt tgtgatgctc gtcaggggg      7320 cggagcctat ggaaaaacgc cagcaacgcg gcctttttac ggttcctggc cttttgctgg      7380
ccttttgctc acatgt                                                     7396

<210> SEQ ID NO 3
<211> LENGTH: 7301
<212> TYPE: DNA
<213> ORGANISM: Artificial Sequence
<220> FEATURE:
<223> OTHER INFORMATION: pAAV-LIPA-alpha-syn-deltaNAC
<220> FEATURE:
<221> NAME/KEY: misc_feature
<222> LOCATION: (1753)..(3246)
<223> OTHER INFORMATION: Arabidopsis thaliana cryptochrome 2 (CRY2)

<400> SEQUENCE: 3
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgca cgcgtggagc tagttattaa tagtaatcaa       180
ttacggggtc attagttcat agcccatata tggagttccg cgttacataa cttacggtaa       240
atggcccgcc tggctgaccg cccaacgacc cccgcccatt gacgtcaata atgacgtatg       300
ttcccatagt aacgtcaata gggactttcc attgacgtca atgggtggag tatttacggt       360
aaactgccca cttggcagta catcaagtgt atcatatgcc aagtacgccc cctattgacg       420
tcaatgacgg taaatggccc gcctggcatt atgcccagta catgacctta tgggactttc       480
ctacttggca gtacatctac gtattagtca tcgctattac catggtgatg cggttttggc       540
agtacatcaa tgggcgtgga tagcggtttg actcacgggg atttccaagt ctccacccca      600
ttgacgtcaa tgggagtttg ttttgcacca aaatcaacgg gactttccaa aatgtcgtaa      660
caactccgcc ccattgacgc aaatgggcgg taggcgtgta cggtgggagg tctatataag      720
cagagctcgt ttagtgaacc gtcagatcgc ctggagacgc catccacgct gttttgacct      780
ccatagaaga caccgggacc gatccagcct ccgcggattc gaatcccggc cgggaacggt      840
gcattggaac gcggattccc cgtgccaaga gtgacgtaag taccgcctat agagtctata      900
```

```
ggcccacaaa aaatgctttc ttcttttaat atacttttt gtttatctta tttctaatac    960
tttccctaat ctctttcttt cagggcaata atgatacaat gtatcatgcc tctttgcacc  1020
attctaaaga ataacagtga taatttctgg gttaaggcaa tagcaatatt tctgcatata  1080
aatatttctg catataaatt gtaactgatg taagagggtt catattgcta atagcagcta  1140
caatccagct accattctgc ttttatttta tggttgggat aaggctggat tattctgagt  1200
ccaagctagg cccttttgct aatcatgttc atacctctta tcttcctccc acagctcctg  1260
ggcaacgtgc tggtctgtgt gctggcccat cactttggca agaattggg attcgaacat   1320
cgattgaatt ccccggggat cctctagccc accatggatg tattcatgaa aggactttca  1380
aaggccaagg agggagttgt ggctgctgct gagaaaacca acagggtgt ggcagaagca   1440
gcaggaaaga caaagagggg tgttctctat gtaggctcca aaaccaagga gggagtggtg  1500
catggtgtgg caacagtggc tgagaagacc aaagagcaag tgacaaatgt ggaggagca   1560
gtggagggag cagggagcat tgcagcagcc actggctttg tcaaaaagga ccagttgggc  1620
aagaatgaag aaggagcccc acaggaagga attctggaag atatgcctgt ggatcctgac  1680
aatgaggctt atgaaatgcc ttctgaggaa gggtatcaag actacgaacc tgaagcctat  1740
ctcgaggcca ccatgaagat ggacaaaaag actatagttt ggtttagaag agacctaagg  1800
attgaggata atcctgcatt agcagcagct gctcacgaag atctgttttt tcctgtcttc  1860
atttggtgtc ctgaagaaga aggacagttt tatcctggaa gagcttcaag atggtggatg  1920
aaacaatcac ttgctcactt atctcaatcc ttgaaggctc ttggatctga cctcacttta  1980
atcaaaaccc acaacacgat ttcagcgatc ttggattgta tccgcgttac cggtgctaca  2040
aaagtcgtct ttaaccacct ctatgatcct gtttcgttag ttcgggacca taccgtaaag  2100
gagaagctgg tggaacgtgg gatctctgtg caaagctaca atggagatct attgtatgaa  2160
ccgtgggaga tatactgcga aaagggcaaa ccttttacga gtttcaattc ttactggaag  2220
aaatgcttag atatgtcgat tgaatccgtt atgcttcctc ctccttggcg gttgatgcca  2280
ataactgcag cggctgaagc gatttgggcg tgttcgattg aagaactagg ctgagagaat  2340
gaggccgaga aaccgagcaa tgcgttgtta actagagctt ggtctccagg atggagcaat  2400
gctgataagt tactaaatga gttcatcgag aagcagttga tagattatgc aaagaacagc  2460
aagaaagttg ttgggaattc tacttcacta ctttctccgt atctccattt cggggaaata  2520
agcgtcagac acgttttcca gtgtgcccgg atgaaacaaa ttatatgggc aagagataag  2580
aacagtgaag gagaagaaag tgcagatctt tttcttaggg gaatcggttt aagagagtat  2640
tctcggtata tatgtttcaa cttcccgttt actcacgagc aatcgttgtt gagtcatctt  2700
cggttttcc cttgggatgc tgatgttgat aagttcaagg cctggagaca aggcaggacc  2760
ggttatccgt tggtggatgc cggaatgaga gagctttggg ctaccggatg gatgcataac  2820
agaataagag tgattgtttc aagctttgct gtgaagtttc ttctccttcc atggaaatgg  2880
ggaatgaagt atttctggga tacacttttg gatgctgatt tggaatgtga catccttggc  2940
tggcagtata tctctgggag tatccccgat ggccacgagc ttgatcgctt ggacaatccc  3000
gcgttacaag gcgccaaata tgacccagaa ggtgagtaca taaggcaatg gcttcccgag  3060
cttgcgagat tgccaactga atggatccat catccatggg acgctccttt aaccgtactc  3120
aaagcttctg gtgtggaact cggaacaaac tatgcgaaac ccattgtaga catcgacaca  3180
gctcgtgagc tactagctaa agctatttca agaacccgtg agcacagat catgatcgga   3240
```

```
gcagcagccc gggatccacc ggtcgccacc atggtgagca agggcgagga ggataacatg    3300
gccatcatca aggagttcat gcgcttcaag gtgcacatgg agggctccgt gaacggccac    3360
gagttcgaga tcgagggcga gggcgagggc cgcccctacg agggcaccca gaccgccaag    3420
ctgaaggtga ccaagggtgg ccccctgccc ttcgcctggg acatcctgtc ccctcagttc    3480
atgtacggct ccaaggccta cgtgaagcac cccgccgaca tccccgacta cttgaagctg    3540
tccttccccg agggcttcaa gtgggagcgc gtgatgaact tcgaggacgg cggcgtggtg    3600
accgtgaccc aggactcctc cctgcaggac ggcgagttca tctacaaggt gaagctgcgc    3660
ggcaccaact cccctcccga cggccccgta atgcagaaga gaccatgggc tggggaggcc    3720
tcctccgagc ggatgtaccc cgaggacggc gccctgaagg gcgagatcaa gcagaggctg    3780
aagctgaagg acggcggcca ctacgacgct gaggtcaaga ccacctacaa ggccaagaag    3840
cccgtgcagc tgcccggcgc ctacaacgtc aacatcaagt tggacatcac ctcccacaac    3900
gaggactaca ccatcgtgga acagtacgaa cgcgccgagg ccgccactc caccggcggc    3960 atggacgagc tgtacaagta aagcggccgc gactctagag tcgacctgca gaagcttgcc    4020
tcgagcagcg ctgctcgaga gatctacggg tggcatccct gtgacccctc cccagtgcct    4080
ctcctggccc tggaagttgc cactccagtg cccaccagcc ttgtcctaat aaaattaagt    4140
tgcatcattt tgtctgacta ggtgtccttc tataatatta tggggtggag ggggtggta    4200 tggagcaagg gcaagttgg aagacaacc tgtagggcct gcggggtcta ttgggaacca    4260
agctggagtg cagtggcaca atcttggctc actgcaatct ccgcctcctg ggttcaagcg    4320
attctcctgc ctcagcctcc cgagttgttg ggattccagg catgcatgac caggctcagc    4380
taatttttgt ttttttggta gagacggggt ttcaccatat tggccaggct ggtctccaac    4440
tcctaatctc aggtgatcta cccaccttgg cctcccaaat gctgggatt acaggcgtga    4500 accactgctc ccttccctgt ccttctgatt tgtaggtaa ccacgtgcgg accgagcggc    4560
cgcaggaacc cctagtgatg gagttggcca ctccctctct gcgcgctcgc tcgctcactg    4620
aggccgggcg accaaaggtc gcccgacgcc cgggctttgc ccgggcggcc tcagtgagcg    4680
agcgagcgcg cagctgcctg caggggcgcc tgatgcggta ttttctcctt acgcatctgt    4740
gcggtatttc acaccgcata cgtcaaagca accatagtac gcgccctgta gcggcgcatt    4800
aagcgcggcg ggtgtggtgg ttacgcgcag cgtgaccgct acacttgcca gcgccctagc    4860
gcccgctcct ttcgctttct tcccttcctt tctcgccacg ttcgccggct ttccccgtca    4920
agctctaaat cggggctcc ctttagggtt ccgatttagt gctttacggc acctcgaccc    4980
caaaaaactt gatttgggtg atggttcacg tagtgggcca tcgccctgat agacggtttt    5040
tcgccctttg acgttggagt ccacgttctt taatagtgga ctcttgttcc aaactggaac    5100
aacactcaac cctatctcgg ctattctttt gatttataa gggattttgc cgatttcggc    5160
ctattggtta aaaaatgagc tgatttaaca aaaatttaac gcgaatttta caaaatatt    5220 aacgtttaca attttatggt gcactctcag tacaatctgc tctgatgccg catagttaag    5280
ccagccccga cacccgccaa cacccgctga cgcgccctga cgggcttgtc tgctcccggc    5340
atccgcttac agacaagctg tgaccgtctc cgggagctgc atgtgtcaga ggttttcacc    5400
gtcatcaccg aaacgcgcga gacgaaaggg cctcgtgata cgcctatttt tataggttaa    5460
tgtcatgata taatggtttt cttagacgtc aggtggcact tttcggggaa atgtgcgcgg    5520 aaccctatt tgtttatttt tctaaataca ttcaaatatg tatccgctca tgagacaata    5580
accctgataa atgcttcaat aatattgaaa aaggaagagt atgagtattc aacatttccg    5640
```

-continued

```
tgtcgccctt attccctttt ttgcggcatt ttgccttcct gttttgctc acccagaaac      5700 gctggtgaaa gtaaaagatg ctgaagatca gttgggtgca cgagtgggtt acatcgaact      5760
ggatctcaac agcggtaaga tccttgagag ttttcgcccc gaagaacgtt ttccaatgat      5820
gagcactttt aaagttctgc tatgtggcgc ggtattatcc cgtattgacg ccgggcaaga      5880
gcaactcggt cgccgcatac actattctca gaatgacttg gttgagtact caccagtcac      5940 agaaagcat cttacggatg gcatgacagt aagagaatta tgcagtgctg ccataaccat      6000
gagtgataac actgcggcca acttacttct gacaacgatc ggaggaccga aggagctaac      6060
cgcttttttg cacaacatgg gggatcatgt aactcgcctt gatcgttggg aaccggagct      6120
gaatgaagcc ataccaaacg acgagcgtga caccacgatg cctgtagcaa tggcaacaac      6180
gttgcgcaaa ctattaactg gcgaactact tactctagct tcccggcaac aattaataga      6240
ctggatggag gcggataaag ttgcaggacc acttctgcgc tcggcccttc cggctggctg      6300
gtttattgct gataaatctg gagccggtga gcgtgggtct cgcggtatca ttgcagcact      6360
ggggccagat ggtaagccct cccgtatcgt agttatctac acgacgggga gtcaggcaac      6420
tatggatgaa cgaaatagac agatcgctga gataggtgcc tcactgatta gcattggta       6480 actgtcagac caagtttact catatatact ttagattgat ttaaaacttc attttaatt       6540 taaaaggatc taggtgaaga tcctttttga atctcatg accaaaatcc cttaacgtga      6600
gttttcgttc cactgagcgt cagaccccgt agaaaagatc aaaggatctt cttgagatcc      6660
tttttttctg cgcgtaatct gctgcttgca acaaaaaaa ccaccgctac cagcggtggt      6720
ttgtttgccg gatcaagagc taccaactct ttttccgaag gtaactggct tcagcagagc      6780
gcagatacca aatactgtcc ttctagtgta gccgtagtta ggccaccact tcaagaactc      6840
tgtagcaccg cctacatacc tcgctctgct aatcctgtta ccagtggctg ctgccagtgg      6900
cgataagtcg tgtcttaccg ggttggactc aagacgatag ttaccggata aggcgcagcg      6960
gtcgggctga acggggggtt cgtgcacaca gcccagcttg gagcgaacga cctacaccga      7020
actgagatac ctacagcgtg agctatgaga aagcgccacg cttcccgaag ggagaaaggc      7080
ggacaggtat ccggtaagcg gcagggtcgg aacaggagag cgcacgaggg agcttccagg      7140
gggaaacgcc tggtatcttt atagtcctgt cgggtttcgc cacctctgac ttgagcgtcg      7200
atttttgtga tgctcgtcag gggggcggag cctatggaaa aacgccagca acgcggcctt      7260
tttacggttc ctggcctttt gctggccttt tgctcacatg t                         7301
```

<210> SEQ ID NO 4
<211> LENGTH: 6188
<212> TYPE: DNA
<213> ORGANISM: Artificial Sequence
<220> FEATURE:
<223> OTHER INFORMATION: pmCherryN1-LIPA-Empty
<220> FEATURE:
<221> NAME/KEY: misc_feature
<222> LOCATION: (625)..(2118)
<223> OTHER INFORMATION: Arabidopsis thaliana cryptochrome 2 (CRY2)

<400> SEQUENCE: 4

```
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
```

```
aagtacgccc cctattgacg tcaatgacgg taaatggccc gcctggcatt atgcccagta    300
catgacccta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgc cccattgacg caaatgggcg gtaggcgtgt     540
acggtgggag gtctatataa gcagagctgg tttagtgaac cgtcagatcc gctagcgcta    600
ccggactcag atctcgaggc caccatgaag atggacaaaa agactatagt ttggtttaga    660
agagacctaa ggattgagga taatcctgca ttagcagcag ctgctcacga aggatctgtt    720
tttcctgtct tcatttggtg tcctgaagaa gaaggacagt tttatcctgg aagagcttca    780
agatggtgga tgaaacaatc acttgctcac ttatctcaat ccttgaaggc tcttggatct    840
gacctcactt taatcaaaac ccacaacacg atttcagcga tcttggattg tatccgcgtt    900
accggtgcta caaagtcgt ctttaaccac ctctatgatc ctgtttcgtt agttcgggac      960 catacccgtaa aggagaagct ggtggaacgt gggatctctg tgcaaagcta caatggagat   1020
ctattgtatg aaccgtggga gatatactgc gaaaagggca aacctttac gagtttcaat     1080 tcttactgga agaaatgctt agatatgtcg attgaatccg ttatgcttcc tcctccttgg    1140
cggttgatgc caataactgc agcggctgaa gcgatttggg cgtgttcgat gaagaacta     1200 gggctggaga atgaggccga gaaaccgagc aatgcgttgt taactagagc ttggtctcca    1260
ggatggagca atgctgataa gttactaaat gagttcatcg agaagcagtt gatagattat    1320
gcaaagaaca gcaagaaagt tgttgggaat tctacttcac tactttctcc gtatctccat    1380
ttcggggaaa taagcgtcag acacgttttc cagtgtgccc ggatgaaaca aattatatgg    1440
gcaagagata agaacagtga aggagaagaa agtgcagatc ttttctcttag ggaatcggt    1500 ttaagagagt attctcggta tatatgtttc aacttcccgt ttactcacga gcaatcgttg    1560
ttgagtcatc ttcggttttt cccttgggat gctgatgttg ataagttcaa ggcctggaga    1620
caaggcagga ccggttatcc gttggtggat gccggaatga gagagctttg gctaccgga     1680 tggatgcata acagaataag agtgattgtt tcaagctttg ctgtgaagtt tcttctcctt    1740
ccatggaaat ggggaatgaa gtatttctgg gatacacttt tggatgctga tttggaatgt    1800
gacatccttg gctggcagta tatctctggg agtatccccg atggccacga gcttgatcgc    1860
ttggacaatc ccgcgttaca aggcgccaaa tatgacccag aaggtgagta cataaggcaa    1920
tggcttcccg agcttgcgag attgccaact gaatggatcc atcatccatg ggacgctcct    1980
ttaaccgtac tcaaagcttc tggtgtggaa ctcggaacaa actatgcgaa acccattgta    2040
gacatcgaca cagctcgtga gctactagct aaagctattt caagaacccg tggagcacag    2100
atcatgatcg gagcagcagc ccgggatcca ccggtcgcca ccatggtgag caagggcgag    2160
gaggataaca tggccatcat caaggagttc atgcgcttca aggtgcacat ggagggctcc    2220
gtgaacggcc acgagttcga gatcgagggc gagggcgagg ccgcccccta cgagggcacc    2280
cagaccgcca gctgaaggt gaccaagggt ggccccctgc ccttcgcctg gacatcctg      2340 tcccctcagt tcatgtacgg ctccaaggcc tacgtgaagc accccgccga catccccgac    2400
tacttgaagc tgtccttccc cgagggcttc aagtgggagc gcgtgatgaa cttcgaggac    2460
ggcggcgtgg tgaccgtgac ccaggactcc tccctgcagg acggcgagtt catctacaag    2520
gtgaagctgc gcggcaccaa cttccccctcc gacggccccg taatgcagaa gaagaccatg    2580
ggctgggagg cctcctccga gcggatgtac cccgaggacg gcgccctgaa gggcgagatc    2640
```

```
aagcagaggc tgaagctgaa ggacggcggc cactacgacg ctgaggtcaa gaccacctac    2700
aaggccaaga agcccgtgca gctgcccggc gcctacaact caacatcaa gttggacatc     2760 acctcccaca acgaggacta caccatcgtg aacagtacg aacgcgccga gggccgccac    2820
tccaccggcg gcatggacga gctgtacaag taaagcggcc gcgactctag atcataatca    2880
gccataccac atttgtagag gttttacttg ctttaaaaaa cctcccacac ctccccctga    2940
acctgaaaca taaaatgaat gcaattgttg ttgttaactt gtttattgca gcttataatg    3000
gttacaaata aagcaatagc atcacaaatt tcacaaataa agcatttttt tcactgcatt    3060
ctagttgtgg tttgtccaaa ctcatcaatg tatcttaagg cgtaaattgt aagcgttaat    3120
attttgttaa aattcgcgtt aaattttgt taaatcagct cattttttaa ccaataggcc     3180
gaaatcggca aaatccctta taaatcaaaa gaatagaccg agatagggtt gagtgttgtt    3240
ccagtttgga acaagagtcc actattaaag aacgtggact ccaacgtcaa agggcgaaaa    3300
accgtctatc agggcgatgg cccactacgt gaaccatcac cctaatcaag ttttttgggg   3360
tcgaggtgcc gtaaagcact aaatcggaac cctaaaggga gcccccgatt tagagcttga    3420
cggggaaagc cggcgaacgt ggcgagaaag gaagggaaga agcgaaagg agcgggcgct     3480 agggcgctgg caagtgtagc ggtcacgctg cgcgtaacca ccacacccgc cgcgcttaat    3540
gcgccgctac agggcgcgtc aggtggcact tttcggggaa atgtgcgcgg aacccctatt    3600
tgtttatttt tctaaataca ttcaaatatg tatccgctca tgagacaata accctgataa    3660
atgcttcaat aatattgaaa aaggaagagt cctgaggcgg aaagaaccag ctgtggaatg    3720
tgtgtcagtt agggtgtgga agtccccag gctccccagc aggcagaagt atgcaaagca     3780
tgcatctcaa ttagtcagca accaggtgtg gaaagtcccc aggctcccca gcaggcagaa    3840
gtatgcaaag catgcatctc aattagtcag caaccatagt cccgccccta actccgccca    3900
tcccgcccct aactccgccc agttccgccc attctccgcc ccatggctga ctaattttt     3960 ttatttatgc agaggccgag gccgcctcgg cctctgagct attccagaag tagtgaggag    4020
gcttttttgg aggcctaggc ttttgcaaag atcgatcaag agacaggatg aggatcgttt    4080
cgcatgattg aacaagatgg attgcacgca ggttctccgg ccgcttgggt ggagaggcta    4140
ttcggctatg actgggcaca acagacaatc ggctgctctg atgccgccgt gttccggctg    4200
tcagcgcagg ggcgcccggt tctttttgtc aagaccgacc tgtccggtgc cctgaatgaa    4260
ctgcaagacg aggcagcgcg gctatcgtgg ctggccacga cgggcgttcc ttgcgcagct    4320
gtgctcgacg ttgtcactga agcgggaagg gactggctgc tattgggcga agtgccgggg    4380
caggatctcc tgtcatctca ccttgctcct gccgagaaag tatccatcat ggctgatgca    4440
atgcggcggc tgcatacgct tgatccggct acctgcccat tcgaccacca agcgaaacat    4500
cgcatcgagc gagcacgtac tcggatggaa gccggtcttg tcgatcagga tgatctggac    4560
gaagagcatc aggggctcgc gccagccgaa ctgttcgcca ggctcaaggc gagcatgccc    4620
gacggcgagg atctcgtcgt gacccatggc gatgcctgct tgccgaatat catggtggaa    4680
aatggccgct ttctggatt catcgactgt ggccggctgg gtgtggcgga ccgctatcag    4740
gacatagcgt tggctacccg tgatattgct gaagagcttg gcggcgaatg ggctgaccgc    4800
ttcctcgtgc tttacggtat cgccgctccc gattcgcagc gcatcgcctt ctatcgcctt    4860
cttgacgagt tcttctgagc gggactctgg ggttcgaaat gaccgaccaa gcgacgccca    4920
acctgccatc acgagatttc gattccaccg ccgccttcta tgaaaggttg gcttcggaa     4980
```

-continued

| | |
|---|---|
| tcgttttccg ggacgccggc tggatgatcc tccagcgcgg ggatctcatg ctggagttct | 5040 |
| tcgcccaccc tagggggagg ctaactgaaa cacggaagga gacaataccg gaaggaaccc | 5100 |
| gcgctatgac ggcaataaaa agacagaata aaacgcacgg tgttgggtcg tttgttcata | 5160 |
| aacgcgggt tcggtcccag ggctggcact ctgtcgatac cccaccgaga ccccattggg | 5220 |
| gccaatacgc ccgcgtttct ccttttccc caccccaccc ccaagttcg ggtgaaggcc | 5280 |
| cagggctcgc agccaacgtc ggggcggcag gccctgccat agcctcaggt tactcatata | 5340 |
| tactttagat tgatttaaaa cttcattttt aatttaaaag gatctaggtg aagatccttt | 5400 |
| ttgataatct catgaccaaa atcccttaac gtgagttttc gttccactga gcgtcagacc | 5460 |
| ccgtagaaaa gatcaaagga tcttcttgag atccttttt tctgcgcgta atctgctgct | 5520 |
| tgcaaacaaa aaaaccaccg ctaccagcgg tggtttgttt gccggatcaa gagctaccaa | 5580 |
| ctctttttcc gaaggtaact ggcttcagca gagcgcagat accaaatact gtccttctag | 5640 |
| tgtagccgta gttaggccac cacttcaaga actctgtagc accgcctaca tacctcgctc | 5700 |
| tgctaatcct gttaccagtg gctgctgcca gtggcgataa gtcgtgtctt accgggttgg | 5760 |
| actcaagacg atagttaccg gataaggcgc agcggtcggg ctgaacgggg ggttcgtgca | 5820 |
| cacagcccag cttggagcga acgacctaca ccgaactgag atacctacag cgtgagctat | 5880 |
| gagaaagcgc cacgcttccc gaagggagaa aggcggacag gtatccggta agcggcaggg | 5940 |
| tcggaacagg agagcgcacg agggagcttc caggggggaaa cgcctggtat ctttatagtc | 6000 |
| ctgtcgggtt tcgccacctc tgacttgagc gtcgattttt gtgatgctcg tcaggggggc | 6060 |
| ggagcctatg gaaaaacgcc agcaacgcgg ccttttttacg gttcctggcc ttttgctggc | 6120 |
| cttttgctca catgttcttt cctgcgttat cccctgattc tgtggataac cgtattaccg | 6180 |
| ccatgcat | 6188 |

```
<210> SEQ ID NO 5
<211> LENGTH: 6659
<212> TYPE: DNA
<213> ORGANISM: Artificial Sequence
<220> FEATURE:
<223> OTHER INFORMATION: pmCherry-LIPA-alpha-syn
<220> FEATURE:
<221> NAME/KEY: misc_feature
<222> LOCATION: (1096)..(2589)
<223> OTHER INFORMATION: Arabidopsis thaliana cryptochrome 2 (CRY2)

<400> SEQUENCE: 5
```

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta acaactccgc cccattgacg caaatgggcg taggcgtgt | 540 |
| acggtgggag gtctatataa gcagagctgg tttagtgaac cgtcagatcc gctagcgcta | 600 |
| ccggactcag atctcgagga cagtgtggtg taaaggaatt cattagccat ggatgtattc | 660 |
| atgaaaggac tttcaaaggc caaggaggga gttgtggctg ctgctgagaa aaccaaacag | 720 |

```
ggtgtggcag aagcagcagg aaagacaaaa gagggtgttc tctatgtagg ctccaaaacc    780
aaggagggag tggtgcatgg tgtggcaaca gtggctgaga agaccaaaga gcaagtgaca    840
aatgttggag gagcagtggt gacgggtgtg acagcagtag cccagaagac agtggaggga    900
gcagggagca ttgcagcagc cactggcttt gtcaaaaagg accagttggg caagaatgaa    960
gaaggagccc cacaggaagg aattctggaa gatatgcctg tggatcctga caatgaggct   1020
tatgaaatgc cttctgagga agggtatcaa gactacgaac ctgaagccgg taccgcgggc   1080
ccggtcgagg ccaccatgaa gatggacaaa aagactatag tttggtttag aagagaccta   1140
aggattgagg ataatcctgc attagcagca gctgctcacg aaggatctgt ttttcctgtc   1200
ttcatttggt gtcctgaaga agaaggacag ttttatcctg aagagcttc aagatggtgg    1260 atgaaacaat cacttgctca cttatctcaa tccttgaagg ctcttggatc tgacctcact   1320
ttaatcaaaa cccacaacac gatttcagcg atcttggatt gtatccgcgt taccggtgct   1380
acaaaagtcg tctttaacca cctctatgat cctgtttcgt tagttcggga ccataccgta   1440
aaggagaagc tggtggaacg tgggatctct gtgcaaagct acaatggaga tctattgtat   1500
gaaccgtggg agatatactg cgaaaagggc aaacctttta cgagtttcaa ttcttactgg   1560
aagaaatgct tagatatgtc gattgaatcc gttatgcttc ctcctccttg gcggttgatg   1620
ccaataactg cagcggctga agcgatttgg gcgtgttcga ttgaagaact agggctggag   1680
aatgaggccg agaaaccgag caatgcgttg ttaactagag cttggtctcc aggatggagc   1740
aatgctgata agttactaaa tgagttcatc gagaagcagt tgatagatta tgcaaagaac   1800
agcaagaaag ttgttgggaa ttctacttca ctactttctc cgtatctcca tttcggggaa   1860
ataagcgtca gacacgtttt ccagtgtgcc cggatgaaac aaattatatg gcaagagat    1920 aagaacagtg aaggagaaga aagtgcagat cttttctta ggggaatcgg tttaagagag    1980
tattctcggt atatatgttt caacttcccg tttactcacg agcaatcgtt gttgagtcat   2040
cttcggtttt tcccttggga tgctgatgtt gataagttca aggcctggag acaaggcagg   2100
accggttatc cgttggtgga tgccggaatg agagagcttt gggctaccgg atggatgcat   2160
aacagaataa gagtgattgt ttcaagcttt gctgtgaagt ttcttctcct tccatggaaa   2220
tggggaatga agtatttctg ggatacactt ttggatgctg atttggaatg tgacatcctt   2280
ggctggcagt atatctctgg gagtatcccc gatggccacg agcttgatcg cttggacaat   2340
cccgcgttac aaggcgccaa atatgaccca gaaggtgagt acataaggca atggcttccc   2400
gagcttgcga gattgccaac tgaatggatc catcatccat gggacgctcc tttaaccgta   2460
ctcaaagctt ctggtgtgga actcggaaca aactatgcga aacccattgt agacatcgac   2520
acagctcgtg agctactagc taaagctatt tcaagaaccc gtggagcaca gatcatgatc   2580
ggagcagcag cccgggatcc accggtcgcc accatggtga gcaagggcga ggaggataac   2640
atggccatca tcaaggagtt catgcgcttc aaggtgcaca tggagggctc cgtgaacggc   2700
cacgagttcg agatcgaggg cgagggcgag ggccgcccct acgagggcac ccagaccgcc   2760
aagctgaagg tgaccaaggg tggccccctg cccttcgcct gggacatcct gtcccctcag   2820
ttcatgtacg gctccaaggc ctacgtgaag caccccgccg catccccgga ctacttgaag   2880
ctgtccttcc ccgagggctt caagtgggag cgcgtgatga acttcgagga cggcggcgtg   2940
gtgaccgtga cccaggactc ctccctgcag gacggcgagt tcatctacaa ggtgaagctg   3000
cgcggcacca acttcccctc cgacggcccc gtaatgcaga agaagaccat gggctgggag   3060
```

```
gcctcctccg agcggatgta ccccgaggac ggcgccctga agggcgagat caagcagagg    3120
ctgaagctga aggacggcgg ccactacgac gctgaggtca agaccaccta caaggccaag    3180
aagcccgtgc agctgcccgg cgcctacaac gtcaacatca gttggacat cacctcccac    3240 aacgaggact acaccatcgt ggaacagtac gaacgcgccg agggccgcca ctccaccggc    3300
ggcatggacg agctgtacaa gtaaagcggc cgcgactcta gatcataatc agccatacca    3360
catttgtaga ggttttactt gctttaaaaa acctcccaca cctcccctg aacctgaaac    3420 ataaaatgaa tgcaattgtt gttgttaact tgtttattgc agcttataat ggttacaaat    3480
aaagcaatag catcacaaat ttcacaaata aagcatttt ttcactgcat tctagttgtg    3540
gtttgtccaa actcatcaat gtatcttaag gcgtaaattg taagcgttaa tattttgtta    3600
aaattcgcgt taaattttg ttaaatcagc tcatttttta accataggc cgaaatcggc    3660 aaaatccctt ataaatcaaa agaatagacc gagatagggt tgagtgttgt tccagtttgg    3720
aacaagagtc cactattaaa gaacgtggac tccaacgtca aagggcgaaa aaccgtctat    3780
cagggcgatg gcccactacg tgaaccatca ccctaatcaa gttttttggg gtcgaggtgc    3840
cgtaaagcac taaatcggaa ccctaaaggg agccccgat ttagagcttg acggggaaag    3900
ccggcgaacg tggcgagaaa ggaagggaag aaagcgaaag gagcgggcgc tagggcgctg    3960
gcaagtgtag cggtcacgct gcgcgtaacc accacccg ccgcgcttaa tgcgccgcta    4020
cagggcgcgt caggtggcac ttttcgggga atgtgcgcg gaaccctat ttgtttattt    4080 ttctaaatac attcaaatat gtatccgctc atgagacaat aaccctgata atgcttcaa    4140 taatattgaa aaggaagag tcctgaggcg gaaagaacca gctgtggaat gtgtgtcagt    4200
tagggtgtgg aaagtcccca ggctccccag caggcagaag tatgcaaagc atgcatctca    4260
attagtcagc aaccaggtgt ggaaagtccc caggctcccc agcaggcaga agtatgcaaa    4320
gcatgcatct caattagtca gcaaccatag tcccgcccct aactccgccc atcccgcccc    4380
taactccgcc cagttccgcc cattctccgc cccatggctg actaattttt tttatttatg    4440
cagaggccga ggccgcctcg gcctctgagc tattccagaa gtagtgagga ggcttttttg    4500
gaggcctagg cttttgcaaa gatcgatcaa gagacaggat gaggatcgtt tcgcatgatt    4560
gaacaagatg gattgcacgc aggttctccg gccgcttggg tggagaggct attcggctat    4620
gactgggcac aacagacaat cggctgctct gatgccgccg tgttccggct gtcagcgcag    4680
gggcgcccgg ttcttttgt caagaccgac ctgtccggtg ccctgaatga actgcaagac    4740
gaggcagcgc ggctatcgtg gctggccacg acgggcgttc cttgcgcagc tgtgctcgac    4800
gttgtcactg aagcgggaag ggactggctg ctattgggcg aagtgccggg gcaggatctc    4860
ctgtcatctc accttgctcc tgccgagaaa gtatccatca tggctgatgc aatgcggcgg    4920
ctgcatacgc ttgatccggc tacctgccca ttcgaccacc aagcgaaaca tcgcatcgag    4980
cgagcacgta ctcggatgga agccggtctt gtcgatcagg atgatctgga cgaagagcat    5040
caggggctcg cgccagccga actgttcgcc aggctcaagg cgagcatgcc cgacggcgag    5100
gatctcgtcg tgacccatgg cgatgcctgc ttgccgaata tcatggtgga aaatggccgc    5160
ttttctggat tcatcgactg tggccggctg ggtgtggcgg accgctatca ggacatagcg    5220
ttggctaccc gtgatattgc tgaagagctt ggcggcgaat gggctgaccg cttcctcgtg    5280
ctttacggta tcgccgctcc cgattcgcag cgcatcgcct tctatcgcct tcttgacgag    5340
ttcttctgag cgggactctg gggttcgaaa tgaccgacca agcgacgccc aacctgccat    5400
cacgagattt cgattccacc gccgccttct atgaaaggtt gggcttcgga atcgttttcc    5460
```

```
gggacgccgg ctggatgatc ctccagcgcg gggatctcat gctggagttc ttcgcccacc   5520 ctaggggag gctaactgaa acacggaagg agacaatacc ggaaggaacc cgcgctatga     5580
cggcaataaa aagacagaat aaaacgcacg tgttgggtc gtttgttcat aaacgcgggg     5640
ttcggtccca gggctggcac tctgtcgata ccccaccgag accccattgg ggccaatacg    5700
cccgcgtttc ttccttttcc ccaccccacc cccaagttc gggtgaaggc ccagggctcg     5760
cagccaacgt cggggcggca ggccctgcca tagcctcagg ttactcatat atactttaga    5820
ttgatttaaa acttcatttt taatttaaaa ggatctaggt gaagatcctt tttgataatc    5880
tcatgaccaa aatcccttaa cgtgagtttt cgttccactg agcgtcagac cccgtagaaa    5940
agatcaaagg atcttcttga tccttttt tctgcgcgt aatctgctgc ttgcaaacaa       6000
aaaaaccacc gctaccagcg gtggtttgtt tgccggatca agagctacca actcttttc     6060 cgaaggtaac tggcttcagc agagcgcaga taccaaatac tgtccttcta gtgtagccgt   6120
agttaggcca ccacttcaag aactctgtag caccgcctac atacctcgct ctgctaatcc    6180
tgttaccagt ggctgctgcc agtggcgata gtcgtgtct taccggggttg gactcaagac    6240 gatagttacc ggataaggcg cagcggtcgg gctgaacggg gggttcgtgc acacagccca    6300
gcttggagcg aacgacctac accgaactga gatacctaca gcgtgagcta tgagaaagcg    6360
ccacgcttcc cgaagggaga aaggcggaca ggtatccggt aagcggcagg gtcggaacag    6420
gagagcgcac gagggagctt ccaggggga acgcctggta tctttatagt cctgtcgggt    6480
ttcgccacct ctgacttgag cgtcgatttt tgtgatgctc gtcagggggg cggagcctat    6540
ggaaaaacgc cagcaacgcg gccttttac ggttcctggc cttttgctgg cctttgctc      6600 acatgttctt cctgcgtta tcccctgatt ctgtggataa ccgtattacc gccatgcat     6659
```

<210> SEQ ID NO 6
<211> LENGTH: 6564
<212> TYPE: DNA
<213> ORGANISM: Artificial Sequence
<220> FEATURE:
<223> OTHER INFORMATION: pmCherry-LIPA-alpha-syn-deltaNAC
<220> FEATURE:
<221> NAME/KEY: misc_feature
<222> LOCATION: (1001)..(2494)
<223> OTHER INFORMATION: Arabidopsis thaliana cryptochrome 2 (CRY2)

<400> SEQUENCE: 6

```
tagttattaa tagtaatcaa ttacggggtc attagttcat agcccatata tggagttccg    60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcccac    600
catggatgta ttcatgaaag gactttcaaa ggccaaggag ggagttgtgg ctgctgctga    660
gaaaaccaaa cagggtgtgg cagaagcagc aggaaagaca aagagggtg ttctctatgt     720
```

```
aggctccaaa accaaggagg gagtggtgca tggtgtggca acagtggctg agaagaccaa    780
agagcaagtg acaaatgttg gaggagcagt ggagggagca gggagcattg cagcagccac    840
tggctttgtc aaaaaggacc agttgggcaa gaatgaagaa ggagccccac aggaaggaat    900
tctggaagat atgcctgtgg atcctgacaa tgaggcttat gaaatgcctt ctgaggaagg    960
gtatcaagac tacgaacctg aagcctatct cgaggccacc atgaagatgg acaaaaagac   1020
tatagtttgg tttagaagag acctaaggat tgaggataat cctgcattag cagcagctgc   1080
tcacgaagga tctgttttc ctgtcttcat ttggtgtcct gaagaagaag acagttttta    1140
tcctggaaga gcttcaagat ggtggatgaa acaatcactt gctcacttat ctcaatcctt   1200
gaaggctctt ggatctgacc tcactttaat caaaacccac aacacgattt cagcgatctt   1260
ggattgtatc cgcgttaccg gtgctacaaa agtcgtcttt aaccacctct atgatcctgt   1320
ttcgttagtt cgggaccata ccgtaaagga gaagctggtg aacgtgggga tctctgtgca   1380
aagctacaat ggagatctat tgtatgaacc gtgggagata tactgcgaaa agggcaaacc   1440
ttttacgagt ttcaattctt actggaagaa atgcttagat atgtcgattg aatccgttat   1500
gcttcctcct ccttggcggt tgatgccaat aactgcagcg gctgaagcga tttgggcgtg   1560
ttcgattgaa gaactagggc tggagaatga ggccgagaaa ccgagcaatg cgttgttaac   1620
tagagcttgg tctccaggat ggagcaatgc tgataagtta ctaaatgagt tcatcgagaa   1680
gcagttgata gattatgcaa agaacagcaa gaaagttgtt gggaattcta cttcactact   1740
ttctccgtat ctccatttcg gggaaataag cgtcagacac gttttccagt gtgcccggat   1800
gaaacaaatt atatgggcaa gagataagaa cagtgaagga gaagaaagtg cagatctttt   1860
tcttagggga atcggtttaa gagagtattc tcggtatata tgtttcaact tcccgtttac   1920
tcacgagcaa tcgttgttga gtcatcttcg gttttttccct tgggatgctg atgttgataa   1980
gttcaaggcc tggagacaag gcaggaccgg ttatccgttg gtggatgccg aatgagagaa   2040
gctttgggct accggatgga tgcataacag aataagagtg attgtttcaa gctttgctgt   2100
gaagtttctt ctccttccat ggaaatgggg aatgaagtat ttctgggata cattttggaa   2160
tgctgatttg aatgtgaca tccttggctg gcagtatatc tctgggagta tccccgatgg   2220
ccacgagctt gatcgcttgg acaatcccgc gttacaaggc gccaaatatg acccagaagg   2280
tgagtacata aggcaatggc ttcccgagct gcgagattg ccaactgaat ggatccatca   2340
tccatgggac gctccttaa ccgtactcaa agcttctggt gtggaactcg gaacaaacta   2400
tgcgaaaccc attgtagaca tcgacacagc tcgtgagcta ctagctaaag ctatttcaag   2460
aacccgtgga gcacagatca tgatcggagc agcagcccgg gatccaccgg tcgccaccat   2520
ggtgagcaag ggcgaggagg ataacatggc catcatcaag gagttcatgc gcttcaaggt   2580
gcacatggag ggctccgtga acggccacga gttcgagatc gagggcgagg cgagggccg   2640
cccctacgag ggcacccaga ccgccaagct gaaggtgacc aagggtggcc ccctgccctt   2700
cgcctgggac atcctgtccc ctcagttcat gtacggctcc aaggcctacg tgaagcaccc   2760
cgccgacatc cccgactact tgaagctgtc cttccccgag ggcttcaagt gggagcgcgt   2820
gatgaacttc gaggacggcg gcgtggtgac cgtgacccag gactcctccc tgcaggacgg   2880
cgagttcatc tacaaggtga agctgcgcgg caccaacttc ccctccgacg gccccgtaat   2940
gcagaagaag accatgggct gggaggcctc ctccgagcgg atgtacccg aggacggcgc   3000
cctgaagggc gagatcaagc agaggctgaa gctgaaggac ggcggccact acgacgctga   3060
ggtcaagacc acctacaagg ccaagaagcc cgtgcagctg cccggcgcct acaacgtcaa   3120
```

```
catcaagttg gacatcacct cccacaacga ggactacacc atcgtggaac agtacgaacg   3180
cgccgagggc cgccactcca ccggcggcat ggacgagctg tacaagtaaa gcggccgcga   3240
ctctagatca taatcagcca taccacattt gtagaggttt tacttgcttt aaaaaacctc   3300
ccacacctcc ccctgaacct gaaacataaa atgaatgcaa ttgttgttgt taacttgttt   3360
attgcagctt ataatggtta caaataaagc aatagcatca caaatttcac aaataaagca   3420 ttttttttcac tgcattctag ttgtggtttg tccaaactca tcaatgtatc ttaaggcgta   3480
aattgtaagc gttaatattt tgttaaaatt cgcgttaaat ttttgttaaa tcagctcatt   3540
ttttaaccaa taggccgaaa tcggcaaaat cccttataaa tcaaaagaat agaccgagat   3600
agggttgagt gttgttccag tttggaacaa gagtccacta ttaaagaacg tggactccaa   3660
cgtcaaaggg cgaaaaaccg tctatcaggg cgatggccca ctacgtgaac catcacccta   3720
atcaagtttt tggggtcga ggtgccgtaa agcactaaat cggaaccctaa agggagccc    3780 ccgatttaga gcttgacggg gaaagccggc gaacgtggcg agaaaggaag gaagaaagc    3840 gaaaggagcg ggcgctaggg cgctggcaag tgtagcggtc acgctgcgcg taaccaccac   3900
acccgccgcg cttaatgcgc cgctacaggg cgcgtcaggt ggcactttc ggggaaatgt    3960 gcgcggaacc cctatttgtt tattttttcta aatacattca aatatgtatc cgctcatgag   4020
acaataaccc tgataaatgc ttcaataata ttgaaaaagg aagagtcctg aggcggaaag   4080
aaccagctgt ggaatgtgtg tcagttaggg tgtggaaagt ccccaggctc cccagcaggc   4140
agaagtatgc aaagcatgca tctcaattag tcagcaacca ggtgtggaaa gtccccaggc   4200
tccccagcag gcagaagtat gcaaagcatg catctcaatt agtcagcaac catagtcccg   4260
cccctaactc cgcccatccc gcccctaact ccgcccagtt ccgcccattc tccgccccat   4320
ggctgactaa ttttttttat ttatgcagag gccgaggccg cctcggcctc tgagctattc   4380
cagaagtagt gaggaggctt ttttggaggc ctaggctttt gcaaagatcg atcaagagac   4440
aggatgagga tcgtttcgca tgattgaaca agatggattg cacgcaggtt ctccggccgc   4500
ttgggtggag aggctattcg gctatgactg ggcacaacag acaatcggct gctctgatgc   4560
cgccgtgttc cggctgtcag cgcaggggcg cccggttctt tttgtcaaga ccgacctgtc   4620
cggtgccctg aatgaactgc aagacgaggc agcgcggcta tcgtggctgg ccacgacggg   4680
cgttccttgc gcagctgtgc tcgacgttgt cactgaagcg ggaagggact ggctgctatt   4740
gggcgaagtg ccggggcagg atctcctgtc atctcacctt gctcctgccg agaaagtatc   4800
catcatggct gatgcaatgc ggcggctgca tacgcttgat ccggctacct gcccattcga   4860
ccaccaagcg aaacatcgca tcgagcgagc acgtactcgg atggaagccg gtcttgtcga   4920
tcaggatgat ctggacgaag agcatcaggg gctcgcgcca gccgaactgt tcgccaggct   4980
caaggcgagc atgcccgacg gcgaggatct cgtcgtgacc catggcgatg cctgcttgcc   5040
gaatatcatg gtgaaaatg gccgcttttc tggattcatc gactgtggcc ggctgggtgt    5100
ggcggaccgc tatcaggaca tagcgttggc tacccgtgat attgctgaag agcttggcgg   5160
cgaatgggct gaccgcttcc tcgtgcttta cggtatcgcc gctcccgatt cgcagcgcat   5220
cgccttctat cgccttcttg acgagttctt ctgagcggga ctctgggtt cgaaatgacc    5280 gaccaagcga cgcccaacct gccatcacga gatttcgatt ccaccgccgc cttctatgaa   5340
aggttgggct tcggaatcgt tttccgggac gccggctgga tgatcctcca gcgcgggat    5400 ctcatgctgg agttcttcgc ccaccctagg gggaggctaa ctgaaacacg gaaggagaca   5460
```

```
ataccggaag gaacccgcgc tatgacggca ataaaaagac agaataaaac gcacggtgtt    5520
gggtcgtttg ttcataaacg cggggttcgg tcccagggct ggcactctgt cgataccccca   5580 ccgagacccc attggggcca atacgcccgc gtttcttcct tttccccacc ccaccccca    5640 agttcgggtg aaggcccagg gctcgcagcc aacgtcgggg cggcaggccc tgccatagcc    5700
tcaggttact catatatact ttagattgat ttaaaacttc atttttaatt taaaaggatc    5760
taggtgaaga tcctttttga taatctcatg accaaaatcc cttaacgtga gttttcgttc    5820
cactgagcgt cagacccgt agaaaagatc aaaggatctt cttgagatcc ttttttctg     5880 cgcgtaatct gctgcttgca aacaaaaaaa ccaccgctac cagcggtggt ttgtttgccg    5940
gatcaagagc taccaactct ttttccgaag gtaactggct tcagcagagc gcagatacca    6000
aatactgtcc ttctagtgta gccgtagtta ggccaccact tcaagaactc tgtagcaccg    6060
cctacatacc tcgctctgct aatcctgtta ccagtggctg ctgccagtgg cgataagtcg    6120
tgtcttaccg ggttggactc aagacgatag ttaccggata aggcgcagcg gtcgggctga    6180 acgggggggtt cgtgcacaca gcccagcttg gagcgaacga cctacaccga actgagatac    6240
ctacagcgtg agctatgaga aagcgccacg cttcccgaag ggagaaaggc ggacaggtat    6300
ccggtaagcg gcagggtcgg aacaggagag cgcacgaggg agcttccagg gggaaacgcc    6360
tggtatcttt atagtcctgt cgggtttcgc cacctctgac ttgagcgtcg attttttgtga   6420 tgctcgtcag gggggcggag cctatggaaa aacgccagca acgcggcctt tttacggttc    6480 ctggccttt gctggccttt tgctcacatg ttctttcctg cgttatcccc tgattctgtg    6540
gataaccgta ttaccgccat gcat                                           6564
```

LIGHT-INDUCIBLE PROTEIN AGGREGATION SYSTEM FOR MODELING PROTEINOPATHIES AND NEURODEGENERATIVE DISORDERS

CROSS-REFERENCE TO RELATED APPLICATIONS

This application is a national stage entry of International Application Number PCT/CA2019/050914 filed Jul. 3, 2019, which claims priority to U.S. Provisional Application No. 62/693,666 filed Jul. 3, 2018.

TECHNICAL FIELD

The present description relates to optobiology. More specifically, the present description relates to a light-inducible protein aggregation system for modeling proteinopathies and neurodegenerative disorders.

BACKGROUND

Protein aggregation is a process by which misfolded proteins generally adopt an organized and structurally well-defined fibrillar conformation, often leading to the formation of proteinaceous amyloid deposits. A typical example is the accumulation of proteinaceous intraneuronal inclusions, called Lewy bodies (LB), in the brain of patients suffering from alpha-synucleinopathies, a group of neurological disorders which encompasses Parkinson's disease (PD), PD with dementia (PDD), dementia with Lewy bodies (DLB), and multiple system atrophy (MSA).

Since their initial description more than a century ago, a causal link between LB formation and neurotoxicity in PD and other proteopathic disorders has been suggested. However, the exact role of LB in the pathogenesis and progression of disease and how these aggregates precipitate neuronal death remains uncertain. This is in part due to the fact that current cellular and animal models of PD do not allow to monitor the aggregation process in living cells and do not result in the formation of intraneuronal inclusions resembling authentic LB observed in the brains of PD disease patients. Thus, there remains a need for improved systems for modeling proteinopathies and neurodegenerative disorders.

SUMMARY

The present invention generally relates to a versatile light-inducible intracellular protein aggregation system (LIPA) useful for modeling proteinopathies and neurodegenerative disorders, such as in real-time in living cells, in a spatiotemporal controlled manner.

In some aspects, the LIPA system may comprise a cell expressing an alpha-synuclein (α-syn) polypeptide or another proteopathic polypeptide that self-aggregates under pathogenic conditions, operably linked to a photoactivatable polypeptide, wherein illumination (light stimulation) of the photoactivatable polypeptide with light having a wavelength sufficient for photoactivation triggers irreversible accumulation of intracellular protein aggregates comprising the alpha-synuclein polypeptide or proteopathic polypeptide.

In some embodiments, the intracellular protein aggregates accumulate rapidly and in real-time during the illumination, thereby enabling spatiotemporal control of protein aggregation. Furthermore, in some embodiments, the intracellular protein aggregates comprise misfolded proteins in beta-sheet conformation that may remain stable for days following cessation of light stimulation. In some embodiments, the intracellular protein aggregates may have a morphology different from that of intracellular inclusions formed following photoactivation of the photoactivatable polypeptide in the absence of the alpha-synuclein polypeptide or other proteopathic polypeptide.

In some embodiments, the photoactivatable polypeptide and the alpha-synuclein or other proteopathic polypeptide may be comprised in a fusion protein, and/or further fused to a detectable marker enabling real-time detection in vivo (e.g., a fluorescent protein).

In some embodiments, the proteopathic polypeptide is or comprises a polypeptide that, upon self-aggregation, adopts a misfolded conformation rich in beta-sheet structure and/or exhibits seeding activity. In some embodiments, the proteopathic polypeptide is, comprises, or is from: an Aβ precursor protein, an Aβ peptide, Tau, a prion, an Ig light chain, serum amyloid A, transthyretin, cystatin C, beta-2-microglobulin, apolipoprotein AI, apolipoprotein AII, gelsolin, amylin, calcitonin, atrial natriuretic factor, lysozyme, insulin, fibrinogen α-A chain, superoxide dismutase 1, huntingtin, an androgen receptor, an ataxin, a TATA box-binding protein, or TDP-43.

In some embodiments, the proteopathic polypeptide is associated with a proteinopathy comprising: a neurodegenerative disease, a proliferative disease, an inflammatory disease, a cardiovascular disease, diabetes, a synucleinopathy, Parkinson's disease (PD), dementia with Lewy bodies, diffuse Lewy body disease, multiple system atrophy, a tauopathy, Alzheimer's disease (AD), Creutzfeldt-Jakob disease or other prion disease, spinocerebellar ataxias, spinal or bulbar muscular atrophy, amyotrophic lateral sclerosis (ALS), hereditary renal amyloidosis, medullary carcinoma of the thyroid, familial amyloid polyneuropathy, amyloidosis, or frontotemporal degeneration (FTD).

In some embodiments, the alpha-synuclein polypeptide or other proteopathic polypeptide is incapable of self-aggregation in the cell in the absence of the light stimulation (illumination).

In some embodiments, the photoactivatable polypeptide, upon photoactivation, brings molecules of the alpha-synuclein polypeptide or other proteopathic polypeptide into sufficient physical proximity to enable their irreversible self-aggregation.

In some embodiments, the photoactivatable polypeptide is incapable of self-clustering in the cell in the absence of said illumination.

In some embodiments, the cell is comprised in, or is obtained from, an animal (e.g., a transgenic animal engineered to express the alpha-synuclein polypeptide or other proteopathic polypeptide, and the photoactivatable polypeptide).

In some embodiments, the cell expresses an alpha-synuclein polypeptide operably linked to the photoactivatable polypeptide, and wherein the intracellular protein aggregates comprise Lewy body-like aggregates (e.g., aggregates positive for alpha-synuclein phosphorylated at Ser129, ubiquitination, staining with thioflavin S or another amyloid-specific dye, p62, HSP70, or any combination thereof).

In some embodiments, the present description relates to a method for inducing protein aggregation in a cell or animal, the method comprising providing the system as defined herein, and illuminating the cell or animal with light having a wavelength sufficient for photoactivation of the photoactivatable polypeptide, thereby triggering irreversible accumulation of the intracellular protein aggregates comprising the alpha-synuclein polypeptide or proteopathic polypeptide.

In some aspects, the present description relates to a method for selecting a candidate compound for the treatment of a proteinopathy or neurodegenerative disease, the method comprising: (a) providing the system as defined herein; (b) illuminating the cell, or animal comprising said cell, with light having a wavelength sufficient for photoactivation of the photoactivatable polypeptide, thereby triggering accumulation of the intracellular protein aggregates comprising the alpha-synuclein polypeptide or proteopathic polypeptide; (c) administering a compound of interest to the cell or animal; and (d) determining the effect of the compound of interest on the intracellular protein aggregates. In some embodiments, the method may further comprise: (e) selecting the compound of interest as a candidate compound when a decrease in the number and/or size of intracellular protein aggregates is observed.

In some aspects, the present description relates to a method for treating a subject having or susceptible for developing a proteinopathy, the method comprising: (a) providing the system as defined herein, wherein the proteopathic polypeptide is selected based on the subject's proteinopathy; (b) illuminating the cell or animal with light having a wavelength sufficient for photoactivation of the photoactivatable polypeptide, thereby triggering accumulation of the intracellular protein aggregates comprising the proteopathic polypeptide; (c) administering a compound of interest to the cell or animal comprising said cell; (d) determining the effect of the compound of interest on the intracellular protein aggregates; and (e) treating the subject with the compound of interest when a decrease in the intracellular protein aggregates is observed (i.e., in step (d)).

In some aspects, the present description relates to an expression cassette comprising a polynucleotide encoding an alpha-synuclein polypeptide or another proteopathic polypeptide that self-aggregates under pathogenic conditions, operably linked to a photoactivatable polypeptide. In some embodiments, the alpha-synuclein polypeptide or other proteopathic polypeptide may be fused to the proteopathic polypeptide, and/or to a detectable marker as defined herein.

In some aspects, the present description relates to a vector comprising the expression cassette as defined herein, or a cell comprising a genome-integrated expression cassette or vector as defined herein.

In some aspects, the present description relates to a transgenic animal model comprising an expression cassette, a vector, or a cell as defined herein. In some embodiments, the animal may be a mouse, a rat, or other rodent, a non-human primate, fish, nematode, yeast, or a fly.

In some aspects, the present description relates to a protein aggregate comprising an alpha-synuclein polypeptide or another proteopathic polypeptide that self-aggregates under pathogenic conditions, operably linked to a photoactivatable polypeptide. In some embodiments, the protein aggregate may comprise an alpha-synuclein polypeptide operably linked to the photoactivatable polypeptide, wherein the protein aggregate comprises a Lewy body-like aggregate (e.g., positive for: alpha-synuclein phosphorylated at Ser129, ubiquitination, staining with thioflavin S or another amyloid-specific dye, p62, HSP70, or any combination thereof).

In some aspects, the present description relates to a variant alpha-synuclein polypeptide for use in preventing aggregation of a proteopathic polypeptide other than alpha-synuclein, or for use in treating a proteinopathy other than an alpha-synucleinopathy, wherein the variant alpha-synuclein polypeptide lacks self-aggregating activity and inhibits aggregation of the proteopathic polypeptide.

In some aspects, the present description relates to the use of a variant alpha-synuclein polypeptide for the manufacture of a medicament for the treatment of a proteinopathy other than an alpha-synucleinopathy, wherein the variant alpha-synuclein polypeptide lacks self-aggregating activity and inhibits aggregation of a proteopathic polypeptide associated with said proteinopathy.

In some aspects, the present description relates to an expression cassette encoding a variant alpha-synuclein polypeptide for use in preventing aggregation of a proteopathic polypeptide other than alpha-synuclein, or for use in treating a proteinopathy other than an alpha-synucleinopathy, wherein the variant alpha-synuclein polypeptide lacks self-aggregating activity and inhibits aggregation of the proteopathic polypeptide.

In some aspects, the present description relates to the use of an expression cassette encoding a variant alpha-synuclein polypeptide in the manufacture of a medicament for the treatment of a proteinopathy other than an alpha-synucleinopathy, wherein the variant alpha-synuclein polypeptide lacks self-aggregating activity and inhibits aggregation of the proteopathic polypeptide.

General Definitions

Headings, and other identifiers, e.g. (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, "subject" generally refers to a mammal, including primates, and particularly to a human.

Other objects, advantages and features of the present description will become more apparent upon reading of the following non-restrictive description of specific embodiments thereof, given by way of example only with reference to the accompanying drawings.

SEQUENCE LISTING

This specification contains a Sequence Listing in computer readable form created Jun. 28, 2019, having a size of about 56 kb. The computer readable form is incorporated herein by reference.

| SEQ ID NO: 1 | pAAV-LIPA-Empty |
| SEQ ID NO: 2 | pAAV-LIPA-α-syn |

-continued

| | |
|---|---|
| SEQ ID NO: 3 | pAAV-LIPA-αsynΔNAC |
| SEQ ID NO: 4 | pmCherryN1-LIPA-Empty |
| SEQ ID NO: 5 | pmCherry-LIPA-α-syn |
| SEQ ID NO: 6 | pmCherry-LIPA-α-synΔNAC |

BRIEF DESCRIPTION OF THE FIGURES

In the appended figures:

FIG. 9 shows a 3D reconstitution of LIPA-Empty and LIPA-α-syn aggregates (white arrows) in HEK-293T cells exposed 24 h to the blue light (scale bar=2 µm).

FIG. 23 shows the experimental design (left panel), confocal microscopy images (middle panels; scale bar=10 µm), and 3D reconstitution (right panel; scale bar=0.5 µm) illustrating the seeding of monomeric α-syn-GFP by LIPA-α-syn aggregates (n=3).

FIG. 24 shows the experimental design (left panel), confocal microscopy images (middle panels; scale bar=10 µm), and 3D reconstitution (right panel; scale bar=0.7 µm) illustrating the seeding of monomeric α-syn Pffs-488 by LIPA-α-syn aggregates (n=3).

FIG. 25), ubiquitin (FIG. 26), thioflavin S (FIG. 27), p62 (FIG. 28), and HSP70 (FIG. 29) (n=5).

FIGS. 33 and 34), Phosphorylated α-syn at S129 (pS129; FIG. 35), ubiquitin (FIG. 36), thioflavin S (FIG. 37), and p62 (FIG. 38) (n=5 mice). Scale bar=5 µm.

FIG. 53) in the midbrain of mice overexpressing LIPA constructs and exposed or not to the optogenetic stimulation. Results are expressed as % of contralateral non-injected side (n=5-9 mice per experimental condition).

FIGS. 54A-54F shows that LIPA-α-syn co-aggregates with and promotes prion-like propagation of mutant huntingtin (mHtt). FIG. 54A: Low resolution confocal image illustrating the presence of LIPA-α-syn and mHtt-GFP in the injected striatum of wild type C57/B16 mice. FIG. 54B: high resolution confocal images illustrating the co-localization of LIPA-α-syn and mHtt-GFP in the striatal neurons. Low (FIG. 54C) and high (FIG. 54D) resolution confocal images illustrating the presence of LIPA-α-syn and mHtt-GFP in the globus pallidus. Low (FIG. 54E) and high (FIG. 54F) resolution confocal image illustrating the presence of LIPA-α-syn and mHtt-GFP in entopeduncular nucleus.

DETAILED DESCRIPTION

Figure 1:
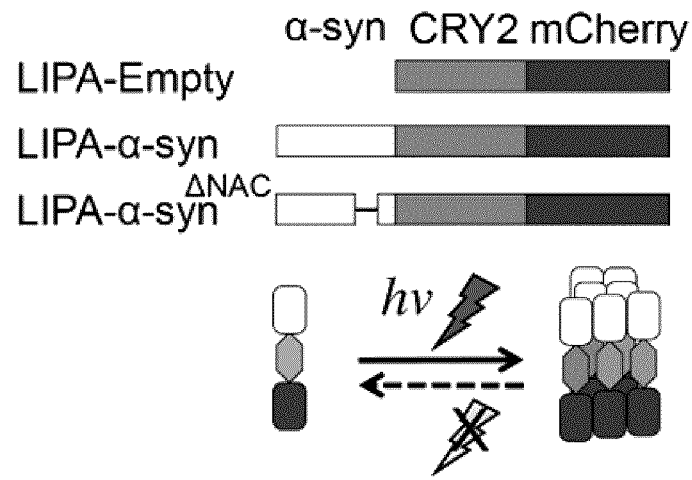
FIG. 1 shows a schematic representation of an embodiment of the light-inducible protein aggregation system described herein.

The present description relates, at least in part, to the discovery that proteopathic polypeptides (e.g., alpha-synuclein or other proteopathic polypeptides, particularly those that self-aggregate under pathogenic conditions) when forced into physical proximity within cell systems using optobiological systems, may trigger the formation of irreversible intracellular protein aggregates that may more closely resemble those found in subjects having proteopathic diseases, thereby providing an improved system for modeling proteinopathies and neurodegenerative disorders. Advantageously, the implementation of optobiological approaches enables the rapid formation of the intracellular protein aggregates in real-time (e.g., in living cells), and in a spatiotemporally-controlled manner.

In some aspects, the present description relates to a light-inducible intracellular protein aggregation (LIPA) system, and methods employing same, useful for the study of proteinopathies or other neurodegenerative disorders. The system generally comprises a cell expressing an alpha-synuclein polypeptide or another proteopathic polypeptide that is known to self-aggregate under pathogenic conditions, operably linked to a photoactivatable polypeptide, wherein illumination of the photoactivatable polypeptide with light having a wavelength sufficient for photoactivation triggers accumulation (e.g., irreversible accumulation) of intracellular protein aggregates comprising the alpha-synuclein polypeptide or proteopathic polypeptide.

As used herein, the expression "alpha-synuclein polypeptide" refers to alpha-synuclein (e.g., human alpha-synuclein), as well as variants and/or fragments thereof (e.g., associated with alpha-synucleinopathies such as Parkinson's disease, dementia with Lewy bodies, and multiple system atrophy). In some embodiments, the alpha-synuclein polypeptide may comprise variants and/or fragments of alpha-synuclein that possess the ability to self-aggregate into Lewy-bodies or Lewy-body-like structures as defined herein. As used herein, the expressions "proteopathic polypeptide", "another proteopathic polypeptide", or "other proteopathic polypeptide" refer to polypeptides associated with proteinopathies (also known as proteopathies, protein conformational disorders, or protein misfolding diseases) other than those encompassed by "alpha-synuclein polypeptide". In some embodiments, the proteopathic polypeptides described herein may possess, or comprise variants and/or fragments that possess, self-aggregating activity and/or seeding activity under pathogenic conditions, which may be the result of protein misfolding.

In some embodiments, the alpha-synuclein polypeptide or proteopathic polypeptide described herein may comprise variants and/or fragments of unknown self-aggregating and/or seeding activity, wherein the LIPA system described herein may be used to study the variants and/or fragments. In some embodiments, the LIPA system described herein may comprise or further comprise an alpha-synuclein polypeptide or proteopathic polypeptide that lacks self-aggregating and/or seeding activity, or that has a dominant negative effect with respect to self-aggregating and/or seeding activity. Such variants and/or fragments of alpha-synuclein may be useful, for example, as experimental controls for the system described herein.

In some embodiments, the alpha-synuclein polypeptide or other proteopathic polypeptide described herein may be or comprise a polypeptide that, upon self-aggregation (e.g., under pathogenic conditions), adopts a misfolded conformation (e.g., a filamentous confirmation) that may be rich in beta-sheets (e.g., having an increase in beta-sheets as compared to a corresponding non-pathogenic native alpha-synuclein polypeptide or other proteopathic polypeptide).

In some embodiments, the alpha-synuclein polypeptide or other proteopathic polypeptide described herein may be or comprise a polypeptide that, upon self-aggregation (e.g., under pathogenic conditions), exhibits seeding activity. As used herein, the expression "seeding activity" refers to the ability of an alpha-synuclein polypeptide or other proteopathic polypeptide described herein to nucleate (i.e., induce or trigger) self-aggregation or aggregation of proteins having similar aggregation domains, whereby small oligomers, or seeds, provide a template for the assembly of soluble monomer proteins into highly ordered protein aggregates defined by their insolubility and beta-sheet structure.

In some embodiments, the proteopathic polypeptide described herein, may be, comprise, or be derived from: an Aβ precursor protein, an Aβ peptide, Tau, a prion, an Ig light chain, serum amyloid A, transthyretin, cystatin C, beta-2-microglobulin, apolipoprotein AI, apolipoprotein AII, gelsolin, amylin, calcitonin, atrial natriuretic factor, lysozyme, insulin, fibrinogen α-A chain, superoxide dismutase 1, huntingtin, an androgen receptor, an ataxin, a TATA box-binding protein, TDP-43, or another protein associated with a proteinopathy (Stefani and Dobson, 2003). In some embodiments, the proteopathic polypeptide described herein may be associated with a proteinopathy comprising: a neurodegenerative disease, a proliferative disease, an inflammatory disease, a cardiovascular disease, diabetes, a synucleinopathy, Parkinson's disease, dementia with Lewy bodies, diffuse Lewy body disease, multiple system atrophy, a tauopathy, Alzheimer's disease, Creutzfeldt-Jakob disease or other prion disease, spinocerebellar ataxias, spinal or bulbar muscular atrophy, amyotrophic lateral sclerosis, hereditary renal amyloidosis, medullary carcinoma of the thyroid, familial amyloid polyneuropathy, amyloidosis, or frontotemporal degeneration.

In some embodiments, the alpha-synuclein polypeptide or other proteopathic polypeptide described herein is incapable of self-aggregation in the cell in the absence of said illumination, within the context of the LIPA system. Such a characteristic may reduce undesirable "background" introduced into the LIPA system.

In some embodiments, the "photoactivatable polypeptide" described herein generally refers to a protein useful as an optobiological tool, more particularly proteins that respond to illumination with light (e.g., visible or infrared light) by changing their conformations (Kim and Lin, 2013; Khamo et al., 2017). Such light-triggered conformational changes can induce, for example, inter- or intra-molecular interactions, which can then be exploited as taught herein to bring molecules of the alpha-synuclein polypeptide or other proteopathic polypeptide (operably linked to the photoactivatable polypeptide) into sufficient physical proximity to enable or trigger their self-aggregation and/or seeding activity. Some examples of photoactivatable proteins and systems that may be adapted for use in the LIPA systems and methods described herein, in view of the present disclosure, are reviewed in Khamo et al. (2017).

In some embodiments, the photoactivatable polypeptides of the present description, upon photoactivation, bring molecules of the alpha-synuclein polypeptide or other proteopathic polypeptide into sufficient physical proximity to enable their self-aggregation (e.g., irreversible self-aggregation). In some embodiments, the molecules of the alpha-synuclein polypeptide or other proteopathic polypeptide may be brought into physical proximity via: light-induced homo- or hetero-protein association, light-induced conformation change, or light-induced inter- or intra-molecular interactions of the photoactivatable polypeptide. In some embodiments, the homo- or hetero-protein association, conformation change, or inter- or intra-molecular interactions of the photoactivatable polypeptide may be reversible following cessation of the illumination. In some embodiments, the photoactivatable polypeptide is preferably incapable of self-clustering in the cell in the absence of the illumination within the LIPA system. Indeed, photoinactivation-independent self-clustering of the photoactivatable polypeptide may negatively affect the sensitivity and the LIPA system described herein.

In some embodiments, the photoactivatable polypeptide may be, comprise, or be derived from: a photoreceptor, a cryptochrome, a phytochrome, cryptochrome 2 (CRY2), light-oxygen-voltage (LOV) domains, CRY2-CIB1 (calcium and integrin-binding protein 1) variants, CRY2E490G, CRY2clust, iLID nano and iLID micro, LOVTRAP, Magnets, cobalamin binding domain CBD, VfAU1-LOV, CPH1S, BphP1-PpsR2 (see Table 1 of Khamo et al., 2017), or another photoactivatable protein or system employed in optobiology.

In some embodiments, the LIPA system comprises the replacement of one photoactivatable polypeptide within another photoactivatable polypeptide that is photoactivatable by a light of a different color or wavelength (Zhang and Cui, 2015), providing a further degree of modularity to the LIPA system. In some embodiments, the photoactivatable polypeptide and the alpha-synuclein or other proteopathic polypeptide described herein are operably linked. In such a context, the term "operably linked" refers to the joining of the photoactivatable polypeptide and the alpha-synuclein or other proteopathic polypeptide via a covalent or non-covalent interaction within the cell. For example, in some embodiments, the photoactivatable polypeptide and the alpha-synuclein or other proteopathic polypeptide may be comprised in a fusion protein expressed from a single polynucleotide. In other embodiments, the photoactivatable polypeptide and the alpha-synuclein or other proteopathic polypeptide may be each engineered (e.g., as fusion proteins) to comprise protein interaction domains that bind directly or indirectly to one another, to the effect that the photoactivatable polypeptide and the alpha-synuclein or other proteopathic polypeptide are expressed in the cell as separate proteins, which then come together via their protein interaction domains within the intracellular environment (e.g., the cytosol).

In some embodiments, the LIPA system comprises non-naturally-occurring polypeptides and/or cells. In some embodiments, at least one of the alpha-synuclein polypeptide, other proteopathic polypeptide, or photoactivatable polypeptide is heterologous with respect to the cell and/or to each other. In some embodiments, the expression of at least one of the alpha-synuclein polypeptide, other proteopathic polypeptide, or photoactivatable polypeptide may be engineered to be under the control of a constitutively active promoter or an inducible promoter.

In some embodiments, the LIPA system comprises cells such as neuronal cells, brain cells, induced pluripotent stem cells, mammalian cells, neuroblastomas, immune cells, or blood cells. Such cells may serve as models for studying various proteinopathies. In some embodiments, the cells may be comprised in an animal (e.g., a transgenic animal engineered to expresses the alpha-synuclein polypeptide or other proteopathic polypeptide, and the photoactivatable polypeptide). In some embodiments, the cells may be obtained from such an animal (or a human subject having or suspected of having a proteinopathy) in ex vivo implementations of the present LIPA system.

In particular embodiments, illumination of the photoactivatable polypeptide with light having a wavelength sufficient for photoactivation triggers accumulation (e.g., irreversible accumulation) of intracellular protein aggregates (e.g., insoluble aggregates) comprising the alpha-synuclein polypeptide or proteopathic polypeptide. In some embodiments, the LIPA system and methods described herein enable the intracellular protein aggregates to accumulate in real-time during following the illumination, thereby enabling spatiotemporal control of protein aggregation. In some embodiments, the intracellular protein aggregates accumulate rapidly, such as within 8 h, 7 h, 6 h, 5 h, 4 h, 3 h, 2 h, 1 h, 30 min, 15 min, 10 min, or 5 min following the illumination of the photoactivatable polypeptide.

In some embodiments, the intracellular protein aggregates described herein may be, at least in part, irreversible following cessation of the illumination. As used herein, the term "irreversible" refers to intracellular protein aggregates induced by the LIPA system described herein having the ability to remain relatively more stable following cessation of illumination, as compared to corresponding control cells lacking the alpha-synuclein or other proteopathic polypeptide and/or control cells comprising the photoactivatable peptide alone. In particular embodiments, the intracellular protein aggregates may remain stable for at least 5 h, 10 h, 15 h, 20 h, 25 h, 30 h, 35 h, 40 h, 2 days, 3 days, 4 days, 5 days, 6 days, 7 days, 10 days, 20 days, or 30 days post-illumination.

In some embodiments, the intracellular protein aggregates induced by the present LIPA system may comprise misfolded proteins (e.g., misfolded alpha-synuclein or other proteopathic polypeptides described herein) in beta-sheet conformation. In some embodiments, the intracellular protein aggregates induced by the present LIPA system may comprise the misfolded proteins adopting a conformation (e.g., a filamentous conformation) that may be rich in beta-sheets (e.g., having an increase in beta-sheets as compared to a corresponding non-pathogenic native alpha-synuclein polypeptide or other proteopathic polypeptide). In some embodiments, the intracellular protein aggregates induced by the present LIPA system may comprise misfolded proteins (e.g., misfolded alpha-synuclein or other proteopathic polypeptides described herein) having an increase in phosphorylation (e.g., serine phosphorylation) as compared to a corresponding non-pathogenic native alpha-synuclein polypeptide or other proteopathic polypeptide. In some embodiments, the intracellular protein aggregates induced by the present LIPA system may comprise misfolded proteins (e.g., misfolded alpha-synuclein or other proteopathic polypeptides described herein) having an increase in ubiquitination as compared to a corresponding non-pathogenic native alpha-synuclein polypeptide or other proteopathic polypeptide.

In some embodiments, the present LIPA system may comprise a cell expressing an alpha-synuclein polypeptide operably linked to the photoactivatable polypeptide, and wherein the intracellular protein aggregates comprise Lewy body-like aggregates. As used herein, "Lewy body-like aggregates" refer to protein aggregates comprising alpha-synuclein polypeptides which having properties resembling those of Lewy bodies found in the brains of Parkinson's disease subjects. In some embodiments, the Lewy body-like aggregates described herein may be positive for: alpha-synuclein phosphorylated at Ser129, ubiquitination, staining with thioflavin S or another amyloid-specific dye, p62, HSP70, or any combination thereof.

In some embodiments, the photoactivatable polypeptide and/or the alpha-synuclein or other proteopathic polypeptide may be fused to a detectable marker (e.g., a fluorescent protein, a reporter enzyme, a transcription factor, a radio-isotope binding protein, or a bioluminescent protein). In some embodiments, the fluorescent protein is a green fluorescent protein, a cyan fluorescent protein, a blue fluorescent protein, a yellow fluorescent protein, a red fluorescent protein (e.g., mCherry), or any combination thereof. As used herein in the context of florescent proteins, the terms "green", "cyan", "blue", "yellow", and "red" relate to proteins that fluoresce in that color spectra when excited.

In some embodiments, the LIPA system may comprise cells stably transfected or infected with, or genome-edited to comprise, one or more polynucleotides encoding the photoactivatable polypeptide and/or the alpha-synuclein polypeptide or other proteopathic polypeptide.

In some aspects, the present description relates to a method for inducing protein aggregation in a cell or animal, the method comprising providing a LIPA system as described herein, and illuminating the cell or animal with light having a wavelength sufficient for photoactivation of the photoactivatable polypeptide, thereby triggering accumulation (e.g. irreversible accumulation) of the intracellular protein aggregates comprising the alpha-synuclein polypeptide or proteopathic polypeptide.

In some aspects, the present description relates to a method for selecting a candidate compound for the control or treatment of a proteinopathy or neurodegenerative disease (e.g., a proteinopathy or neurodegenerative disease as described herein), the method comprising: (a) providing a LIPA system as described herein; (b) illuminating the cell, or animal comprising said cell, with light having a wavelength sufficient for photoactivation of the photoactivatable polypeptide, thereby triggering accumulation of the intracellular protein aggregates comprising the alpha-synuclein polypeptide or proteopathic polypeptide; (c) administering a compound of interest to the cell or animal; and (d) determining the effect of the compound of interest on the intracellular protein aggregates. In some embodiments, the method may further comprise: (e) selecting the compound of interest as a candidate compound when a decrease in the number and/or size of intracellular protein aggregates is observed.

In some embodiments, the compound of interest or candidate compound may be, or comprise, a small molecule or a biologic.

In some aspects, the present description relates to pharmacological, genetic, or biomarker-based approaches for treating a subject having developed or being susceptible to developing a proteinopathy (e.g., a proteinopathy described herein). In some embodiments, the method may comprise: (a) providing a LIPA system as described herein, wherein the proteopathic polypeptide is selected based on the subject's proteinopathy; (b) illuminating the cell or animal with light having a wavelength sufficient for photoactivation of the photoactivatable polypeptide, thereby triggering accumulation of the intracellular protein aggregates comprising the proteopathic polypeptide; (c) administering a compound of interest to the cell or animal comprising said cell; (d) determining the effect of the compound of interest on the intracellular protein aggregates; and (e) treating the subject with the compound of interest when a decrease in the intracellular protein aggregates is observed (i.e., in step (d)).

In some embodiments, the methods described herein may be an in vitro, ex vivo, or in vivo method.

In some aspects, the present description relates to an expression cassette comprising a polynucleotide encoding an alpha-synuclein polypeptide or another proteopathic polypeptide that self-aggregates under pathogenic conditions, operably linked to a photoactivatable polypeptide. In some embodiments, the alpha-synuclein polypeptide or other proteopathic polypeptide may be fused to the proteopathic polypeptide, and/or to a detectable marker (e.g. a detectable marker as described herein). In some embodiments, the expression cassette may comprise an alpha-synuclein polypeptide or other proteopathic polypeptide placed under control of a constitutively active promoter, an inducible promoter, or a tissue-specific promoter (e.g., neuronal cell-specific promoter).

In some aspects, the present description relates to a vector comprising the expression cassette as described herein.

In some aspects, the present description relates to a cell comprising a genome-integrated expression cassette or vector as described herein. In some embodiments, the cell may be a neuronal cell, a brain cell, an induced pluripotent stem cell, a mammalian cell, a neuroblastoma, an immune cell, or a blood cell.

In some aspects, the present description relates to a transgenic animal model comprising the expression cassette, a vector, or a cell as described herein. In some embodiments, the animal may be a mouse, rat or other rodent, a non-human primate, fish, nematode, yeast, or a fly.

In some aspects, the present description relates to a protein aggregate comprising an alpha-synuclein polypeptide or another proteopathic polypeptide that self-aggregates under pathogenic conditions, operably linked to a photoactivatable polypeptide. In some embodiments, (a) the protein aggregate is as defined herein; (b) the photoactivatable polypeptide and the alpha-synuclein or other proteopathic polypeptide are comprised in a fusion protein; (c) the photoactivatable polypeptide and/or the alpha-synuclein or other proteopathic polypeptide are fused to a detectable marker or a detectable marker as defined herein; (d) the alpha-synuclein polypeptide or the proteopathic polypeptide is as defined herein; (e) the photoactivatable polypeptide is as defined herein; (f) at least one of the alpha-synuclein polypeptide, other proteopathic polypeptide, or photoactivatable polypeptide is heterologous with respect to the cell and/or to each other; (g) at least one of the alpha-synuclein polypeptide, other proteopathic polypeptide, or photoactivatable polypeptide is under the control of a constitutively active promoter, an inducible promoter, or a tissue-specific promoter; (h) the protein aggregate is comprised in a neuronal cell, a brain cell, an induced pluripotent stem cell, a mammalian cell, a neuroblastoma, an immune cell, or a blood cell; (g) the protein aggregate is comprised in a cell in an animal or a transgenic animal engineered to express the alpha-synuclein polypeptide or other proteopathic polypeptide, and the photoactivatable polypeptide; (h) the protein aggregates comprise misfolded proteins in beta-sheet conformation; or (i) any combination of (a) to (h).

In some embodiments, the protein aggregate may comprise an alpha-synuclein polypeptide operably linked to the photoactivatable polypeptide, wherein the protein aggregate comprises a Lewy body-like aggregate. In some embodiments, the Lewy body-like aggregate is positive for: alpha-synuclein phosphorylated at Ser129, ubiquitination, staining with thioflavin S or another amyloid-specific dye, p62, HSP70, or any combination thereof.

In some embodiments, the protein aggregates as defined herein may be for use in a light-inducible intracellular protein aggregation system, in a method for inducing protein aggregation in a cell or animal, in a method for selecting a candidate compound for the treatment of a proteinopathy or neurodegenerative disease, or in the method for treating a subject (e.g., an animal or cell) having or susceptible for developing a proteinopathy.

In some embodiments, the present description relates to the surprising discovery that a variant of alpha-synuclein incapable of self-aggregating (e.g., lacking the NAC region) was able to preclude, prevent, or inhibit the self-aggregation of a polypeptide other than alpha-synuclein (e.g., CRY2). Thus, in some aspects, the present description relates to a variant alpha-synuclein polypeptide for use in preventing aggregation of a proteopathic polypeptide other than alpha-synuclein, or for use in treating a proteinopathy other than an alpha-synucleinopathy, wherein the variant alpha-synuclein polypeptide lacks self-aggregating activity and inhibits aggregation of the proteopathic polypeptide.

In some aspects, the present description also relates to the use of a variant alpha-synuclein polypeptide for the manufacture of a medicament for the treatment of a proteinopathy other than an alpha-synucleinopathy, wherein the variant alpha-synuclein polypeptide lacks self-aggregating activity and inhibits aggregation of a proteopathic polypeptide associated with said proteinopathy. In some embodiments, the variant alpha-synuclein polypeptide referred to above is, comprises, or is from beta-synuclein.

In some aspects, the present description relates to an expression cassette encoding a variant alpha-synuclein polypeptide for use in preventing aggregation of a proteopathic polypeptide other than alpha-synuclein, or for use in treating a proteinopathy other than an alpha-synucleinopathy, wherein the variant alpha-synuclein polypeptide lacks self-aggregating activity and inhibits aggregation of the proteopathic polypeptide. In some embodiments, the present description relates to the use of an expression cassette encoding a variant alpha-synuclein polypeptide in the manufacture of a medicament for the treatment of a proteinopathy other than an alpha-synucleinopathy, wherein the variant alpha-synuclein polypeptide lacks self-aggregating activity and inhibits aggregation of the proteopathic polypeptide. In some embodiments, the proteopathic polypeptide other than alpha-synuclein is, comprises, or is from: an Aβ precursor protein, an Aβ peptide, Tau, a prion, an Ig light chain, serum amyloid A, transthyretin, cystatin C, beta-2-microglobulin, apolipoprotein AI, apolipoprotein AII, gelsolin, amylin, calcitonin, atrial natriuretic factor, lysozyme, insulin, fibrinogen α-A chain, superoxide dismutase 1, huntingtin, an androgen receptor, an ataxin, a TATA box-binding protein, or TDP-43. In some embodiments, the proteinopathy other than an alpha-synucleinopathy is: a neurodegenerative disease, a proliferative disease, an inflammatory disease, a cardiovascular disease, diabetes, Parkinson's disease, dementia with Lewy bodies, diffuse Lewy body disease, multiple system atrophy, a tauopathy, Alzheimer's disease, Creutzfeldt-Jakob disease or other prion disease, spinocerebellar ataxias, spinal or bulbar muscular atrophy, amyotrophic lateral sclerosis, hereditary renal amyloidosis, medullary carcinoma of the thyroid, familial amyloid polyneuropathy, amyloidosis, or frontotemporal degeneration.

In some embodiments, the present description may relate to the use of genome-editing (e.g., a CRISPR-based genomic editing system) to generate variant alpha-synuclein polypeptide as defined herein in a subject (e.g., in the brain of a subject).

EXAMPLES

Example 1

Materials and Methods 1.1 Construction of Plasmids and Production of Recombinant Adeno-Associated 2/6 Viral Vectors CRY2olig-mCherry plasmid was kindly provided by Dr. Chandra Tucker (Addgene plasmid #60032), pCDNA-human α-syn plasmid was kindly provided by Dr. Hilal Lashuel (EPFL, Switzerland), pCDNA-human α-syn$^{\Delta NAC}$, missing the NAC region (aa71-82) plasmid was kindly provided by Dr. Benoit Giasson (University of Florida, USA), and AAV-CMV-MCS plasmid was kindly provided by Dr. Bernard Schneider (EPFL, Switzerland).

To generate LIPA constructs, the cDNAs encoding human α-syn or human α-syn$^{\Delta NAC}$ were subcloned in CRY2olig-mCherry and verified by sequencing. To generate plasmids for the production of adeno-associated viral vectors, the cDNA encoding LIPA-α-syn (α-syn-CRY2olig-mCherry) was subcloned in the AAV-CMV-MCS shuttle plasmid, using standard cloning procedures, and verified by sequencing.

The production of the recombinant pseudotyped AAV2/6 vectors (serotype 2 genome/serotype 6 capsid) and relative infectivity titers were performed by the Canadian Neurophotonics Platform (CERVO, Québec City). The final viral titers of AAV-LIPA-α-syn viral vector was $1 \times 10^{13}$ genome copies (GC)/mL.

Figure 39:
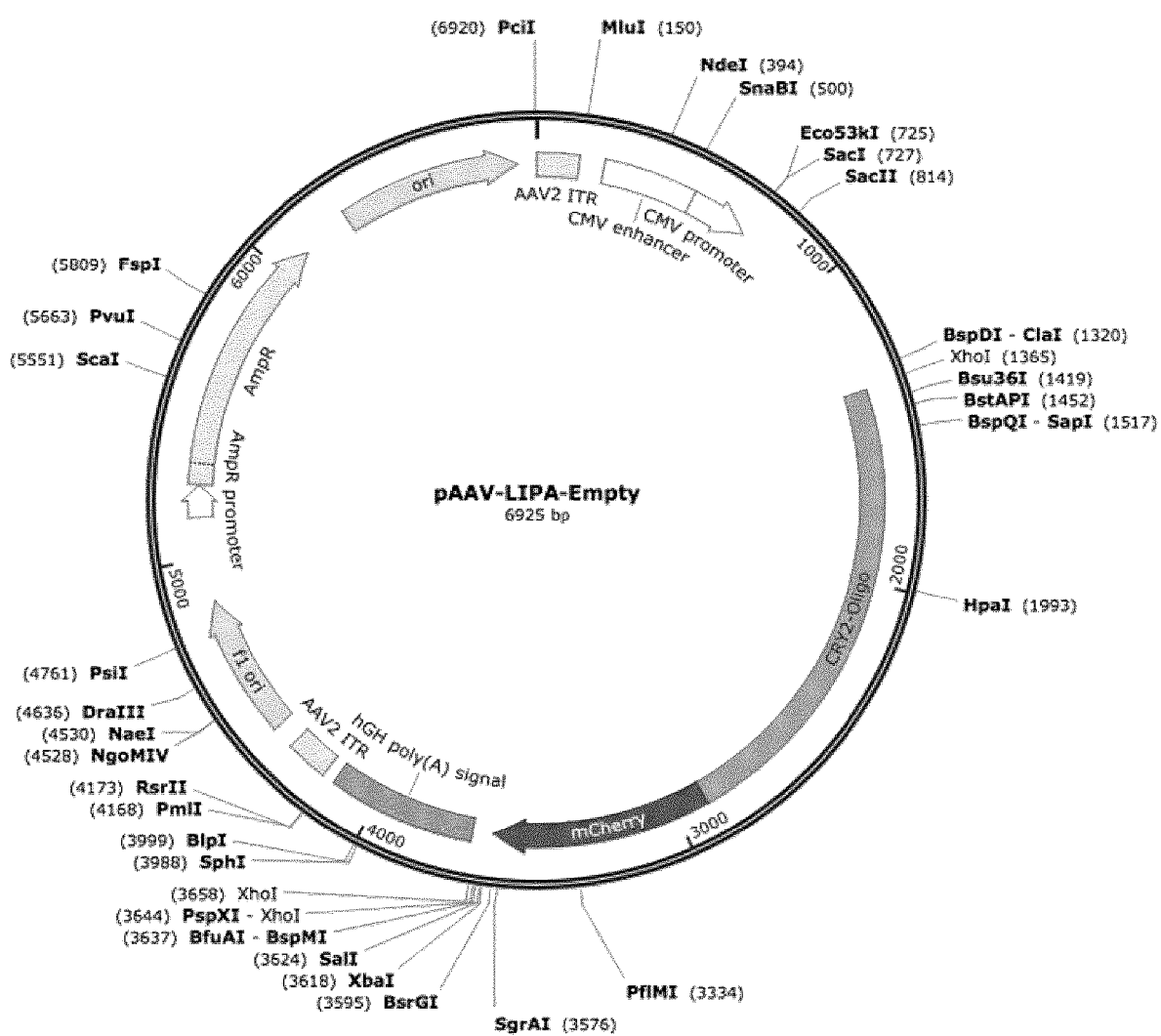
FIGS. 39-44 are plasmid maps of plasmid used for mammalian expression, including pmCherryN1-LIPA-Empty (FIG. 42), pmCherry-LIPA-α-syn (FIG. 43), and pmCherry-LIPA-α-synΔNAC (FIG. 44).
Figure 40:
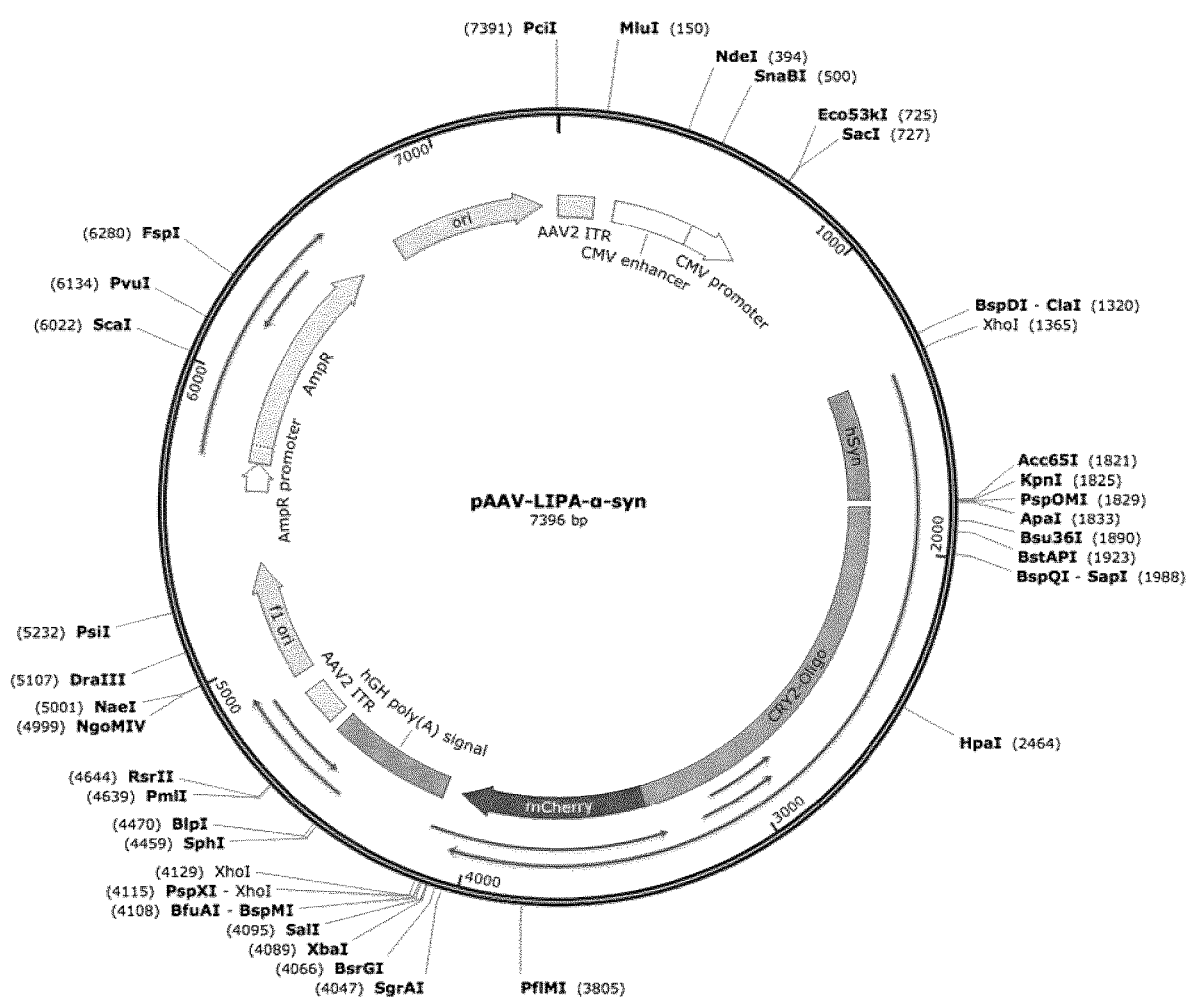
Figure 41:
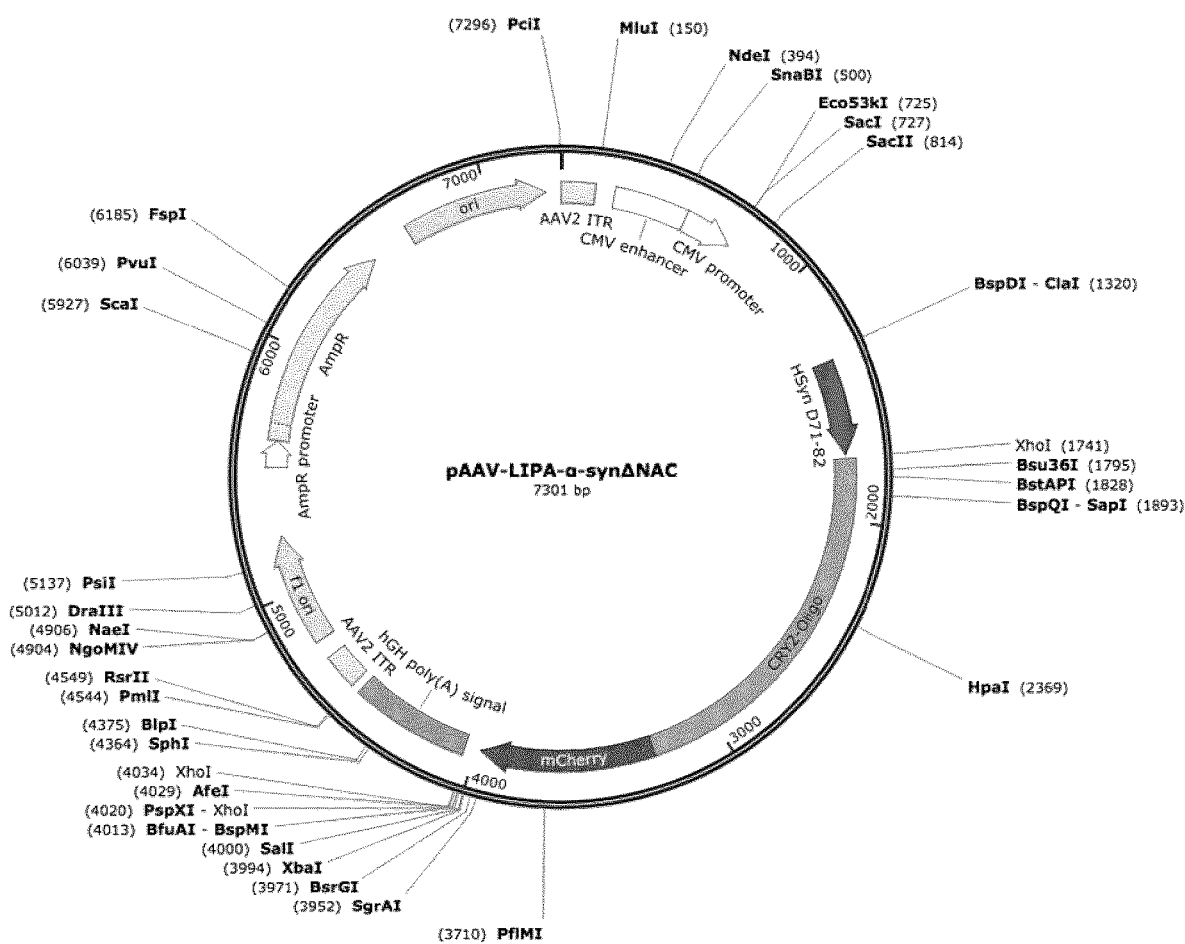

Plasmids used for adeno-associated viral production (AAV2) include pAAV-LIPA-Empty (FIG. 39; SEQ ID NO: 1), pAAV-LIPA-α-syn (FIG. 40; SEQ ID NO: 2), and pAAV-LIPA-αsynΔNAC (FIG. 41; SEQ ID NO: 3).

1.2 Cell Culture and DNA Transient Transfection

Human HEK-293T cells were maintained in high glucose Dulbecco's modified Eagle's medium (DMEM, Sigma) supplemented with 10% Fetal Bovine Serum (FBS, Sigma) and 1% penicillin/streptomycin (Gibco/Life technologies) at 37° C. and 5% CO$_2$.

HEK-293T cells were transfected using calcium phosphate, FastFect™ transfection (Feldan, 9K-010-0001) or Lipofectamine™ 2000 (Thermo Fisher Scientific) according to a standard protocol and leading to more than 95% of transfection efficiency.

Figure 42:
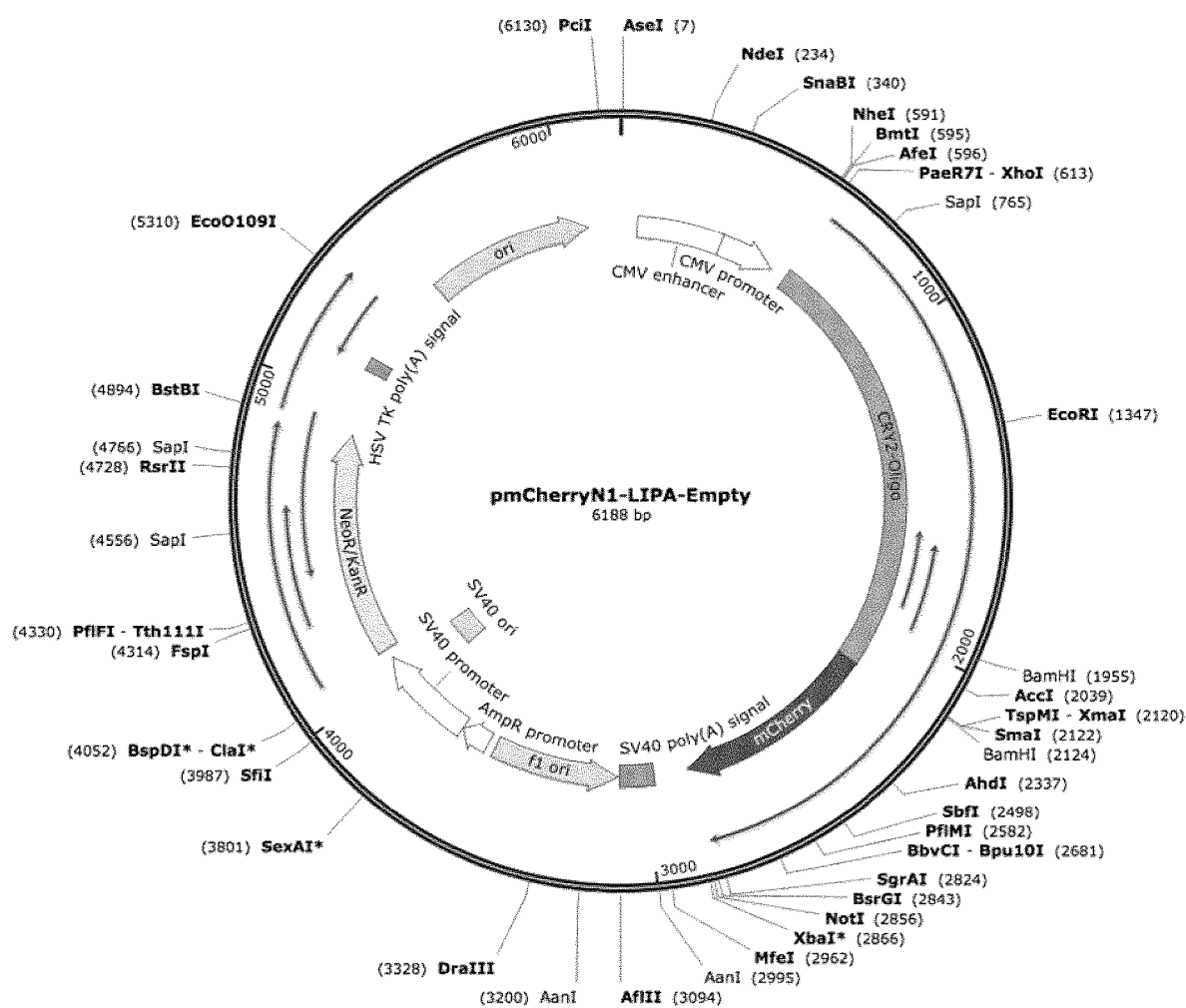
Figure 43:
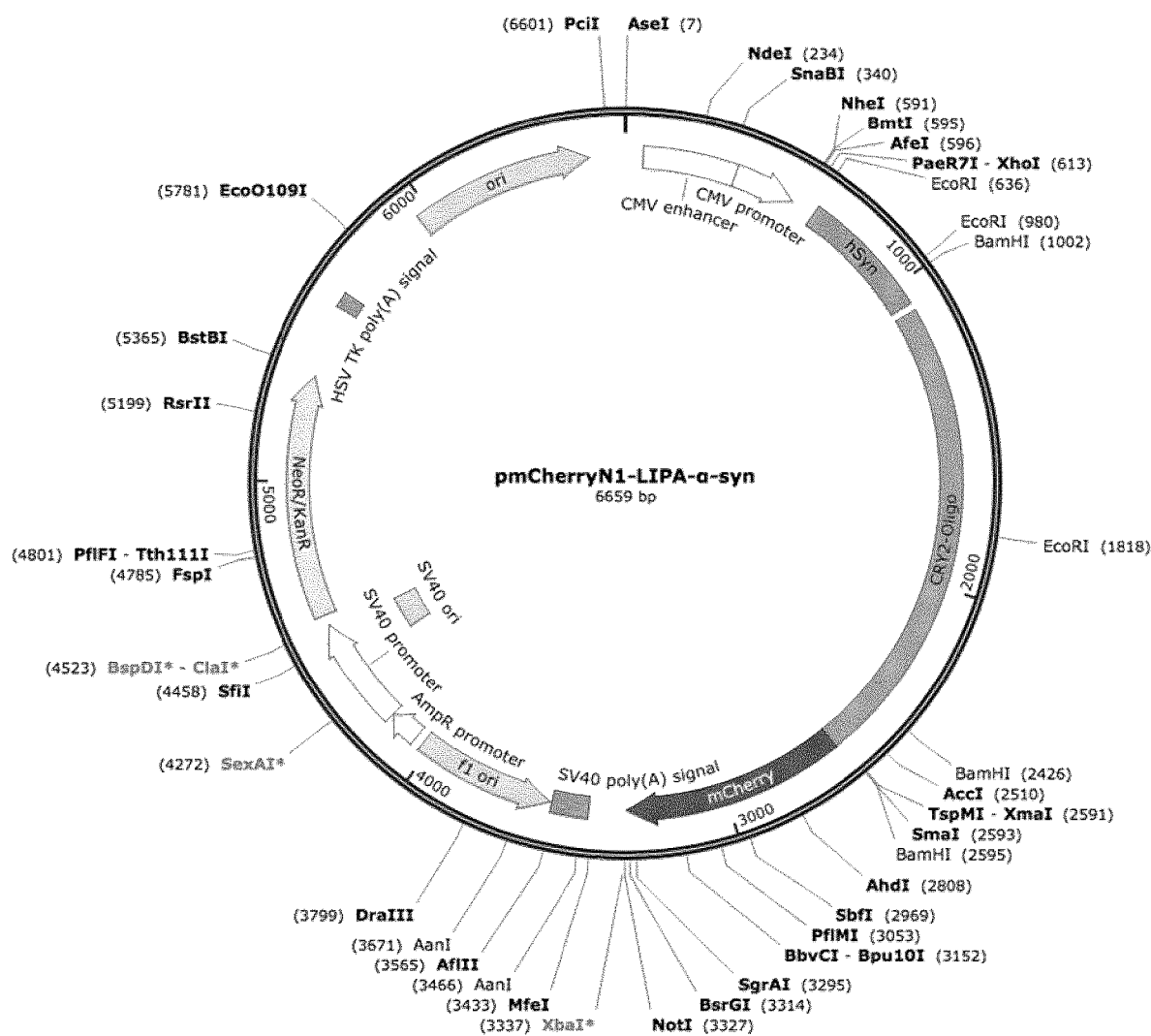
Figure 44:
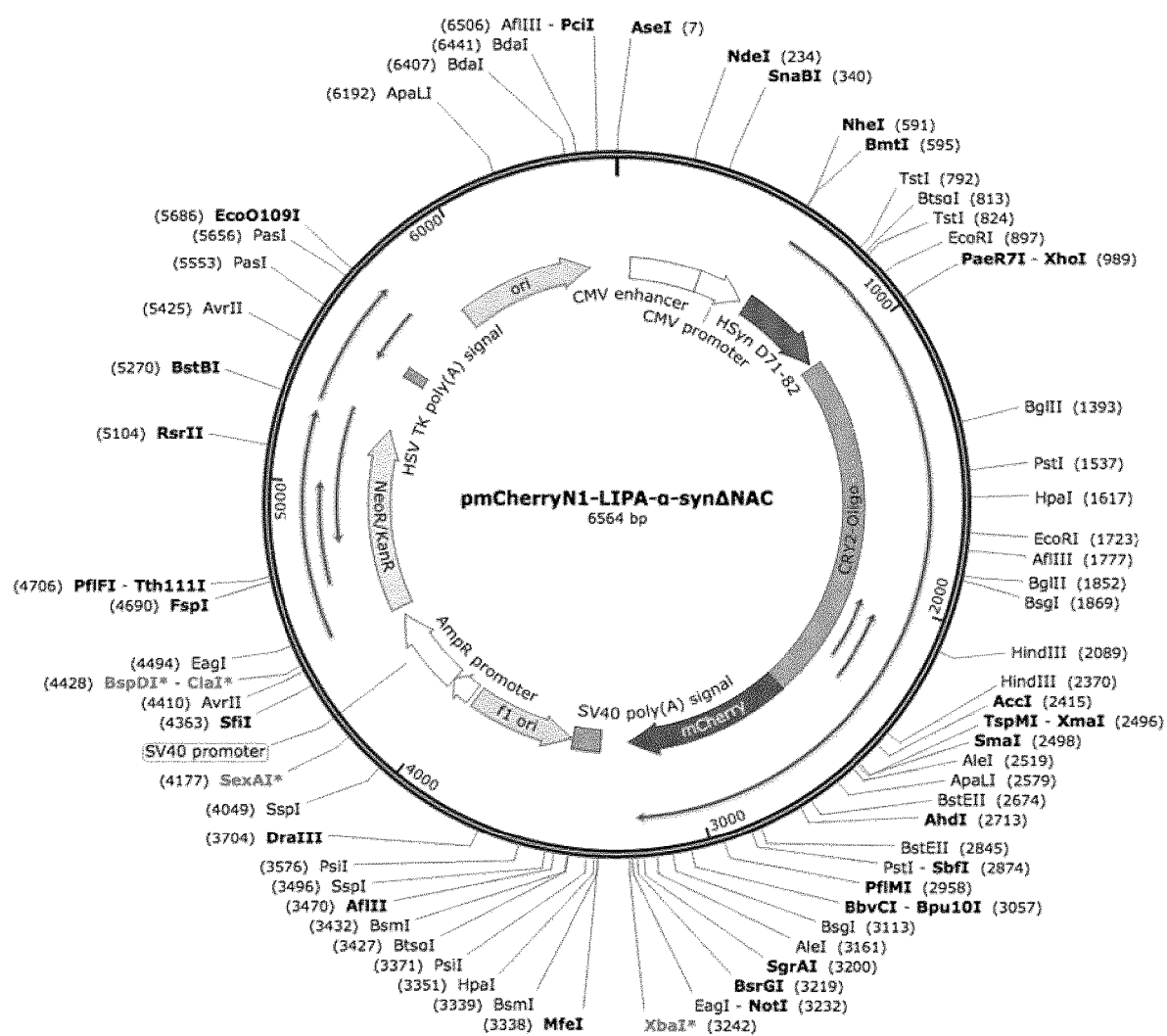

Plasmids used for mammalian expression include pmCherryN1-LIPA-Empty (FIG. 42; SEQ ID NO: 4), pmCherry-LIPA-α-syn (FIG. 43; SEQ ID NO: 5), and pmCherry-LIPA-α-syn$^{\Delta NAC}$ (FIG. 44; SEQ ID NO: 6).

1.3 Live-Cell Imaging and 3D Animation

HEK-293T cells were transfected at 30-50% confluence using Lipofectamine™ 2000. 24 h later, live imaging was performed making use of a Zeiss LSM 700 confocal microscope and the heating insert P Lab-Tek™ S1 systems. LIPA photoactivation was induced by laser illumination (488 nm) at 1% (15.5 µW). Time-lapse acquisitions were performed every 35 sec with photoactivation of a small ROI in the high magnification images (40×) or the whole field in the low magnification images (20×) with the 488 nm laser wavelength just prior to each frame recording. During the entire recording time, conditions were controlled and cells were maintained at 37° C., 5% $CO_2$.

Time lapse microscopy data was analysed using Imaris™ software version 7.6.1 (Bitplane, Zurich, Switzerland). Images were segmented using the isocontour feature in the Surpass module. Highly expressing mCherry-positive aggregates were detected based on the local contrast, their shape and their volume. Cell volume was detected as a low-intensity mCherry expression volume and used to normalise the quantity of detected aggregates. Animation rendering was performed with the Imaris software and video were exported using QuickTime' Pro 7 (Apple, Cupertino, Calif.).

1.4 Induction of Protein Aggregation, Immunocytochemistry and Cell Quantification in Culture HEK-293T cells were seeded on 0.1% gelatin-coated glass coverslips in 24-well plates at a density of $10^4$ cells per well (50% confluence) and transiently transfected, 24 h later, with 0.5 µg of LIPA-Empty, 0.6 µg LIPA-α-syn, and 1 µg LIPA-α-syn$^{\Delta NAC}$ per 4 wells, to obtain similar protein expression levels in all conditions. 24 h post-transfection, cells were exposed to blue light ($\lambda$=456 nm) using UHP-T-DI-LED series Ultra High-Power LEDs (Prizmatix), at an intensity of 0.8 mW/cm$^2$, as measured using LPM-100 light power meter (Amuza). Cells were collected at different time points and fixed in 4% paraformaldehyde for 15 min at room temperature (RT), then washed three times (5 min) with PBS and permeabilized with PBS containing 0.25% Triton X-100, for 30 min at RT. Cells were incubated in blocking buffer solution (PBS containing 5% BSA and 0.1% Triton X-100), for 1 h at RT. Coverslips were incubated with primary antibodies (see Table 1) diluted in blocking buffer solution for 2 h at RT. Coverslips were washed three times in blocking buffer solution (10 min) and appropriate Alexa Fluor® secondary antibodies (Life Technologies, see Table 1) were applied for 1 h at RT. Coverslips were washed twice with PBS (10 min) and counterstained with the fluorescent nuclear stain diluted in 4,6-diamidino-2-phenylindole (DAPI) (1:5000) for 5 min. Coverslips were then washed twice with PBS (10 min), mounted on Prolong® Gold Antifade (Molecular Probes), and imaged using a Zeiss LSM800 confocal microscope. For thioflavin S (ThS) staining, fixed and permeabilized cells were incubated with 0.05% ThS for 15 min, washed three times with 70% ethanol for 10 min, and then cells were directly counterstained with DAPI. All immunocytochemistry experiments were made with gentle rocking and protected from light.

To evaluate the number of mCherry-positive cells with aggregates, a total of 8-10 images per condition were collected using a fluorescence microscope (Nikon Eclipse 80i; 20× objective) and a total of 220-250 cells were quantified by two experimenters, in a blind manner, using ImageJ.

1.5 Semi-Denaturing Detergent-Agarose Gel Electrophoresis (SDD-AGE)

HEK-293T cells transiently overexpressing LIPA constructs were collected at different time points post-stimulation with blue light (0.8 mW/cm$^2$). Cells were lysed with a Dremel tissue homogenizer at low intensity for 10 sec (BioSpec Products, Inc., Bartlesville, Okla.) in lysis buffer (PBS-Tween 0.05%+Protease inhibitor, Phosphatase inhibitor II and Phosphatase inhibitor III [Sigma] and PMSF). Samples were centrifuged at 4° C. (2000×g for 10 min). Supernatant was collected and samples were treated at RT for 7 min in sample buffer (20% glycerol, 0.01% bromophenol blue, and 0.08% SDS). Samples were immediately electrophoresed through a 1.8% agarose gel prepared in buffer G (20 mM Tris and 0.2 M glycine), containing 0.02% SDS. The SDD-AGE was run in buffer G containing 0.01% SDS at 120 V until the dye reached the end of the gel. The gels were then transferred to nitrocellulose membranes using the Trans-Blot® Turbo™ Transfer (Bio-Rad). The membranes were then dried for 1 h at RT then incubated in Odyssey blocking buffer (LI-COR Biosciences) at RT for 1 h prior to overnight incubation with primary antibodies in the blocking solution. Membranes were then washed 3 times with PBS-Tween 0.1% (PBST) (10 min), and incubated with the appropriate secondary antibodies; either IRDye® 680RD-conjugated or IRDye® 800W-conjugated secondary antibodies (LI-COR Biosciences). Membranes were washed 3 times with PBS-T (10 min). Visualisation and quantification were carried out with the LI-COR Odyssey scanner and software (LI-COR Biosciences). Blots were imaged using the Odyssey Infrared Imaging System Scan resolution of the instrument ranges from 21 to 339 µm, and in this study membrane blots were imaged at 169 µm. Quantification was performed on single channels with the analysis software provided with the LI-COR imaging system. Molecular weight markers were not used because nondenatured protein aggregates were being analyzed. At least three independent experiments were analysed for SDD-AGE. The data is presented the means±s.e.m.

1.6 Filter Retardation Blotting Assay

Cells were processed similarly to SDD-AGE, except that after cell lysis and centrifugation, the samples were diluted with lysis buffer containing 1% SDS, and samples were incubated at RT for 10 min. The vacuum manifold (Core Life Science) was prepared by using thin filter paper presoaked in water and placed on the manifold. A cellulose acetate membrane (pore size 0.2 µm; SterliTech) was soaked in PBS containing 1% SDS and placed on top of the filter paper on the manifold. The manifold was tightly closed and samples were loaded in triplicates into the wells. Then, the samples then were filtered through the membrane by applying a vacuum. After filtration, the membrane was washed 2 times with PBS containing 0.1% SDS. The acetate membrane was then used for immunoblotting as described herein. At least three independent experiments were analysed for retardation assays. The data is presented as mean±s.e.m.

1.7 Pull-Down Assay

Whole cell lysates from HEK-293T cells overexpressing LIPA constructs and exposed to blue light for 12 h, were extracted in lysis buffer containing (PBS-Tween 0.05%+ protease inhibitor, phosphatase inhibitor II, Phosphatase inhibitor III [Sigma] and PMSF). Samples were then lysed with a Dremel tissue homogenizer, at low intensity for 10 sec (BioSpec Products, Inc., Bartlesville, Okla.). Samples were sequentially centrifuged at 4° C. (500×g for 5 min, and 1000×g for 10 min). The supernatant was collected and 10% of the volume was kept as input sample and diluted in 4× Laemmli lysis buffer. The remaining supernatant incubated with 5 µg of anti-mCherry antibody for 30 min at 4° C. with rotation. During this incubation time, Dynabeads Protein G (Life technologies) were resuspended by tilting the vial several times for proper mixing of the beads with the solution. A volume of 70 µL (per 300 µL sample) of Dynabeads was transferred to clean microcentrifuge tubes, equilibrated 3 times (10 min) in 300 µL of PBS+0.05% Tween+protease inhibitors. Dynabeads were then resuspended with the antibody-sample mixture, and this mix was then incubated with rotation at 4° C. for 2 h. After incubation, tubes were placed on the magnet and the supernatant was discarded. Beads were then washed with the PBS+0.05% Tween+Protease inhibitors mixture 3 times (10 min) at 4° C. with rotation, removing the supernatant between washes. At the last wash, samples were transferred to a new clean microcentrifuge tube to avoid elution of proteins bound to the tube wall. Dynabeads were then eluted by resuspending beads in 50 µL of 2× Laemmli lysis buffer. Pull-down and input samples were heated at 95° C. for 10 min and samples were then subjected to Western blot analysis. At least three independent experiments were analysed for Pull-down assays.

1.8 Animals

Three-month-old C57/BL6 mice were obtained from Charles River Laboratories and remained seven days in habituation period, from their arrival to the CHUL of Québec City animal facility, before any handling or experiment. Mice were housed with a 12 h light/dark cycle and had food and water ad libitum. All animal experiments were approved by the Animal Welfare Committee of Université Laval, in accordance with the Canadian Council on Animal Care policy.

1.9 Transmission Electron Microscopy

HEK-293T cells overexpressing LIPA-Empty and LIPA-α-syn and exposed to blue light were fixed in 0.5 mL of 3.5% acrolein and 4% paraformaldehyde (PFA) in 0.05 M phosphate-buffered saline (PBS; pH 7.4), overnight at 4° C. Then, cells were washed three times in PBS to remove excess fixative. Cell pellets were mixed gently with 125 µL of 4% agarose, kept at 4° C. until solid, and then cut into 50 µm sections using a Leica VT1000S vibratome (Leica Biosystems, Concord, ON, Canada). Sections were washed 3 times in PBS for 10 min and were incubated in 1.5% potassium ferrocyanide and 2% aqueous osmium tetroxide in 0.1 M phosphate buffer (pH 7.4) for 1 hour at RT. After 5 washes with ddH2O for 3 minutes, sections were incubated 20 min in a fresh solution of thiocarbohydrazide (1% w/v) at room temperature then washed again 5 times with ddH2O for 3 minutes, incubated 30 min in 2% aqueous osmium tetroxide, and washed 5 times with ddH2O for 3 minutes. Sections were dehydrated using sequential alcohol baths followed by propylene oxide and embedded in Durcupa™ resin, infiltrated between ACLAR sheets overnight at room temperature, then polymerized in the oven at 55° C. for 3 days. Ultrathin sections (~65 nm) were generated using a Leica UC7 ultramicrotome. Images of 12-13 cells per experimental condition were randomly acquired at 9300× using a FEI Tecnai Spirit G2 transmission electron microscope (Thermo Fisher Scientific Company, Hillsboro, Oreg.) operating at 80 kV and equipped with a Hamamatsu ORCA-HR digital camera (10 MP).

1.10 Stereotaxic Injections of AAV Viral Particles and Implantation of Wireless Optogenetic Devices Three-month-old C57/BL6 mice were obtained from Charles River Laboratories and remained seven days in habituation period before any handling. Mice were housed with a 12 h light/dark cycle and had food and water ad libitum. All animal experiments were approved by the Animal Welfare Committee of Université Laval, in accordance with the Canadian Council on Animal Care policy.

Mice were anesthetized with 2% isoflurane-$O_2$ and placed in a stereotaxic frame (David Kopf Instruments). The top of the skull was incised with a scalpel and tissues were cleared to visualize the interaural point and the bregma. After piercing the skull with a drill, mice received a unilateral injection of 2 µL of viral suspension at the rate of 0.2 µL/minute, which corresponds to a total viral load of $2\times10^{10}$ GC, using automatic pumps (David Kopf Instruments). Injections were performed in the substantia nigra and in the neostriatum according the following coordinates, respectively: (−3.08 mm posterior, −1.5 mm lateral, −4.25 mm ventral) and (+0.2 mm posterior, −2 mm lateral, −3 mm ventral). Injections were made using a 10-µL syringe (Hamilton) and 30-gauge needle. Needle was placed to injection site 3 minutes before starting the injection and left for additional 5 min post-injection before it was slowly withdrawn. During the same surgery session, mice were implanted with wireless optogenetic devices (Eicom, USA) in the SNc or the neostriatum (Jeong et al., 2015), using the following coordinates, respectively: (−3.08 mm posterior, −1.5 mm lateral, −4.20 mm ventral) and (+0.2 mm posterior, −2 mm lateral, −3 mm ventral).

1.11 Immunohistochemistry/Immunofluorescence

Animals were sacrificed by ketamine/xylazine overdose (100 mg/mL, injected 0.1 mL/20 g mice) and brains were removed after transcardial perfusion with PBS then 4% PFA-PBS (50 mL each). Brains were post-fixed 4 h in 10 mL of 4% PFA, then incubated in 25% sucrose-PBS for 24 h. After post-fixation, brains were cut in coronal sections (30 µm thick) with a microtome (SM2000R; Leica) and slices were stored at −20° C. in cryoprotection medium.

For immunohistochemistry, slices were washed twice beforehand with PBS (10 min) and then incubated for 1 h in blocking buffer (Bb: 3% bovine serum albumin [BSA], 0.1% Triton™ X-100-PBS). After blocking, slices were incubated overnight at 4° C. with primary antibody in Bb:anti-tyrosine hydroxylase (TH; 1:1000; AB152 and AB318; Millipore), anti-human α-syn (1:1000; Syn1; BD Laboratories), anti-α-syn S129 phosphorylated (1:2000; pSyn; Wako), anti-ubiquitin (1:1000; Ubi; Dako), anti-p62 (1:1000; SQSTM1; Santa Cruz Biotechnology) or anti-HSP70 (1:1000; HSP 70/HSC 70 [H-300]; Santa Cruz Biotechnology). For immunofluorescence, slices were washed three times with Bb (10 min) and then incubated for 2 h at RT, with appropriate secondary antibodies conjugated to Alexa™ Fluor-488 or Alexa™ Fluor-633 (Invitrogen; diluted 1:1,000 in PBS containing 0.1% Triton™ X-100). After incubation with the secondary antibodies, slices were washed three times with PBS containing 0.1% Triton™ X-100, then incubated in DAPI-PBS (1:5000 for 7 min), and finally washed twice in PBS. For microscopic observations, slices were mounted on Superfrost™ Plus microscope slides (Fisherbrand) in aqueous mounting media (Fluoromount-G T, EMS) and allowed to dry in the dark for at least 2 days.

For enzymatic revelation, slices were incubated for 2 h at room temperature with biotinylated secondary antibody (1:200; Vector Laboratories), before exposure to 300 µL of 3,3'-diaminobenzidine tetrahydrochloride (DAB, Pierce) for 1 min, and subsequently counterstained with Nissl stain. Slides were then mounted on glass coverslips.

For the quantification of TH+ cell numbers in SN, slices were washed twice beforehand with PBS (10 min), then incubated at RT for 15 minutes in 0.1% $H_2O_2$-PBS. After 15 minutes, slices were washed three times with PBS (10 min), and then incubated at RT for 1 h in Bb. After blocking, slices were incubated overnight at 4° C. with primary antibody in Bb (see immunofluorescence above). Subsequently, slices were washed three times with Bb (10 min) and then incubated at RT for 2 h with appropriate biotinylated secondary antibody (1:500; Vector Laboratories) for DAB revelation reagent (Pierce). After incubation with secondary antibodies, slices were washed three times with PBS and then incubated with the VECTASTAIN' ABC kit (PK-6100; Vector Laboratories) for 1 h. After this incubation, slices were washed twice with PBS and then once with PBS containing 0.05 M Tris. Subsequently, slices were incubated in DAB solution (one DAB tablet in 20 mL of Tris 0.05 M, pH 7.6) about 1 min, until the appearance of staining, then slices were washed three times with PBS. For stereology experiments, slices were mounted on Superfrost™ Plus microscope slides (Fisherbrand), dried, and finally mounted in DTX Mounting Medium (13512, EMS) after dehydration of slices with 90% and 100% ethanol and immersion in CitriSolv™ solution (DECON).

1.12 Behavioural Tests

All behavioural tests were completed during the light phase of the light-dark cycle, i. e. between 8 am and 4 pm. Mice were habituated to the experimenter and the testing room for several days before starting the tests. The experimenter was blind to viral vector treatment during testing and blind to both vector group and illumination group during scoring and all group assignments were randomized.

The cylinder test: The cylinder test was performed to evaluate the motor impairment induced after a dopaminergic neuronal loss, by quantifying the deficits in using the contralateral forelimb (akinesia; Schallert et al., 2000; Oueslati et al., 2013; Oueslati et al., 2015). Briefly, mice were placed in a transparent Plexiglas cylinder (15 cm diameter, 12 cm high) surrounded by a mirror to monitor the mouse from all directions and videotaped using a camera (Microsoft LifeCam Cinema; H5D-00018). A total number of 30 forepaw contacts made on the cylinder wall by the ipsilateral or the contralateral (impaired) forelimbs were scored and the results were expressed as the ratio of contralateral contacts relative to the total contacts made by both forelimbs. Analysis was performed in a blinded fashion.

The Grip Strength test: Grip Strength (CHATILLON® DFE Series, USA) was used to measure the muscle strength of forelimbs as previously described (Meyer et al., 1979). During testing, the mouse is placed horizontally on the grid to allow gripping of the grid with the forepaws while being supported by the tail. Once the grid is gripped, the mouse is pulled back until the grip on the grid is released and then the value on the apparatus is recorded. Mice underwent three trials per testing session and analysis was performed on the average for the three trials.

The rotarod test: The rotarod test was used to measure motor coordination, endurance, and balance (Rozas et al., 1997). All mice were pre-trained on the rotarod (LE 8200, Panlab Harvard apparatus, USA) at baseline to reach a stable performance. At testing, mice were placed on the rotarod for three consecutive 3 min trials, at fixed speed (12 and 8 RPM) and accelerating speed (4-40 RPM in 2 minutes). Mice rested for 1 min between each trial at each speed. The latency to fall was recorded for each trial and the mean value from each speed and was used for analysis.

The gait test: To test for gait abnormalities, footprint gait analysis was performed as previously described (Fernagut et al., 2002) with some modifications. Briefly, the hind- and forefeet of the mice were painted with blue (right paws) and orange (left paws) nontoxic paint (Liquid tempera, SCHOLA) immediately prior to placement in a 45 cm long and 15 cm wide runway coated in newsprint paper. Stride length was measured as the distance of forward movement between paw prints for. The mean value of each set of three values measuring stride length was used in the analysis.

1.13 Unbiased Stereological Estimation of Dopaminergic Neurons in the SNc

Dopaminergic neuronal number was estimated using unbiased stereology, according to the optical fractionator principle described by West and colleagues (West et al., 1991). Briefly, the number of TH-immunoreactive neurons and Nissl-positive cells were determined every fourth coronal section (¼) covering the entire SNc structure. The SNc was delineated at low magnification (20×) and then the dopaminergic neurons were counted under an oil immersion objective (60×). DA neurons were counted in a blinded fashion and the results are expressed as the mean±standard error of the total number of TH+ neurons in the injected side. Analysis was performed using the MBF Stereo Investigator software (MBF Bioscience). The parameters used for the stereological analysis were as follows: grid size, 150×150 µm; counting frame, 75×75 µm; and 2 µm guard zones. Tissue thickness was determined at each counting field. The coefficient of error was <0.1.

1.14 Statistical Analysis

All cell-based assays were performed in at least three independent experiments. Statistical analysis was performed using one-way ANOVA followed by Tukey's multiple comparisons test. For analysis of behavioural data, statistics were performed using two-way ANOVAs followed by Tukey's post-hoc tests. Across time data was analyzed with a linear mixed-effects model of viral vector and implant. Within-subjects variance was controlled for by including random effects of intercept and slope for each mouse. The model was estimated using maximum likelihood and contrast comparisons were performed to determine the effect of viral vector and implants at each time point. Analyses were performed using RStudio™ version 3.4.1 with nlme version 3.1-131. All values were expressed as the means±s.e.m. and the software used for the statistical analysis was Prism v.6 (GraphPad, La Jolla, Calif., USA).

TABLE 1

Antibodies used in this study

| Antigen | Antibody name/catalog number | Epitope | Source |
|---|---|---|---|
| α-syn | Syn1/610787 | 15-123 | BD |
| Human α-syn | α-synuclein (211)/sc-12767 | 121-125 | Santa Cruz Biotechnology |
| α/β/γ-synuclein | Syn FL-140/sc-10717 | | Santa Cruz Biotechnology |
| pS129 α-Syn | Wako/pSyn #64 | 124-134 | Wako |
| Ubiquitin | Ubiquitin/Z0458 | | Dako |
| P62 | SQSTM1(D-3)/sc-28359 | 151-440 | Santa Cruz Biotechnology |
| HSP70 | HSP 70/HSC 70 (H-300) sc-33575 | 342-641 | Santa Cruz Biotechnology |

TABLE 1-continued

Antibodies used in this study

| Antigen | Antibody name/catalog number | Epitope | Source |
|---|---|---|---|
| mCherry | mCherry/ab167453 | | Abcam |
| GFP | GFP Antibody (4B10B2) [HRP]/ NBP2-22111H | | Novus Biologicals |
| Beta-actin | β-actin/G043 | | abm (Applied Biological Materials) |
| Secondary Antibodies | | | |
| | 680RD-conjugated goat anti-rabbit | | LI-COR Biosciences |
| | 800RD-conjugated goat anti-rabbit | | LI-COR Biosciences |
| | 680RD-conjugated goat anti-mouse | | LI-COR Biosciences |
| | 800RD-conjugated goat anti-mouse | | LI-COR Biosciences |

Example 2

Engineering of Light-Inducible Protein Aggregation (LIPA) System

Protein aggregation is a process by which misfolded proteins adopt an organized and structurally well-defined fibrillar conformation, leading to the formation of proteinaceous amyloid deposits. This process occurs via a nucleation-propagation polymerization mechanism, also called "seeding effect", whereby small oligomers, or seeds, provide a template for the assembly of soluble monomer proteins into highly ordered protein aggregates defined by their insolubility and β-sheet structure (Oueslati et al., 2014). One example is the accumulation of proteinaceous intraneuronal inclusions, called Lewy bodies (LB), in the brain of patients suffering from alpha-synucleinopathies (Knowles et al., 2014; Lashuel et al., 2013), a group of neurological disorders which encompasses Parkinson's disease (PD), PD with dementia (PDD), dementia with Lewy bodies (DLB), and multiple system atrophy (MSA) (Fares et al., 2016; McCann et al., 2014). These inclusions are predominantly composed of aggregated alpha-synuclein (α-syn), a small protein ubiquitously and abundantly expressed in the brain (Lashuel et al., 2013; Spillantini et al., 1997).

Since their initial description more than a century ago (Goedert et al., 2013), a causal link between LB formation and neurotoxicity in PD and related disorders has been suggested. However, the exact role of LB in the pathogenesis and progression of PD and how these α-syn-rich inclusions precipitate neuronal death remains hypothetical. This in part due to the fact that current cellular and animal models of PD and α-syn overexpression do not allow to monitor the α-syn aggregation process in living cells and do not result in the formation of intraneuronal inclusions that more closely resemble actual LB observed in the brains of PD-disease patients. Accordingly, there is need for improved cellular and animal models enabling the study of protein aggregation in living cells, particularly models in which the protein aggregates more closely resemble those found in vivo in patients suffering from proteinopathies.

In the present study, a versatile system employing optogenetic methodologies was engineered to permit the spatiotemporal control of protein aggregation (e.g., α-syn aggregation and LB formation) in living cells in vitro and in vivo. This system, herein referred to as light-inducible protein aggregation (LIPA), is based on the use of engineered photoreceptors that change their conformation in response to light stimuli, and thereby influence the functional output of proteins when fused together, notably the induction of protein clustering. More specifically, the approach is based on the use of a mutant form of the *Arabidopsis thaliana* photoreceptor cryptochrome 2 (CRY2), also referred to as CRY2olig (Taslimi et al., 2014). When stimulated with blue light, mutant CRY2 undergoes rapid, reversible, and robust protein clustering.

Figure 2:
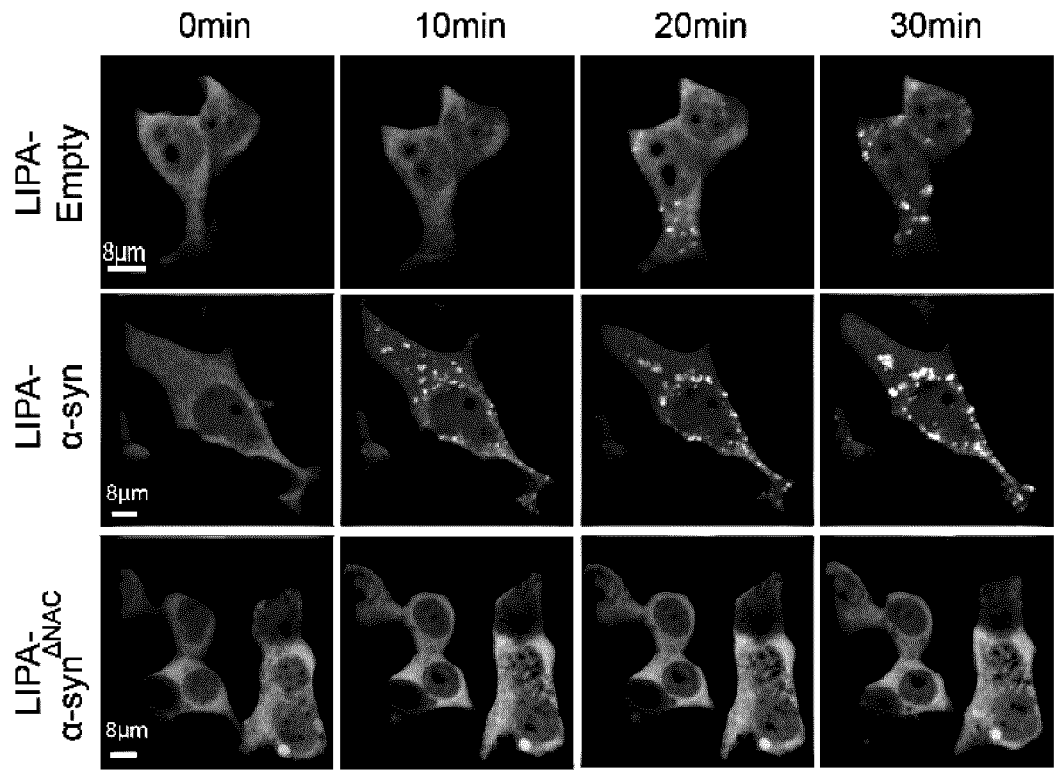
FIG. 2 shows a time-lapse live imaging illustration of representative HEK-293T cells overexpressing the LIPA system.
Figure 3:
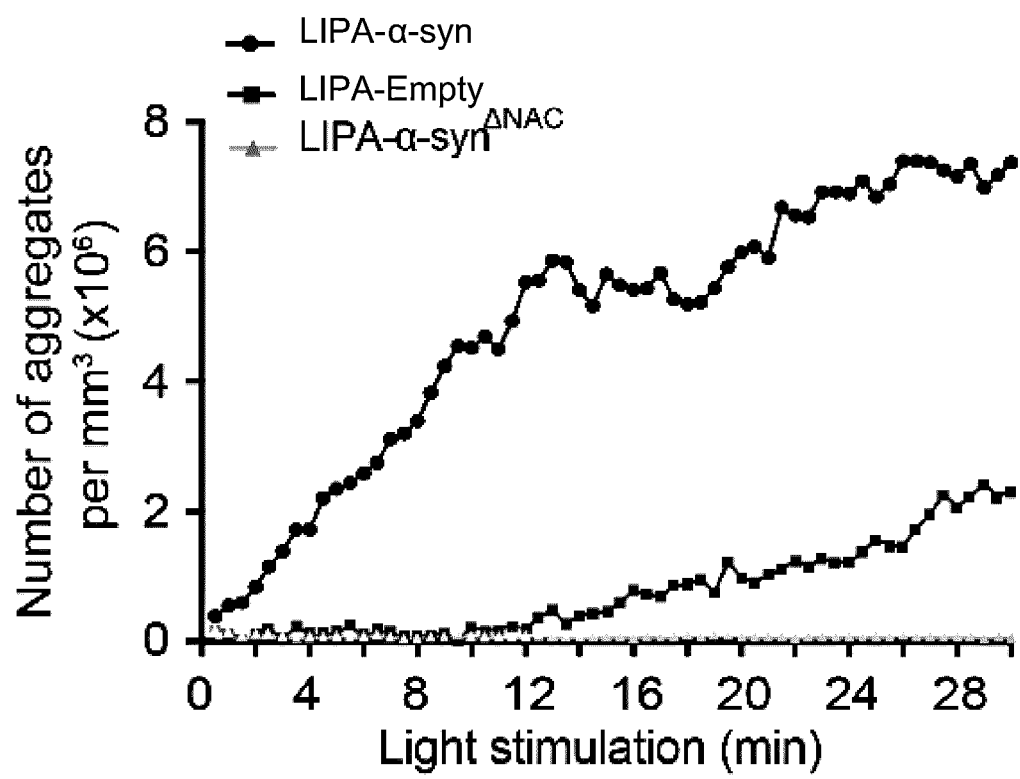
FIG. 3 shows an analysis of the number of LIPA system-induced aggregates per volume of cells after 0 to 30 min stimulation with a confocal 488 nm laser (1% intensity=15.5 µW).

A construct was engineered in which the human α-syn gene was fused to the CRY2 and mCherry (LIPA-α-syn) coding regions (FIG. 1). The constructs expressing CRY2-mCherry (LIPA-Empty) and CRY2-mCherry fused to a non-aggregatable form of α-syn missing the NAC region (residues 71 to 82) (Giasson et al., 2001) referred to herein as LIPA-α-syn', were used as controls (FIG. 1). Live imaging analysis revealed that cells overexpressing LIPA-Empty and LIPA-α-syn, but not those expressing LIPA-α-syn', undergo a rapid and robust formation of protein inclusions following exposure to laser illumination (488 nm; 15.5 µW), suggesting that the presence of non-aggregatable form of α-syn precludes light-induced LIPA clustering (FIGS. 2 and 3). Remarkably, the presence of α-syn enhanced LIPA aggregation and LIPA-α-syn inclusions appeared within seconds of a light pulse, compared to LIPA-Empty inclusions which occurred 10-12 min after light stimulation, suggesting the active role of α-syn in prompting CRY2 light-induced responses (FIGS. 2 and 3). Furthermore, the number of aggregates per cell volume, as well as the volume of aggregates per se, increased dramatically in cells overexpressing LIPA-α-syn, compared to the LIPA-Empty condition, suggesting that the presence of α-syn may prompt CRY2 light-induced responses.

Figure 4:
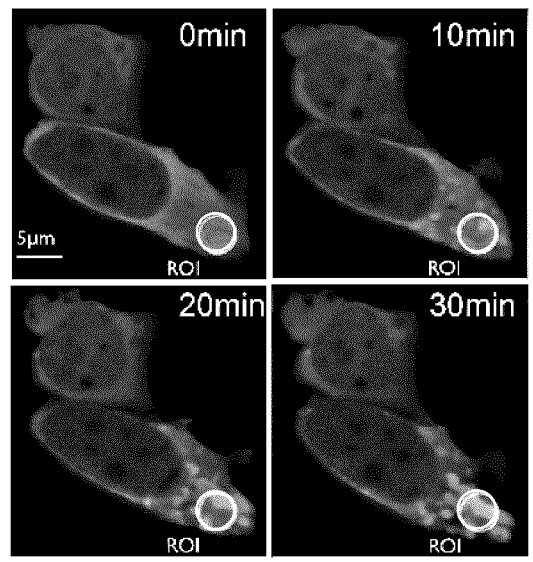
FIG. 4 shows a time-lapse live imaging illustration of representative region of interest (ROI) light stimulation in HEK-293T cells overexpressing LIPA-α-syn.
Figure 5:
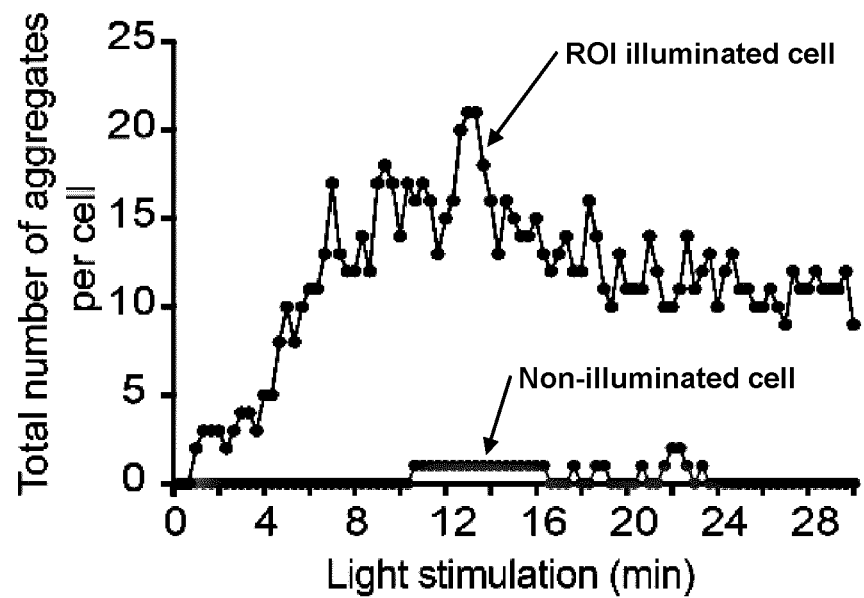
FIG. 5 shows an analysis of the total number of LIPA-α-syn aggregates per cell after ROI stimulation.

Moreover, the system allowed focal induction of LIPA-α-syn aggregation within the cytoplasm of a single cell, reflecting the high spatial resolution of the LIPA system (FIGS. 4 and 5). Local light stimulation of LIPA-α-syn in the cytosol of HEK-293T cells was induced and live imaging analysis showed the formation of LIPA-α-syn inclusions exclusively under the stimulated region of interest (ROI) (FIGS. 4 and 5). These inclusions increased in number and volume over time and spread from the stimulation site to the rest of the cytosol.

Example 3

Figure 6:
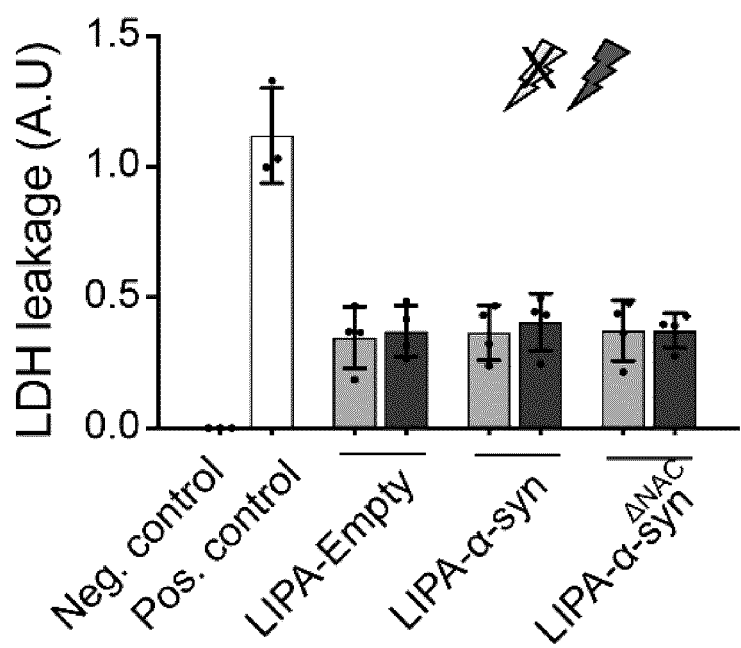
FIG. 6 shows the results of a cell toxicity assay in which cell death was assessed by quantifying the extracellular release of cytosolic lactate dehydrogenase (LDH) spectrophotometrically using a colorimetric assay. The results indicate that neither overexpression of LIPA constructs, nor the exposure to the blue light, were toxic in the experimental design employed herein.

LIPA System Induces Long-Term Protein Inclusions Upon Prolonged Light Stimulation In pathological conditions, α-syn aggregates and LBs are present in the brain for long periods of time. Consequently, the long-term LIPA system-induced aggregation in HEK-293T cells was monitored by assessing the proportion of mCherry-positive cells with aggregates at different time points over 24 h of illumination. Cells were stimulated with blue LED light at the intensity of 0.8 mW/cm², a condition that was not observed to induce cell toxicity (FIG. 6).

Figure 7:
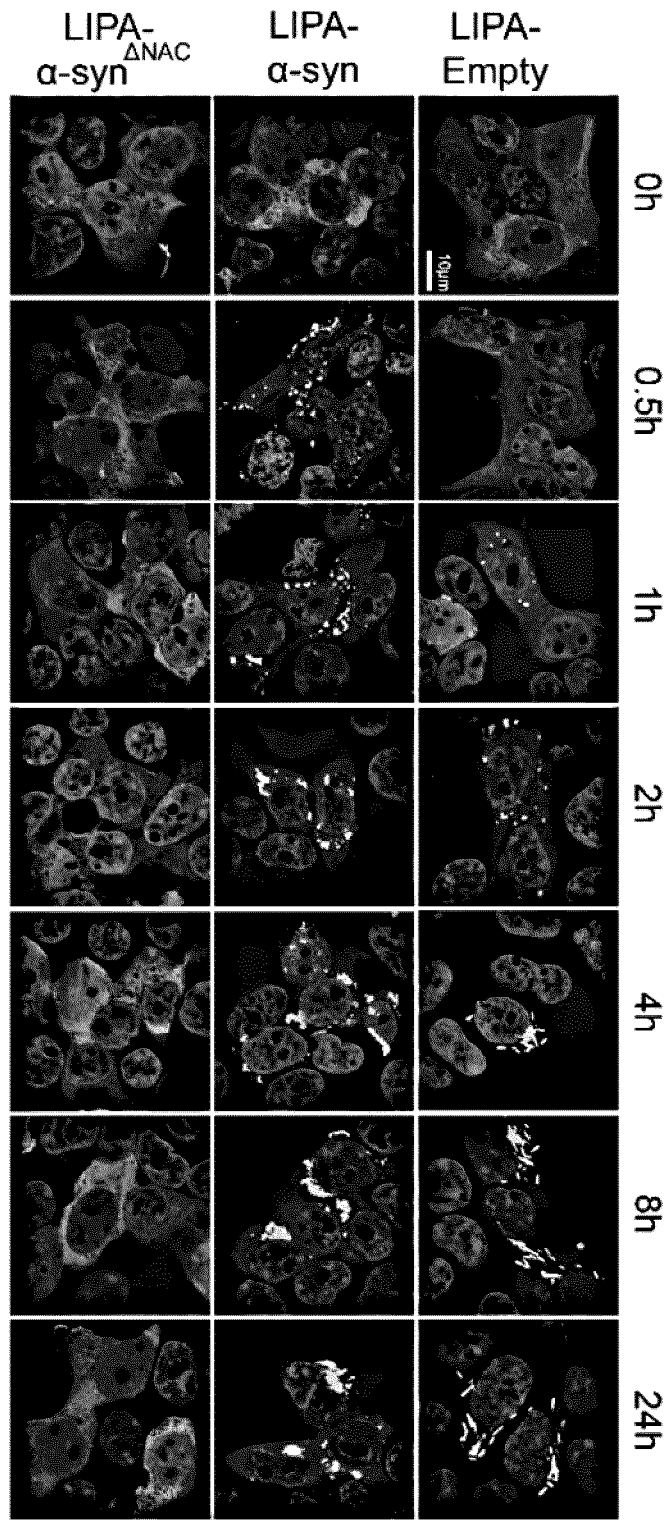
FIG. 7 shows representative confocal images of HEK-293T cells overexpressing each of the LIPA system constructs (LIPA-α-syn$^{\Delta NAC}$LIPA-α-syn, LIPA-Empty) and exposed to blue light for 0 to 24 h.
Figure 8:
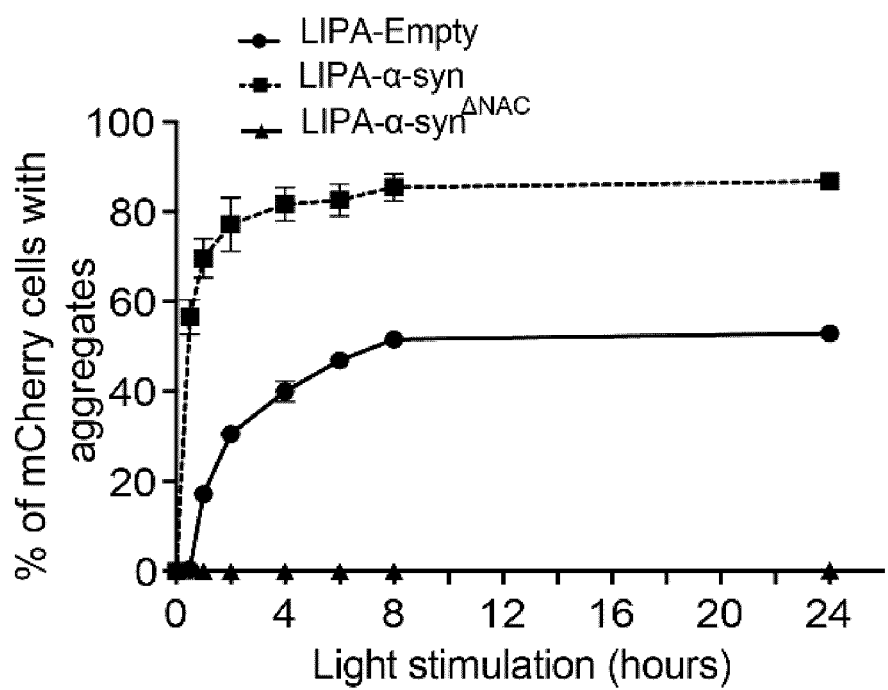
FIG. 8 shows an analysis of the percentage of mCherry-positive cells exhibiting LIPA aggregates (n=5).

Quantification revealed that the proportion of mCherry-positive cells overexpressing LIPA-Empty and exhibiting intracellular inclusions increased with time upon light stimulation and reached a maximum of 50% of cells with aggregates after 8 h of illumination, which remained stable (plateau) for at least 24 h (FIGS. 7 and 8). Notably, cells overexpressing the LIPA-α-syn construct exhibited a more rapid formation of mCherry inclusions, as the number of cells positive for LIPA inclusions reached 60% in less than 30 min, plateauing (80%) after 6 h, where they remained stable after 24 h of light stimulation (FIGS. 7 and 8). Cells overexpressing LIPA-α-syn$^{\Delta NAC}$ did not exhibit apparent inclusions, despite prolonged light stimulation. These results suggest that the non-aggregatable form of α-syn either precludes the LIPA aggregation process or induces small and discrete inclusions undetectable (e.g., by confocal microscopy) (FIGS. 7 and 8).

Example 4

α-Syn Dictates Morphology of LIPA System-Induced Protein Inclusions

A closer look at the morphology of the inclusions revealed that LIPA-α-syn aggregates are relatively round-shaped, whereas LIPA-Empty inclusions adopted a needle-like shape, suggesting that the presence of α-syn dictates morphological aspects of the inclusions (FIG. 9).

Figure 10:
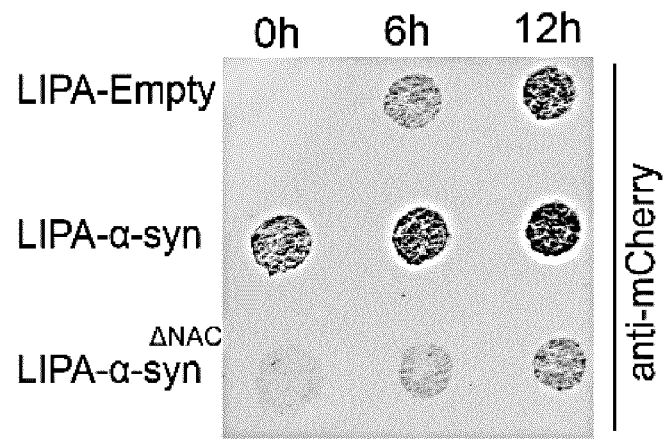
FIGS. 10 and 11 show the results of a filter retardation assay and dot blot analysis showing the time course of LIPA-Empty and LIPA-α-syn aggregate formation (n=3).
Figure 11:
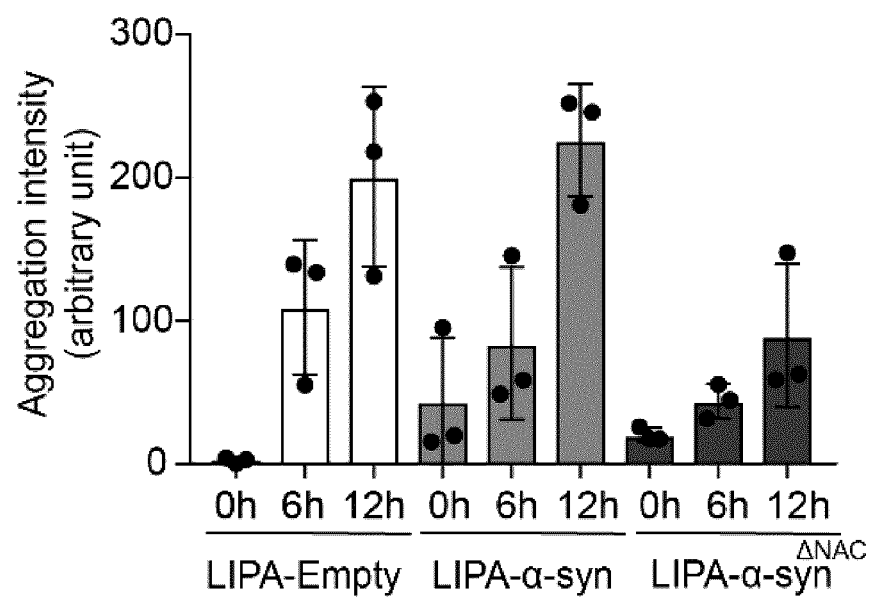
Figure 12:
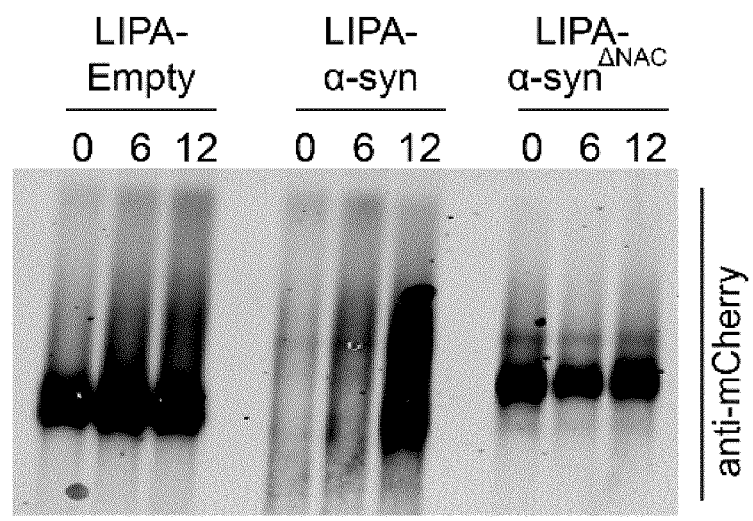
FIGS. 12 and 13 show the results of a semi-denaturing detergent agarose gel electrophoresis (SDD-AGE) exhibiting the time-dependent formation of high-molecular LIPA-Empty and LIPA-α-syn aggregates after 0, 6, or 12 h exposure to blue light (n=3).
Figure 13:
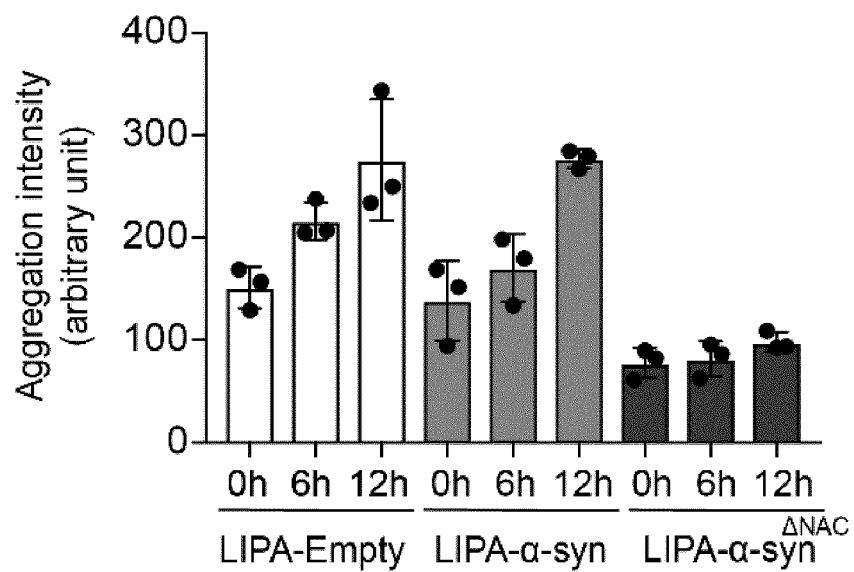

At the biochemical level, filter retardation assay confirmed that light stimulation of LIPA-Empty and LIPA-α-syn resulted in an apparent time-dependent accumulation of insoluble aggregates (FIGS. 10 and 11). This observation was corroborated using semi-denaturing detergent agarose gel electrophoresis (SDD-AGE) (FIGS. 12 and 13).

Example 5

LIPA System Generates Stable α-Syn Aggregates After Transient Light Stimulation

The presence of α-syn fused to the LIPA system was associated with a dramatic increase in aggregation rate and a distinctive inclusion morphology (see Examples 2-4), suggesting that α-syn may play a leading role in driving protein aggregation. Given that light-induced aggregation of LIPA-Empty is reversible (with inclusions rapidly dissociating in the dark; Taslimi et al., 2014), the experiments described below were performed to investigate whether α-syn fused to CRY2 could maintain protein aggregation and inclusion formation after the cessation of light stimulation.

Figure 14:
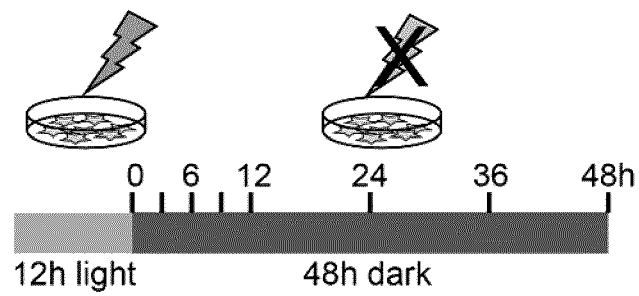
FIG. 14 shows a schematic representation of the experimental paradigm used in FIGS. 15-21.

The stability of LIPA-α-syn inclusions in the absence of light stimulation was evaluated by assessing the proportion of mCherry-positive cells having inclusions. LIPA aggregates were allowed to form over a 12 h period under light stimulation and cells were collected at different time points up to 48 h post-illumination (FIG. 14).

Figure 15:
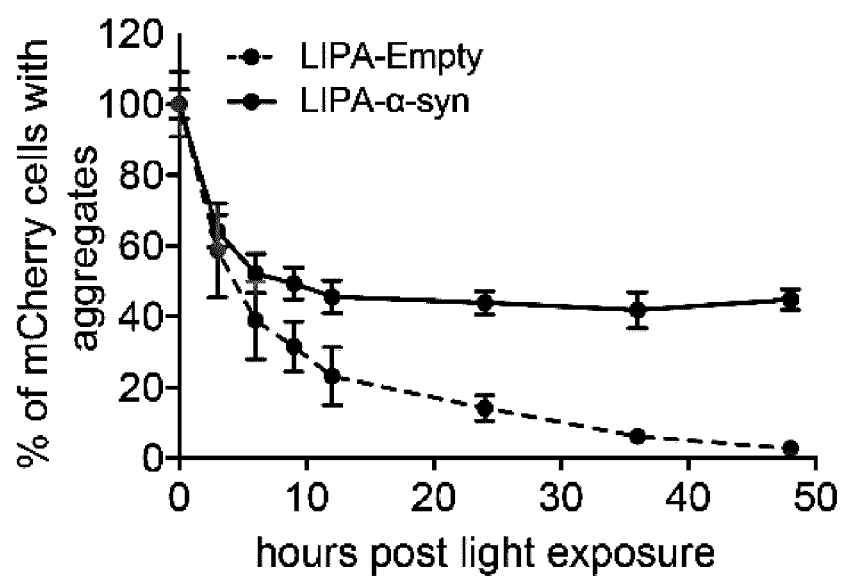
FIG. 15 shows an analysis of the time course of LIPA-Empty or LIPA-α-syn aggregates dissociation/disappearance, after 12 h pre-exposure to the blue light, by assessing the proportion of mCherry-positive cells exhibiting inclusions (n=5).

In accordance with previous observations (Taslimi et al., 2014), the percentage of cells with LIPA-Empty aggregates dropped consistently, and virtually no cells exhibited aggregates 48 h post-light exposure (FIG. 15). However, the percentage of mCherry-positive cells with LIPA-α-syn aggregates only partially decreased (from 80% to 50%) 3 h following light stimulation, and then stabilized, reaching a plateau of 40% between 6 h and 48 h (FIG. 15).

These results suggest that the presence of α-syn is associated with the lingering LIPA-α-syn aggregates once light-stimulation has ceased, implying that a transient exposure to the blue light is sufficient to trigger the formation of stable and self-perpetuating α-syn aggregates.

Example 6

Figure 16:
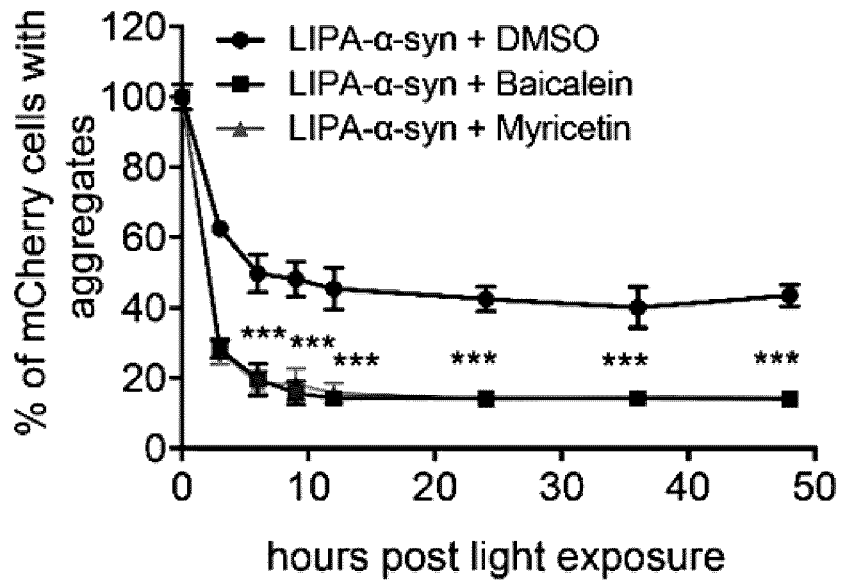
FIG. 16 shows the effect of treatment with the small molecule inhibitors of α-syn aggregation, baicalein and myricetin, on the stability of LIPA-α-syn aggregates (n=5).
Figure 17:
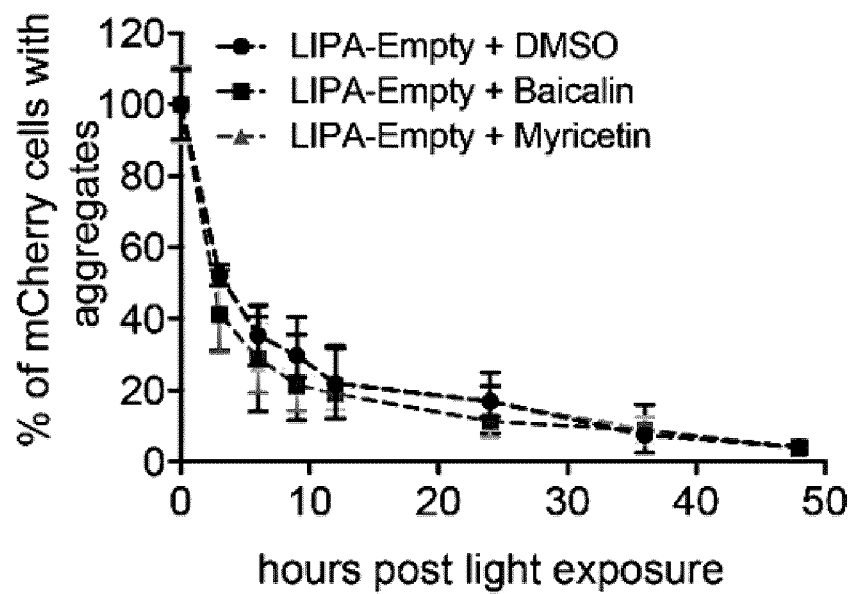
FIG. 17 shows the effect of treatment with baicalein and myricetin on the stability of LIPA-Empty aggregates (n=5).
Figure 18:
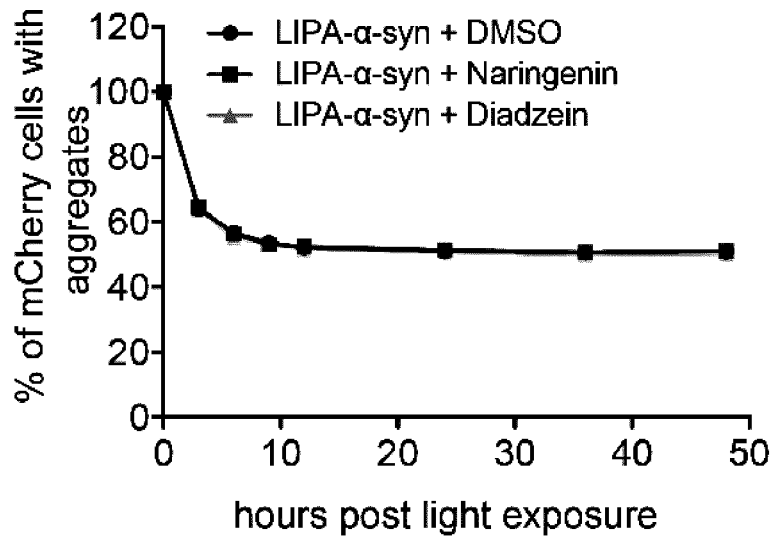
FIG. 18 shows the effect of treatment with inactive small molecules, naringenin and diadzein, on LIPA-α-syn aggregates stability (n=5).

Inhibitors of α-Syn Aggregation Reduce the Proportion of Cells with LIPA-α-Syn Inclusions The impact of treatment with potent small molecule inhibitors of α-syn aggregation, namely baicalein and myrecitin (Masuda et al., 2006; Zhu et al., 2004), on the stability of LIPA-α-syn inclusions was next evaluated. Quantification revealed a 50% reduction in the number of cells exhibiting stable LIPA-α-syn inclusions, demonstrating that inhibition of α-syn aggregation reduces inclusion stability (FIG. 16). Treatment with baicalein or myrecitin had no effect on LIPA-Empty dissociation, confirming the specificity of these inhibitors (FIG. 17). Moreover, treatment with inactive small molecules, naringenin and daidzein (Masuda et al., 2006), did not affect the proportion of cells with mCherry inclusions (FIG. 18), suggesting a role of α-syn in maintaining LIPA inclusions in the dark.

Figure 19:
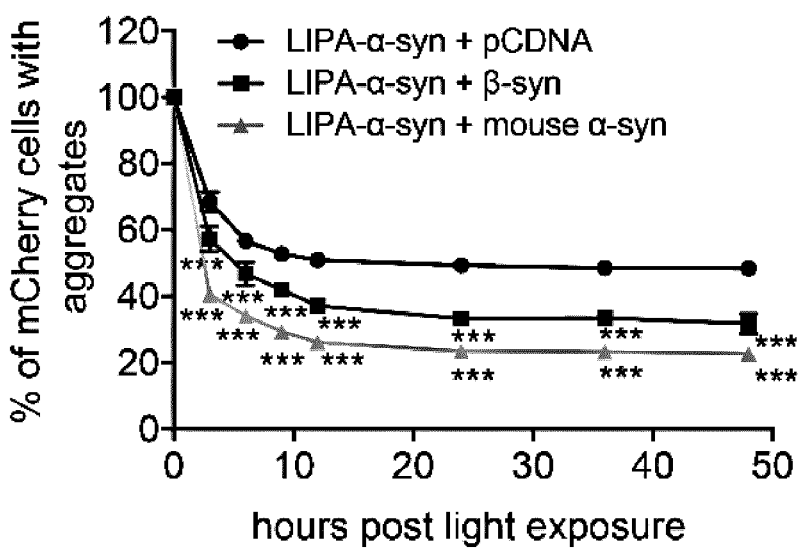
FIG. 19 shows the effect of beta-synuclein (β-syn) and mouse α-syn overexpression on the stability of LIPA-α-syn aggregates (n=5).
Figure 20:
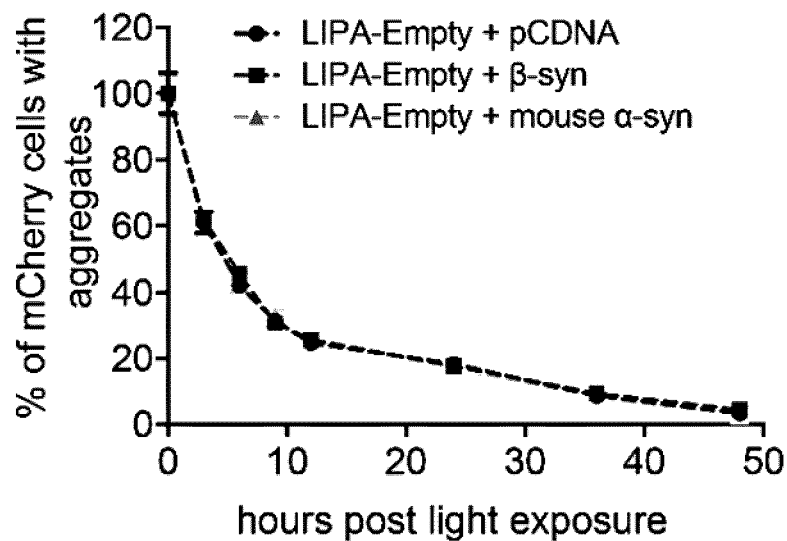
FIG. 20 shows the effect of β-syn and mouse α-syn overexpression on the stability of LIPA-Empty aggregates (n=5).
Figure 21:
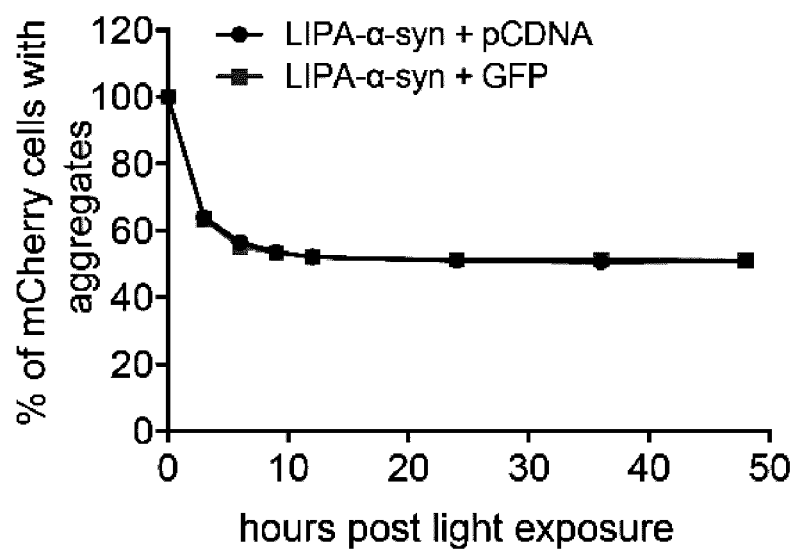
FIG. 21 shows the effect of GFP overexpression on the stability of LIPA-α-syn aggregates (n=5).

Previous studies have reported that both β-synuclein (β-syn) and mouse α-syn (ma-syn) overexpression inhibit human α-syn aggregation in cell culture and animal models. To test the impact of these two proteins on LIPA-α-syn inclusion formation, LIPA-α-syn was overexpressed with β-syn or ma-syn in HEK-293T cells, then transiently exposed to blue light for 12 h. Post-stimulation analysis showed a significant reduction of the proportion of cells exhibiting mCherry aggregates in the presence of β-syn or ma-syn (FIG. 19) for LIPA-α-syn inclusions, but not for LIPA-empty inclusions (FIG. 20) or when LIPA-α-syn was overexpressed with GFP (FIG. 21).

Collectively, the above results show that treatment with pharmacological or genetic inhibitors of α-syn aggregation results in a reduction in the proportion of cells with LIPA-α-syn inclusions, further suggesting a central role of α-syn in maintaining aggregation self-perpetuation.

Example 7

LIPA System Initiates Self-Perpetuating α-Syn Aggregates After Transient Light Stimulation The maintenance and the auto-perpetuation of α-syn aggregates depends on self-amplification through the recruitment of soluble proteins, a process known as seeding (Oueslati et al., 2014). To investigate if LIPA-α-syn is able to recruit and seed the aggregation of endogenous monomeric α-syn, a pull-down assay was performed for LIPA-α-syn inclusions overexpressed in the presence of monomeric α-syn-GFP.

Figure 22:
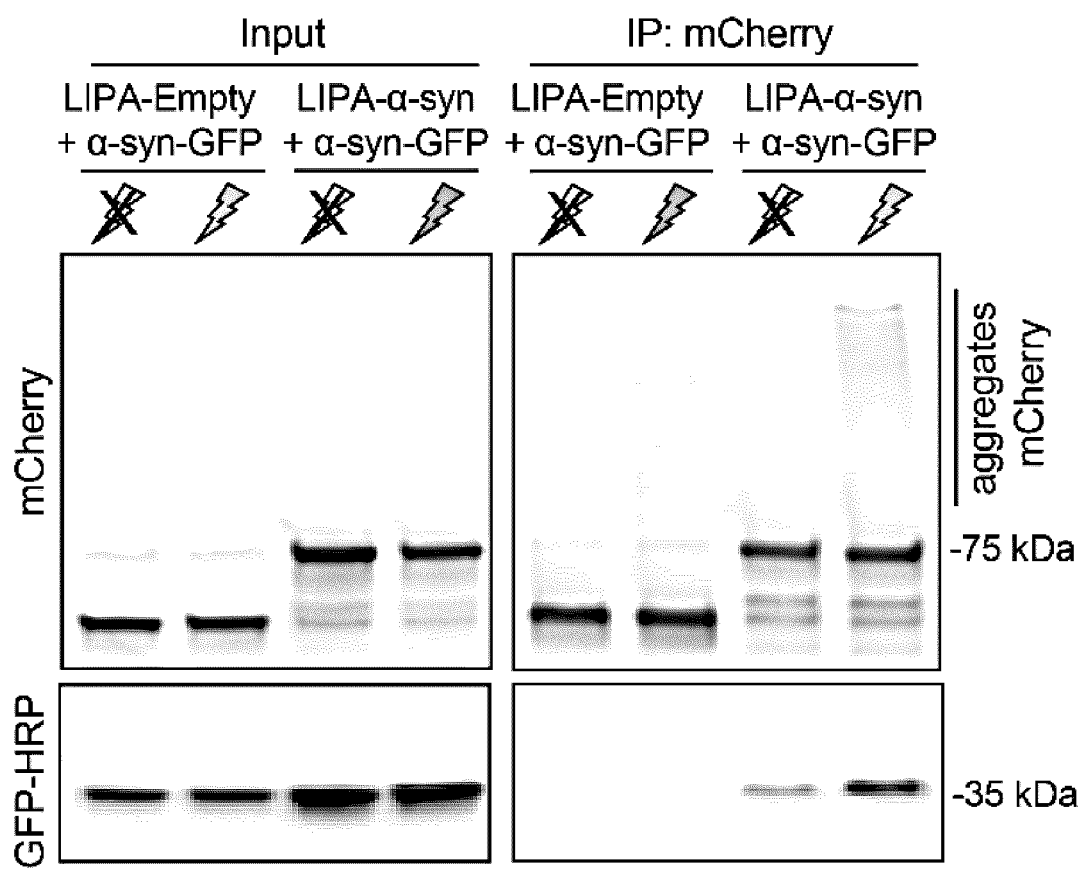
FIG. 22 shows the results of co-immunoprecipitation (IP) of LIPA-α-syn aggregates with monomeric α-syn-GFP (n=3).

Western blot analysis revealed the presence of an α-syn-GFP band that co-immunoprecipitated with LIPA-α-syn aggregates under the illuminated condition (+light), in contrast to the weak α-syn-GFP signal detected in the non-illuminated condition (−light; FIG. 22), suggesting that LIPA-α-syn aggregates can recruit monomeric α-syn-GFP. No α-syn-GFP signal was observed after LIPA-Empty pull-down (+/−light), suggesting that the seeding effect is specific to LIPA-α-syn (FIG. 22). Moreover, immunocytochemistry analysis confirmed the seeding effect of LIPA-α-syn aggregates and revealed co-localization of LIPA-α-syn and α-syn-GFP signals, where LIPA-α-syn forms the core of the aggregates surrounded by recruited α-syn-GFP monomers (FIG. 23).

Additionally, the seeding capacity of LIPA-α-syn was confirmed in living cells using exogenous synthetic α-syn preformed fibrils (Pffs) tagged with Alexa™ 488 and assimilated by cells overexpressing LIPA-α-syn. Twelve hours after light exposure, co-localization of LIPA-α-syn aggregates with α-syn Pffs could be observed (FIG. 24), demonstrating that light-induced α-syn aggregates recruited synthetic α-syn fibrils.

Example 8

Figure 25:
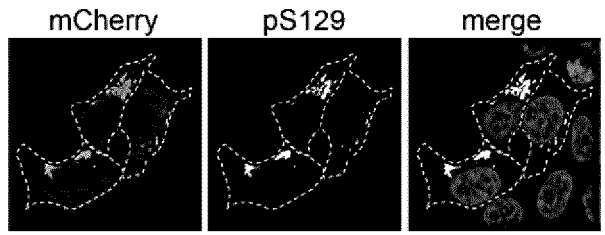
FIGS. 25-29 show representative confocal images of HEK-293T cells overexpressing LIPA-α-syn and exposed to light for 12 h and stained with authentic LBs markers: Phosphorylated α-syn at S129 (pS129.
Figure 26:
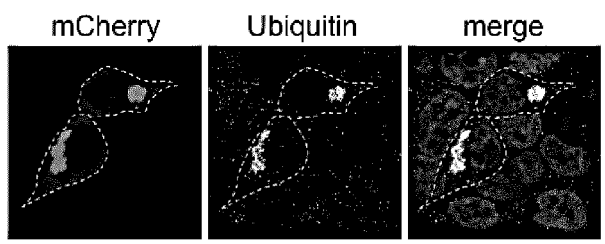
Figure 27:
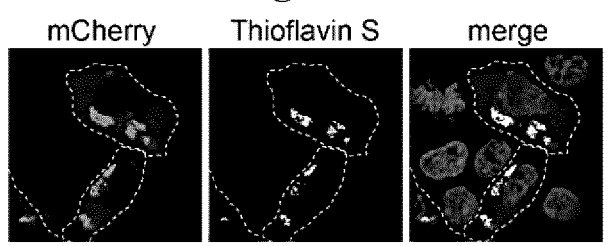
Figure 28:
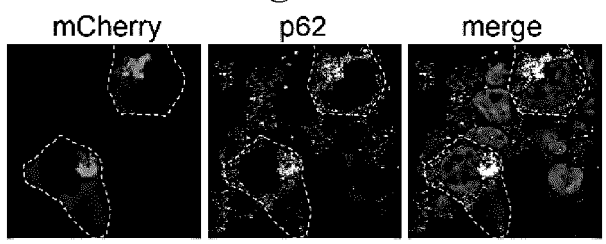
Figure 29:
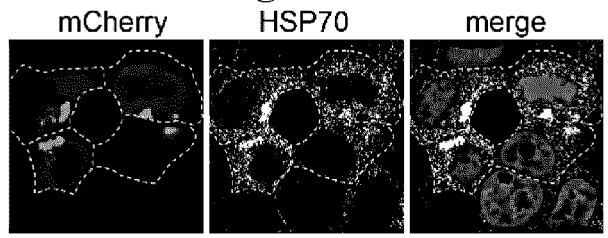

LIPA-α-Syn-Induced Inclusions Exhibit Features of Authentic Lewy Bodies in Cell Culture It was next investigated whether LIPA-α-syn inclusions reproduced key features of authentic LBs as observed post-mortem in α-synucleinopathy-diseased brains (Shults et al., 2006). Immunostaining of HEK-293T cells overexpressing LIPA-α-syn and exposed to light for 12 h revealed a complete co-localization of mCherry and α-syn signals within the LIPA-α-syn inclusions, demonstrating that α-syn is the main constituent of these deposits (data not shown). Moreover, LIPA-α-syn inclusions were positive for phosphorylated α-syn at Ser129 (pS129; FIG. 25) and ubiquitin (FIG. 26), two neuropathological hallmarks of authentic LBs. Staining with thioflavin S (ThS), an amyloid-specific dye, revealed that LIPA-α-syn inclusions contained β-sheets (FIG. 27), a structural characteristic of authentic LBs. Finally, LIPA-α-syn inclusions were also positive for p62 (FIG. 28) and HSP70 (FIG. 29), two chaperone proteins commonly observed within LBs in α-synucleinopathy-diseased brains. Neither inclusions nor LB-associated markers were observed in non-illuminated cells (data not shown).

Figure 30:
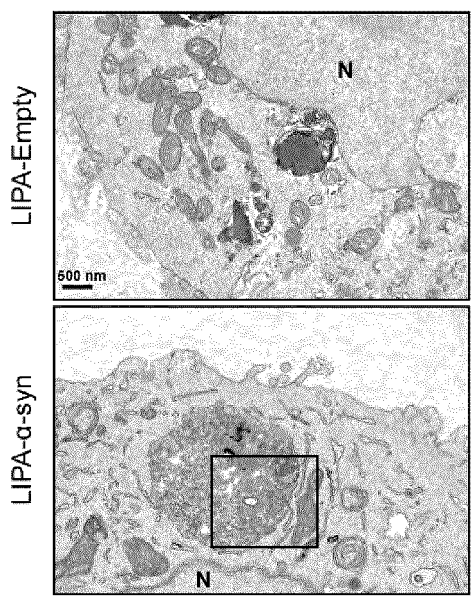
FIG. 30 shows transmission electron microscope images of representative HEK-293T cells exhibiting LIPA-Empty and LIPA-a-syn aggregates, after 12 h of light stimulation.
Figure 31:
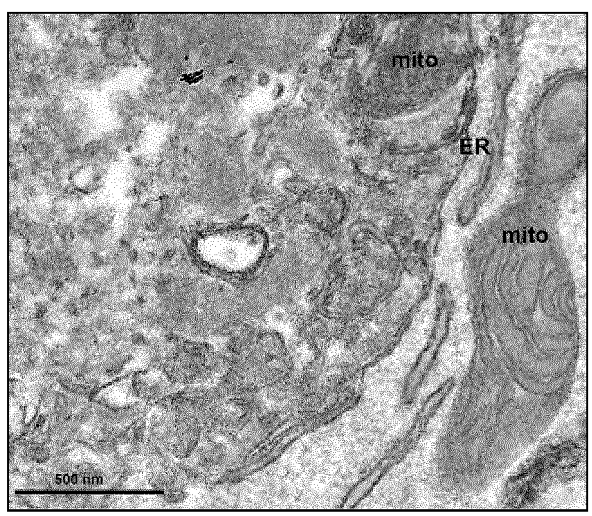
FIG. 31 shows a magnified transmission electron microscope image (black box in FIG. 30) showing the presence of mitochondria (mito) and endoplasmic reticulum (ER) within a LIPA-α-syn aggregate. Scale bar=500 nm.

The ultrastructure of LIPA aggregates was examined by transmission electron microscopy (TEM) analysis which revealed that LIPA-Empty aggregates appear as small electron dense inclusions, whereas LIPA-α-syn inclusions exhibit larger electron-dense core inclusions (FIG. 30). TEM analyses also revealed the presence of different organelles exclusively within the LIPA-α-syn aggregates (mitochondria, endoplasmic reticulum) suggesting that these aggregates interact with and sequester intracellular organelles (FIG. 31).

Example 9

LIPA-α-Syn-Induced Inclusions Exhibit Features of Authentic Lewy Bodies In Vivo

Figure 32:
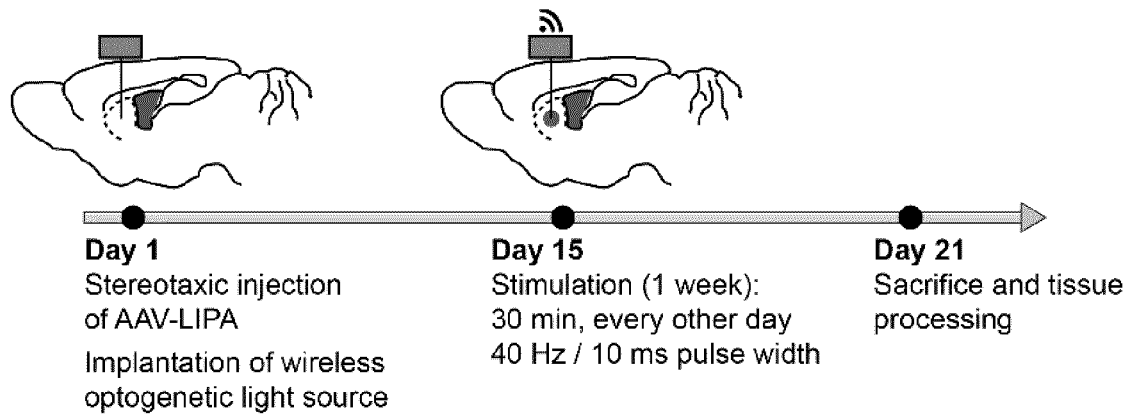
FIG. 32 shows the experimental design of the overexpression and the induction of LIPA-α-syn aggregation in the brain of wild type mice.

The ability of LIPA-α-syn system to induce LB-like inclusion formation in vivo was evaluated. An adeno-associated virus (AAV) gene delivery system was used to over-express LIPA-α-syn directly in the substantia nigra of wild-type mice. Fifteen days post-injection, intracerebral light stimulation was performed using an implantable wireless optogenetic device (Eicom; Jeong et al., 2015), for 30 min every other day, for a period of 7 days (FIG. 32), using non-toxic illumination parameters that did not induce any cell loss (data not shown).

Figure 33:
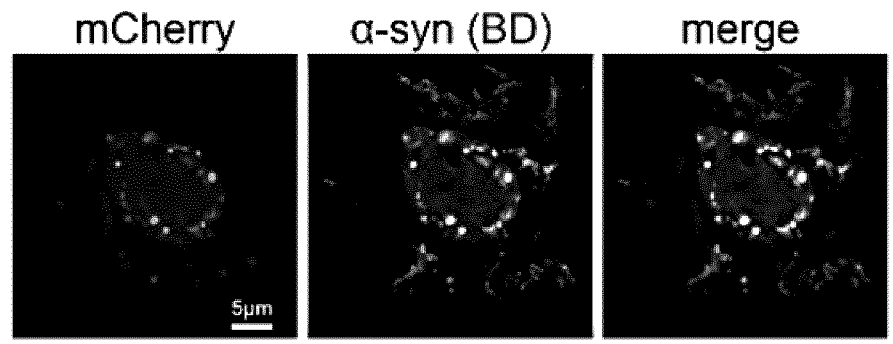
FIGS. 33-38 shows confocal microscope images of representative striatal neurons with LIPA-α-syn aggregates exhibiting authentic LBs markers: α-syn (BDlab and FL140.
Figure 34:
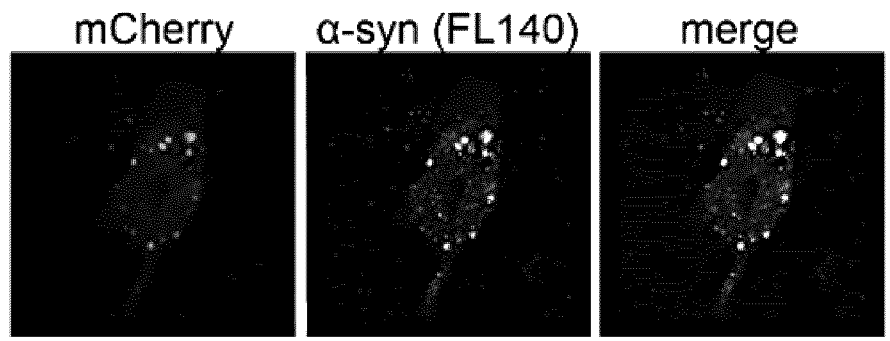
Figure 35:
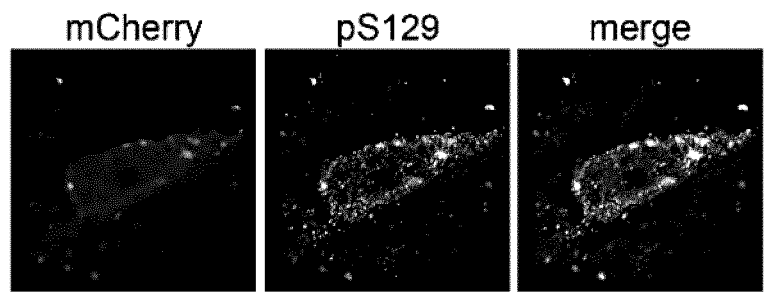
Figure 36:
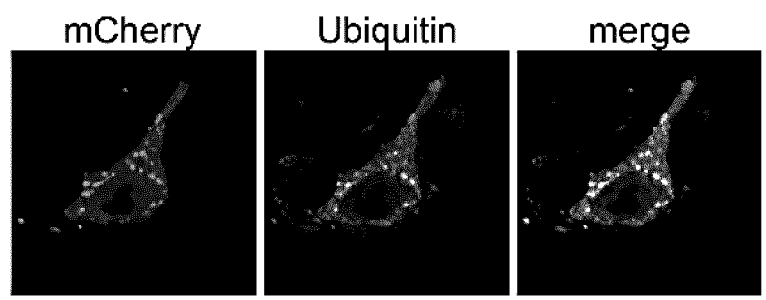
Figure 37:
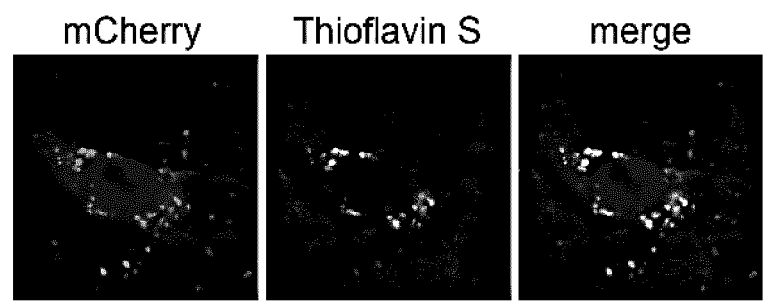
Figure 38:
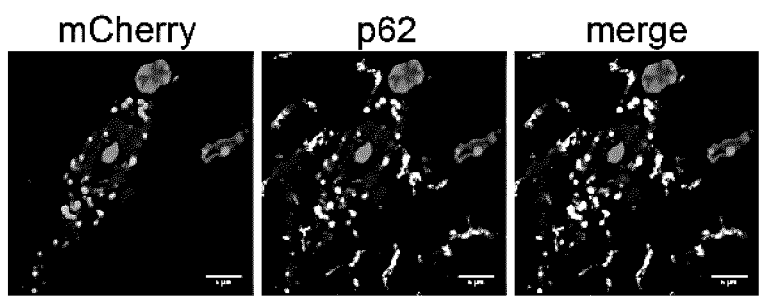

Post mortem-analysis revealed the presence of mCherry-positive inclusions within striatal neurons after light stimulation, whereas the brains of non-stimulated animals were completely devoid of such inclusions. Immunohistochemistry using anti-α-syn antibodies (Syn1 and FL140) demonstrated that α-syn is a major constituent of these aggregates (FIGS. 33 and 34). LIPA-α-syn inclusions were phosphorylated at the residue Ser129 (FIG. 35), ubiquitinated (FIG. 36), and exhibited β-pleated sheet content that was positive for ThS staining (FIG. 37). Finally, LIPA-α-syn inclusions were positive for p62 (FIG. 38).

To verify the possibility of inducing LBs-like inclusions in other brain regions using the present LIPA system, LIPA-α-syn was overexpressed in midbrain neurons and protein aggregation was stimulated with the same parameters used for the striatal stimulation. Immunohistochemistry analysis revealed the formation of LIPA-α-syn inclusions that exhibited many of the principal features of authentic LBs in midbrain neurons, including phosphorylation at residue Ser129, ubiquitination, the presence of β-pleated sheets positive for ThS staining, and LIPA-α-syn inclusion positive for p62 (data not shown).

Example 10

Figure 45:
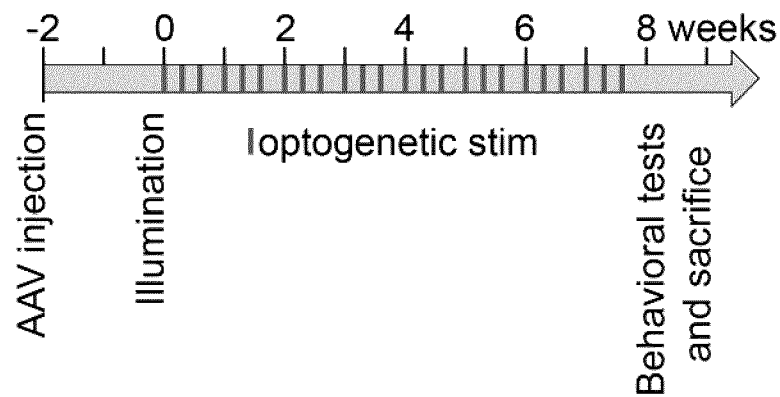
FIG. 45 shows a schematic representation of the in vivo experimental paradigm for FIGS. 46-53.
Figure 46:
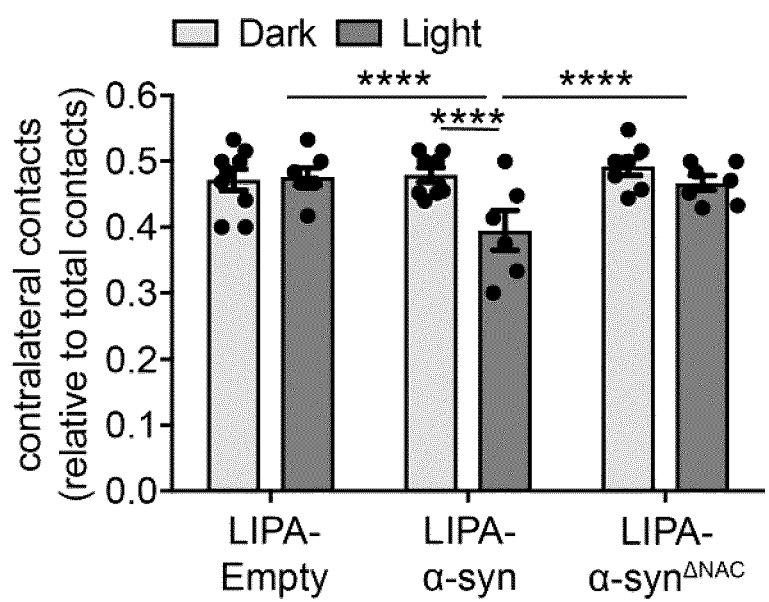
FIGS. 46-49 shows the results of assessments of behavioral impairment induced after overexpression of LIPA constructs, with and without optogenetic stimulation, using the cylinder test (FIG. 46), the grip strength test (FIG. 47), the rotarod test (FIG. 48), and the gait test (FIG. 49) (n=5-9 mice per experimental condition).
Figure 47:
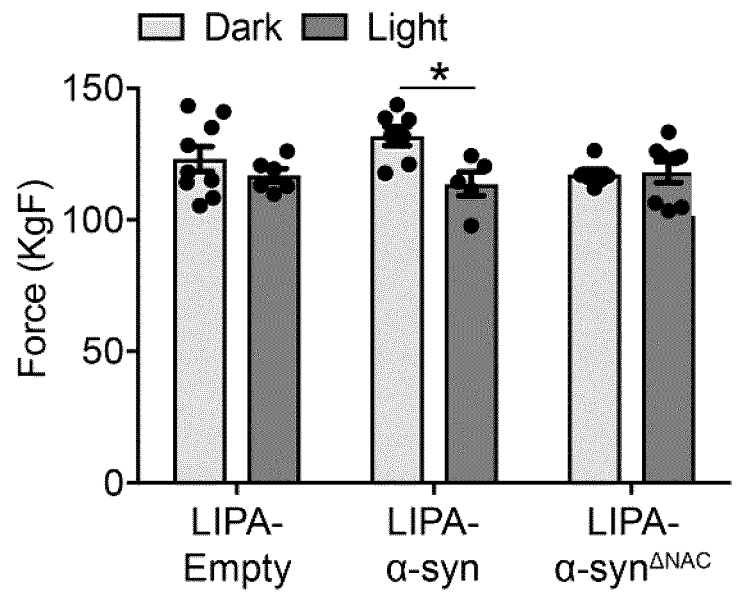
Figure 48:
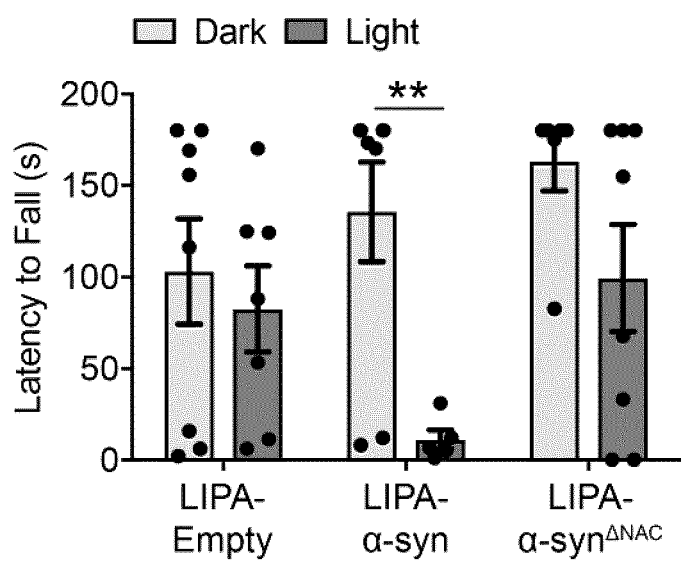

LIPA-Induced α-Syn Inclusions Precipitate Dopaminergic Neuronal Loss and Induce Parkinsonian-Like Motor Impairment In Vivo The behavioral and cellular effects of long-term induction of LIPA-α-syn aggregation in the midbrain of mice overexpressing LIPA constructs was evaluated to determine whether α-syn aggregation and LBs-like formation could impact the integrity of dopaminergic (DA) neurons. LIPA constructs were delivered in the substantia nigra using AAV gene delivery system. Two weeks post-injection, α-syn aggregation was stimulated for 1 h every other day, during 8 weeks, using a wireless implantable optogenetic device (FIG. 45). LIPA constructs were overexpressed at non-toxic levels, to specifically assess the toxicity induced by α-syn aggregation and to rule out any DA toxicity caused by overexpression of the constructs per se.

Figure 49:
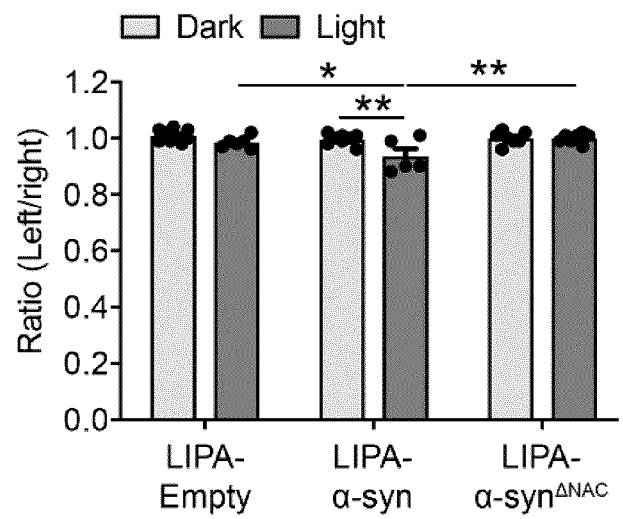

A battery of motor tests revealed that overexpression of the three LIPA constructs, in absence of light stimulation, did not induce any motor impairment (FIG. 46-49). Interestingly, when aggregation was induced by the blue light, only animals overexpressing LIPA-α-syn showed behavioral impairment, including a significant asymmetry in the use of contralateral forepaw in the cylinder test (FIG. 46), a significant reduction of grip strength test (FIG. 47) and a problem of coordination, reflected by the reduction of the latency time on the rotarod (FIG. 48) and gait abnormalities (FIG. 49).

Figure 50:
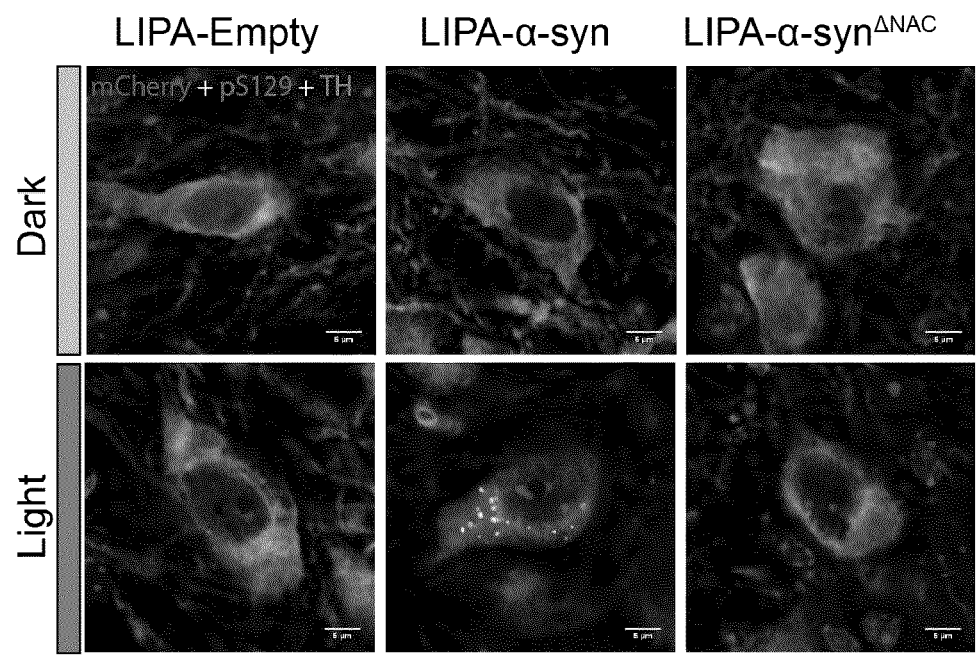
FIG. 50 shows confocal microscopy images illustrating the expression of LIPA-constructs in the dopaminergic midbrain neurons and the presence of pathological (pS129-positive) α-syn aggregates in LIPA-α-syn-positive and optogenetically stimulated neurons.
Figure 51:
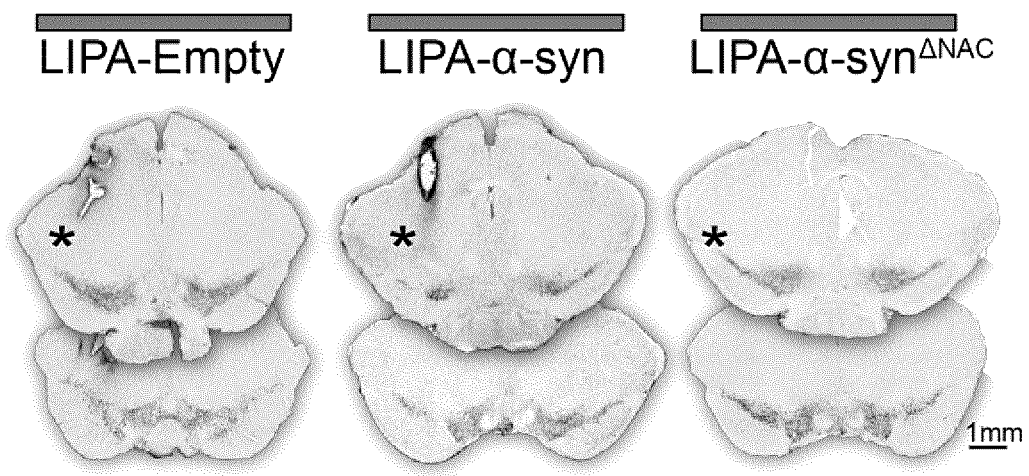
FIG. 51 shows microscope images illustrating the dopaminergic neuronal loss in the midbrain of mice overexpressing LIPA constructs and exposed to the blue light stimulation (*injected side; scale bar=1 mm).
Figure 52:
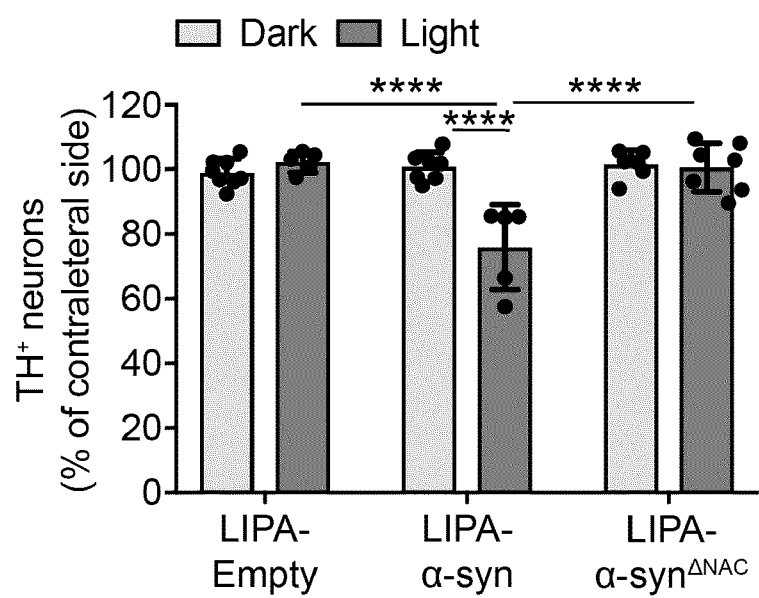
FIGS. 52 and 53 show stereological quantification of the TH-positive dopaminergic neurons (FIG. 52) and total neuronal marker (Nissl.
Figure 53:
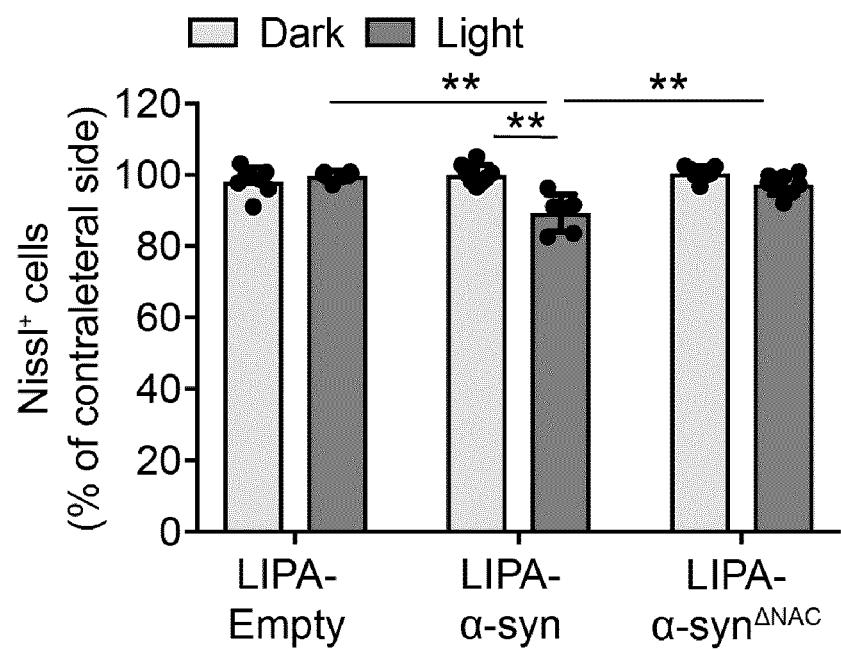

At the cellular level, the presence of protein aggregates was confirmed in the midbrain of mice overexpressing LIPA-empty and LIPA-α-syn, but not in LIPA-α-syn$^{\Delta NAC}$ (FIG. 50). Moreover, only DA neurons overexpressing LIPA-α-syn exhibited pathogenic pS129-α-syn aggregates (FIG. 50). Unbiased stereological quantification revealed that overexpression of LIPA constructs did not affect DA neuronal viability (FIGS. 51 and 52). However, after optogenetic stimulation, only mice overexpressing LIPA-α-syn exhibited a significant loss of the DA neurons, compared to non-stimulated LIPA-α-syn and to stimulated LIPA-Empty and LIPA-α-syn$^{\Delta NAC}$ (FIGS. 51 and 52). In LIPA-α-syn illuminated condition, Nissl positive midbrain neuronal quantification confirmed that TH-positive neuronal loss was indeed due to neurodegeneration rather than a loss of the DA phenotype (FIG. 53).

Collectively, these results suggest that the induction of LIPA-α-syn aggregation precipitates the DA neuronal loss and induces parkinsonian-like motor impairment.

Example 11

LIPA-α-Syn Co-Aggregates with Mutant Huntingtin and Promotes its Propagation in the Central Nervous System It was next investigated whether if LIPA-α-syn can co-aggregate with the pathological form of the protein Htt (mHtt) (harboring 75 poly-glutamine [poly-Q] repetition) and propagate in the mouse brain in a prion-like manner. This experiment aimed at studying the potential role α-syn in the pathogenesis of different proteinopathies or neurodegenerative diseases by potentiating the aggregation and the toxicity of different proteins implicated in these disorders, such as huntingtin (Htt) in Huntington's disease.

Briefly, LIPA-α-syn-mCherry and mHtt-GFP were co-overexpressed in HEK-293T cells and exposed to the blue light for 24 h, to allow protein co-aggregation. Light-induced aggregates were then extracted as described by Sanders and colleagues (Sanders et al., 2014) and injected stereotaxically in the striatum of 3-month-old wild type C57/Bl6 mice (n=3). One-month post-injection, animals were sacrificed and the expression of LIPA-α-syn and mHtt-GFP were analyzed in the brain.

Figure 54A:
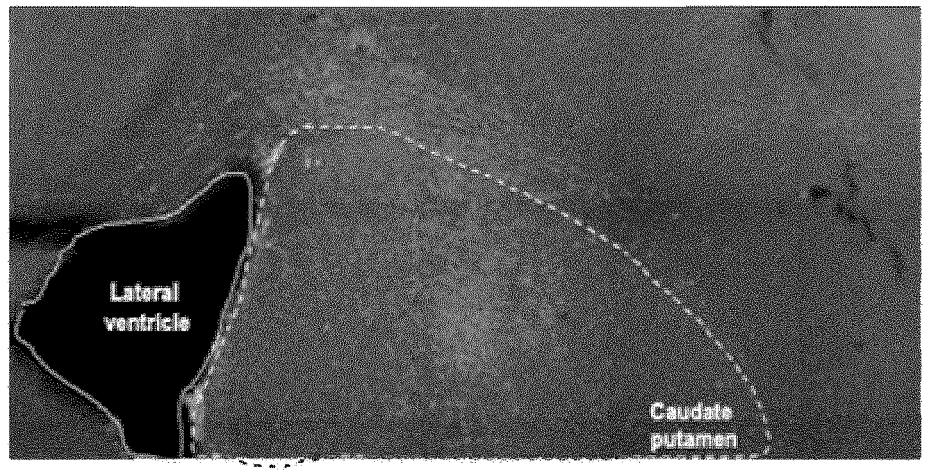
Figure 54B:
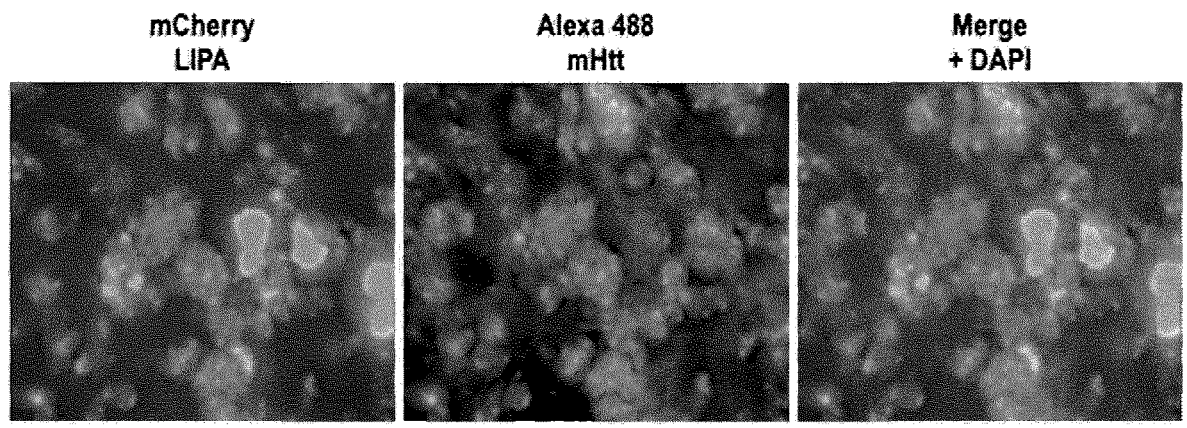

FIG. 54A shows that LIPA-α-syn (red; mCherry) and mHtt-GFP (Green; Alexa 488) aggregates are present in the injected striatum, one-month post-injection. Moreover, high resolution confocal imaging revealed that the two proteins co-localize within the majority of the striatal neurons, demonstrating that the two proteins co-aggregate in vivo and the aggregates are stable for at least one month in vivo (FIG. 54B).

Figure 54C:
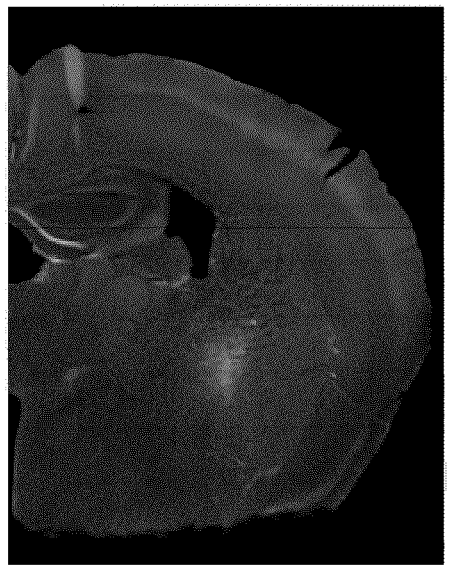
Figure 54D:
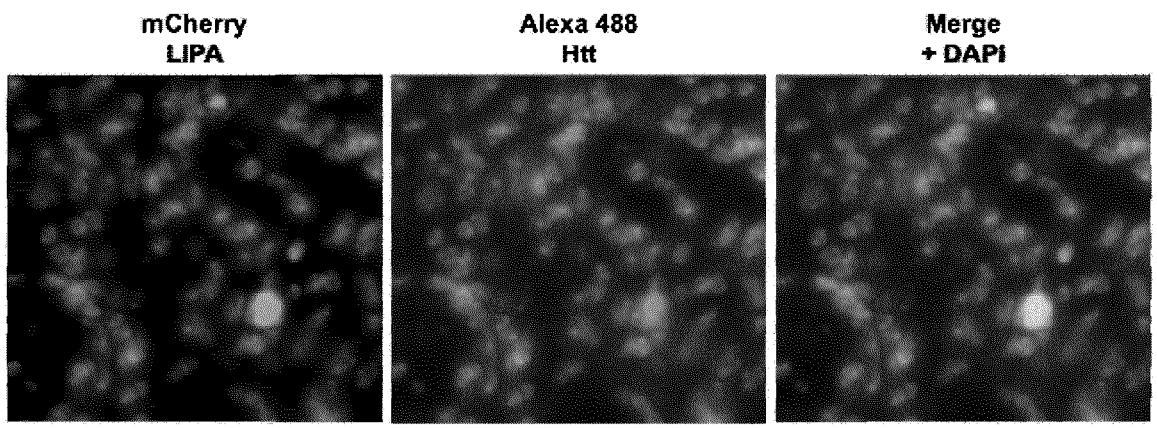

Analysis of other brain regions revealed the presence of LIPA-α-syn and mHtt-GFP co-aggregates in the globus pallidus (FIGS. 54C and 54D) and the entopendocular nucleus (FIGS. 54E and 54F), two brain nuclei synaptically connected to the striatum. These results demonstrate that LIPA-α-syn and mHtt aggregates can propagate from the injection site, in the striatum, to other brain regions.

Collectively, data presented herein demonstrate that α-syn can co-aggregate with mHtt and promote its propagation in the central nervous system, thereby providing direct experimental evidence on how α-syn can participate in Huntington's disease pathogenesis. Moreover, the results presented herein suggest the utility of the LIPA system described herein to study α-syn co-aggregation with other pathological proteins, as well as to better understand and to decorticate the pathophysiology of different proteinopathies or neurodegenerative disorders.

REFERENCES

Fares M. B. et al., "Induction of de novo alpha-synuclein fibrillization in a neuronal model for Parkinson's disease". *Proc Natl Acad Sci USA* 113, E912-921 (2016).

Fernagut, P. O. et al., "A simple method to measure stride length as an index of nigrostriatal dysfunction in mice." *J Neurosci Methods* 113, 123-130 (2002).

Giasson B. I. et al., "A hydrophobic stretch of 12 amino acid residues in the middle of alpha-synuclein is essential for filament assembly." *J Biol Chem* 276, 2380-2386 (2001).

Goedert M. et al., "100 years of Lewy pathology". *Nat Rev Neurol* 9, 13-24 (2013).

Jeong J. W. et al., "Wireless optofluidic systems for programmable in vivo pharmacology and optogenetics". *Cell* 162, 662-674 (2015).

Khamo J. S. et al., "Applications of optobiology in intact cells and multicellular organisms." *J Mol Biol* 429, 2999-3017 (2017).

Kim B. and Lin M. Z., "Optobiology: optical control of biological processes via protein engineering." *Biochem Soc Trans* 41, 1183-1188 (2013).

Knowles T. P. et al., "The amyloid state and its association with protein misfolding diseases". *Nat Rev Mol Cell Biol* 15, 384-396 (2014).

Lashuel H. A. et al., "The many faces of alpha-synuclein: from structure and toxicity to therapeutic target". *Nat Rev Neurosci* 14, 38-48 (2013).

Masuda M. et al., "Small molecule inhibitors of alpha-synuclein filament assembly". *Biochemistry* 45, 6085-6094 (2006).

McCann H. et al., "alpha-Synucleinopathy phenotypes". *Parkinsonism Relat Disord* 20 Suppl 1, S62-67 (2014).

Meyer O A et al. "A method for the routine assessment of fore- and hindlimb grip strength of rats and mice". *Neurobehav Toxicol*, 1: 233-236 (1979).

Oueslati A. et al., "Protein transmission, seeding and degradation: key steps for alpha-synuclein prion-like propagation". *Exp Neurobiol* 23, 324-336 (2014).

Oueslati, A. et al., "Polo-like kinase 2 regulates selective autophagic alpha-synuclein clearance and suppresses its toxicity in vivo". *Proc Natl Acad Sci USA* 110, E3945-3954 (2013).

Oueslati, A. et al., "Photobiomodulation suppresses alpha-synuclein-induced toxicity in an AAV-based rat genetic model of Parkinson's disease". *PLoS One* 10, e0140880 (2015).

Rozas, G. et al., "An automated rotarod method for quantitative drug-free evaluation of overall motor deficits in rat models of parkinsonism". *Brain Res Brain Res Protoc* 2, 75-84 (1997).

Schallert, T. et al., "CNS plasticity and assessment of forelimb sensorimotor outcome in unilateral rat models of stroke, cortical ablation, parkinsonism and spinal cord injury". *Neuropharmacology* 39, 777-787 (2000).

Shults C. W., "Lewy bodies". *Proc Natl Acad Sci USA* 103, 1661-1668 (2006).

Spillantini M. G. et al., "Alpha-synuclein in Lewy bodies". *Nature* 388, 839-840 (1997).

Stefani M. and Dobson C. M., "Protein aggregation and aggregate toxicity: new insights into protein folding, misfolding diseases and biological evolution". *J Mol Medicine* 81, 678-699 (2003).

Taslimi A. et al., "An optimized optogenetic clustering tool for probing protein interaction and function". *Nat Commun* 5, 4925 (2014).

West, M. J. et al., "Unbiased stereological estimation of the total number of neurons in the subdivisions of the rat hippocampus using the optical fractionator". *Anat Rec* 231, 482-497 (1991).

Zhang K. and Cui B, "Optogenetic control of intracellular signaling pathways." *Trends Biotechnol* 33, 92-100 (2015).

Zhu M. et al., "The flavonoid baicalein inhibits fibrillation of alpha-synuclein and disaggregates existing fibrils". *J Biol Chem* 279, 26846-26857 (2004).

The invention claimed is:

1. A light-induced protein aggregate comprising:
(a) a fusion protein comprising an alpha-synuclein polypeptide fused to a photoactivatable polypeptide; and
(b) a proteopathic polypeptide other than alpha-synuclein that self-aggregates under pathogenic conditions,
wherein illumination of the photoactivatable polypeptide with light having a wavelength sufficient for photoactivation triggers irreversible formation of intracellular protein aggregates comprising the fusion protein and the proteopathic polypeptide.

2. The light-induced protein aggregate of claim 1, wherein the intracellular protein aggregates remain stable for at least 5 h post-illumination.

3. The light-induced protein aggregate of claim 1, wherein the intracellular protein aggregates remain stable for at least 2 days post-illumination.

4. The light-induced protein aggregate of claim 1, wherein one or more of the photoactivatable polypeptide, the alpha-synuclein, and the proteopathic polypeptide, are fused to a detectable marker.

5. The light-induced protein aggregate of claim 4, wherein the detectable marker is a fluorescent protein, a reporter enzyme, a transcription factor, a radioisotope binding protein, or a bioluminescent protein.

6. The light-induced protein aggregate of claim 1, which is comprised in a cell stably transfected or infected with a polynucleotide encoding the fusion protein, and a polynucleotide encoding the proteopathic polypeptide.

7. The light-induced protein aggregate of claim 1, which is comprised in a transgenic rodent, non-human primate, fish, nematode, yeast, or fly engineered to express the fusion protein and the proteopathic polypeptide.

8. The light-induced protein aggregate of claim 1, which has seeding or self-propagating activity with respect to the proteopathic polypeptide.

9. The light-induced protein aggregate of claim 1, wherein the proteopathic polypeptide is, comprises, or is from huntingtin.

10. The light-induced protein aggregate of claim 1, wherein the proteopathic polypeptide is, comprises, or is from: an Aβ precursor protein, an Aβ peptide, Tau, a prion, an Ig light chain, serum amyloid A, transthyretin, cystatin C, beta-2-microglobulin, apolipoprotein AI, apolipoprotein AII, gelsolin, amylin, calcitonin, atrial natriuretic factor, lysozyme, insulin, fibrinogen α-A chain, superoxide dismutase 1, an androgen receptor, an ataxin, a TATA box-binding protein, or TDP-43.

11. The light-induced protein aggregate of claim 1, wherein the photoactivatable polypeptide is, comprises, or is from: a photoreceptor, a cryptochrome, a phytochrome, cryptochrome 2 (CRY2), light-oxygen-voltage (LOV) domains, CRY2-CIB1 (calcium and integrin-binding protein 1) variants, CRY2E490G, CRY2clust, iLID nano and iLID micro, LOVTRAP, Magnets, cobalamin binding domain CBD, VfAU1-LOV, CPH1S, or BphP1-PpsR2.

12. The light-induced protein aggregate of claim 1, which is produced in and extracted from a cell, a rodent, a non-human primate, a fish, a nematode, yeast, or a fly.

13. A light-inducible intracellular protein aggregation system, the system comprising a cell comprising:
(a) a fusion protein comprising an alpha-synuclein polypeptide fused to a photoactivatable polypeptide, and
(b) a proteopathic polypeptide other than alpha-synuclein that self-aggregates under pathogenic conditions, wherein illumination of the photoactivatable polypeptide with light having a wavelength sufficient for photoactivation triggers irreversible accumulation of the protein aggregate as defined in claim 1.

14. The system of claim 13, further comprising an illumination source for photoactivation of the photoactivatable polypeptide.

15. The system of claim 13, wherein the photoactivatable polypeptide and/or the alpha-synuclein or other proteopathic polypeptide are fused to a detectable marker.

16. The system of claim 15, wherein the detectable marker is a fluorescent protein, a reporter enzyme, a transcription factor, a radioisotope binding protein, or a bioluminescent protein.

17. The system of claim 13, wherein the cell is comprised in a transgenic rodent, non-human primate, fish, nematode, yeast, or fly engineered to express the fusion protein and the proteopathic polypeptide.

18. The system of claim 13, wherein proteopathic polypeptide is, comprises, or is from huntingtin.

19. The system of claim 13, wherein proteopathic polypeptide is, comprises, or is from: an Aβ precursor protein, an Aβ peptide, Tau, a prion, an Ig light chain, serum amyloid A, transthyretin, cystatin C, beta-2-microglobulin, apolipoprotein AI, apolipoprotein AII, gelsolin, amylin, calcitonin, atrial natriuretic factor, lysozyme, insulin, fibrinogen α-A chain, superoxide dismutase 1, an androgen receptor, an ataxin, a TATA box-binding protein, or TDP-43.

20. The system of claim 13, wherein the photoactivatable polypeptide is, comprises, or is from: a photoreceptor, a cryptochrome, a phytochrome, cryptochrome 2 (CRY2), light-oxygen-voltage (LOV) domains, CRY2-CIB1 (calcium and integrin-binding protein 1) variants, CRY2E490G, CRY2clust, iLID nano and iLID micro, LOVTRAP, Magnets, cobalamin binding domain CBD, VfAU1-LOV, CPH1S, or BphP1-PpsR2.

* * * * *